United States Patent
Garcia-Garcia et al.

(10) Patent No.: US 10,213,407 B2
(45) Date of Patent: Feb. 26, 2019

(54) COMPOUNDS AND METHODS FOR INHIBITING PRODUCTION OF TRIMETHYLAMINE

(71) Applicants: The Procter & Gamble Company, Cincinnati, OH (US); THE CLEVELAND CLINIC FOUNDATION, Cleveland, OH (US)

(72) Inventors: Jose Carlos Garcia-Garcia, CIncinnati, OH (US); Stanley Leon Hazen, Pepper Pike, OH (US); John August Wos, Mason, OH (US)

(73) Assignees: THE PROCTER & GAMBLE COMPANY, Cincinnati, OH (US); THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 15/366,940

(22) Filed: Dec. 1, 2016

(65) Prior Publication Data
US 2017/0152222 A1   Jun. 1, 2017

Related U.S. Application Data

(60) Provisional application No. 62/261,645, filed on Dec. 1, 2015, provisional application No. 62/261,662, filed (Continued)

(51) Int. Cl.
| | |
|---|---|
| C12N 9/00 | (2006.01) |
| A61K 31/26 | (2006.01) |
| A61K 31/145 | (2006.01) |
| A61K 31/166 | (2006.01) |
| A61K 31/216 | (2006.01) |
| A61K 31/22 | (2006.01) |
| A61K 31/325 | (2006.01) |
| A61K 31/351 | (2006.01) |
| A61K 31/5375 | (2006.01) |
| A61K 31/27 | (2006.01) |
| A61K 31/4453 | (2006.01) |
| A61K 45/06 | (2006.01) |
| A61K 31/336 | (2006.01) |
| A61K 31/439 | (2006.01) |
| A61K 31/4425 | (2006.01) |
| A61K 31/452 | (2006.01) |
| C07C 331/20 | (2006.01) |
| C07D 211/46 | (2006.01) |

(Continued)

(52) U.S. Cl.
CPC ............ *A61K 31/26* (2013.01); *A61K 31/04* (2013.01); *A61K 31/095* (2013.01); *A61K 31/145* (2013.01); *A61K 31/166* (2013.01); *A61K 31/216* (2013.01); *A61K 31/22* (2013.01); *A61K 31/27* (2013.01); *A61K 31/275* (2013.01); *A61K 31/325* (2013.01); *A61K 31/336* (2013.01); *A61K 31/351* (2013.01); *A61K 31/439* (2013.01); *A61K 31/4425* (2013.01); *A61K 31/4453* (2013.01); *A61K 31/452* (2013.01); *A61K 31/5375* (2013.01); *A61K 45/06* (2013.01); *C07C 331/20* (2013.01); *C07D 211/46* (2013.01); *C07D 213/04* (2013.01); *C07D 213/30* (2013.01); *C07D 213/65* (2013.01); *C07D 295/13* (2013.01); *C07D 303/36* (2013.01); *C07D 453/02* (2013.01)

(58) Field of Classification Search
CPC .... A61K 31/26; A61K 31/336; A61K 31/439; A61K 31/4425; A61K 31/452; A61K 31/5375; A61K 45/06; A61K 31/04; A61K 31/95; A61K 31/145; A61K 31/166; A61K 31/216; A61K 31/22; A61K 31/27; A61K 31/275; A61K 31/325; A61K 31/351; A61K 31/4453; C07D 331/20; C07D 211/46; C07D 213/04; C07D 213/30; C07D 213/65; C07D 295/04; C07D 295/13; C07D 303/36; C07D 453/02
See application file for complete search history.

(56) References Cited

U.S. PATENT DOCUMENTS

| | | | |
|---|---|---|---|
| 9,168,233 | B2 | 10/2015 | Hazen et al. |
| 9,423,405 | B2 | 8/2016 | Hazen et al. |

(Continued)

OTHER PUBLICATIONS

Baillie et al. (Pesticide Sci. (1975) 6: 645-653 (Year: 1975).*

(Continued)

*Primary Examiner* — Susan M Hanley
(74) *Attorney, Agent, or Firm* — James E. Oehlenschlager

(57) ABSTRACT

The invention provides a method of inhibiting the conversion of choline or carnitine to trimethylamine (TMA) and lowering TMAO in an individual comprising administering to the individual a composition comprising a compound set forth in FORMULA (I):

FORMULA (I)

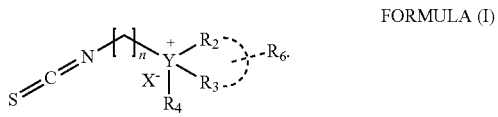

The invention also provides for a method of inhibiting the production of TMA by bacteria comprising administering to the individual a composition comprising a compound set forth in FORMULA (I) wherein the compound is administered in an amount effective to inhibit formation of trimethylamine (TMA) from choline or carnitine in the individual.

19 Claims, No Drawings

Specification includes a Sequence Listing.

Related U.S. Application Data on Dec. 1, 2015, provisional application No. 62/356,422, filed on Jun. 29, 2016.

(51) Int. Cl.
    *C07D 213/04*      (2006.01)
    *C07D 213/30*      (2006.01)
    *C07D 213/65*      (2006.01)
    *C07D 295/13*      (2006.01)
    *C07D 303/36*      (2006.01)
    *C07D 453/02*      (2006.01)
    *A61K 31/04*      (2006.01)
    *A61K 31/095*      (2006.01)
    *A61K 31/275*      (2006.01)

(56) References Cited

U.S. PATENT DOCUMENTS

| 10,064,830 B2 | 9/2018 | Hazen et al. |
| 2012/0157397 A1 | 6/2012 | Hazen et al. |

OTHER PUBLICATIONS

Barrett et al. Ann. Rev. Microbiol. (1985) 39: 131-49 (Year: 1985).*
Zeneng Wang et al: "Gut flora metabolism of phosphatidylcholine promotes cardiovascular disease", Nature, vol. 472, No. 7341, Apr. 6, 2011 (Apr. 6, 2011), pp. 57-63.
International Search Report with Written Opinion, dated Feb. 17, 2017, 13 pages.

* cited by examiner

COMPOUNDS AND METHODS FOR INHIBITING PRODUCTION OF TRIMETHYLAMINE

FIELD OF THE INVENTION

The invention relates to quaternary amine derivatives and their use for inhibiting trimethylamine production.

BACKGROUND OF THE INVENTION

Trimethylamine (TMA) and its derivative trimethylamine-N-oxide (TMAO) are metabolites linked to disorders such as kidney disease, diabetes mellitus, trimethylaminuria, and cardiovascular disease (CVD). Trimethylamine (TMA) is produced in the gut by bacteria which are capable of converting substrates including but not limited to, choline and carnitine, to TMA. Increased levels of TMA may also be produced by bacteria in the vagina leading to vaginal odor, or by bacteria on the body leading to body odor. There is an unmet need for compounds which inhibit the production of TMA by bacteria.

CVD is a general term encompassing a range of conditions affecting the heart and blood vessels, including atherosclerosis, coronary heart disease, cerebrovascular disease, heart failure, cardiomyopathy, atherothrombotic disease, aorto-iliac disease, and peripheral vascular disease. CVD is generally associated with conditions that involve narrowed, blocked, aneurysmal or dissection of one or more blood vessels, or thrombosis (blood clot formation). Complications associated with CVD include, but are not limited to, myocardial infarction, stroke, angina pectoris, acute coronary syndrome, transient ischemic attacks, congestive heart failure, aortic aneurysm, atrial fibrillation or flutter, ventricular arrhythmias, cardiac conduction abnormalities, need for revascularization and death. Revascularization can include but is not limited to angioplasty, stenting, coronary artery bypass grafting, repair or replacement of vascular shunt or access such as an arteriovenous fistula. Complications associated with atherothrombotic disease include, but are not limited to, myocardial infarction, stroke, pulmonary embolism, deep venous thrombosis. According to the World Health Organization, CVDs are the leading cause of death globally, with over 75% of deaths occurring in low- and middle-income countries. World Health Organization Fact Sheet No. 317, updated January 2015. The World Health Organization projects that diabetes will be the seventh leading cause of death in 2030. World Health Organization Fact Sheet No. 312, updated January 2015. Prevention and management of conditions associated with TMA and TMAO, including CVD and diabetes, is a major public health concern.

SUMMARY OF THE INVENTION

The disclosure is based, at least in part, on the discovery that compounds of Formula (I), and Formula (II), inhibit choline and carnitine metabolism by gut microbiota resulting in reduction in the formation of trimethylamine (TMA). The disclosure provides compositions and methods for, e.g., inhibiting the conversion of choline or carnitine to TMA in vitro and in vivo, for improving or maintaining cardiovascular, cerebrovascular, and peripherovascular health, and for improving or preventing a condition associated with TMA and TMAO.

In certain aspects, the invention provides one or more methods of reducing the production of TMAO comprising inhibiting the conversion of choline or carnitine to trimethylamine (TMA) by a bacterium, by contacting the bacterium with one or more compounds as set forth in Formula (I):

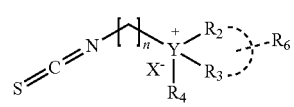

Formula (I)

wherein:
$Y^+$ is selected from a quaternary nitrogen; $X^-$ is Cl, Br, I, or trifluromethanesulfonate; n is selected from 1, 2 or 3; $R_2$ and $R_3$ are independently selected from $C_{1-4}$ alkyl or bound together forming an aliphatic, aromatic or heterocyclic ring system;

$R_4$ is selected from $C_{1-4}$ alkyl, alkenyl, alkynyl, alkoxy carbonyl, alkoxy dicarbonyl, acrylic, alkoxy, alkoxy alkyl, aryloxy alkyl, alkyl carboxylate as part of a betaine, inner salt, or Zwitterion form, halo alkyl, hydroxy alkyl, nitrile, or propargyl;

$R_6$ is selected from $C_{1-4}$ alkyl, alkoxy, hydroxy, alkoxy alkyl, hydroxy alkyl, or epoxy.

In certain aspects, the invention provides one or more methods of inhibiting the conversion of choline or carnitine to trimethylamine (TMA) in an individual.

In certain aspects, the invention provides one or more compounds comprising:

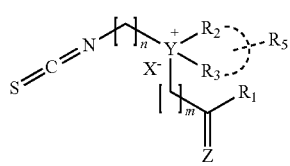

Formula (II)

wherein $R_1$ is H, $C_1$-$C_4$ alkoxy, Br, Cl, F, I, or is selected from

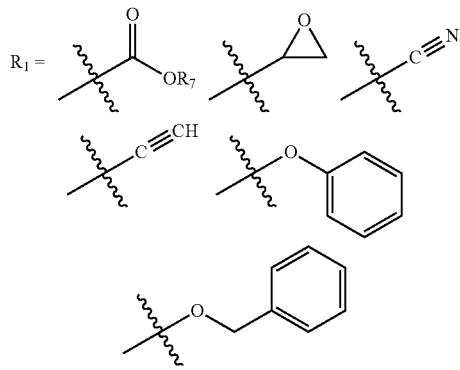

$Y^+$ is selected from a quaternary nitrogen; $X^-$ is any pharmaceutically acceptable salt; n is selected from 1, 2 or 3; $R_2$ and $R_3$ are independently selected from C1-4 alkyl or bound together forming an aliphatic, aromatic or heterocyclic ring system;

Z is O, $CH_2$, or H, H;
m is 0, 1 or 2;
$R_5$ is hydroxyl, or hydroxyl alkyl; and
$R_7$ is H, or $C_{1-4}$ alkyl and
including any acceptable salts or solvates thereof.

The invention further provides for methods to synthesize amino and quaternary amino alkyl isothiocyanate derivatives. Such compounds derivatives may also be used to inhibit the production of TMA by a bacterium, by contacting the bacterium with a composition comprising a composition as set forth in Formula (II).

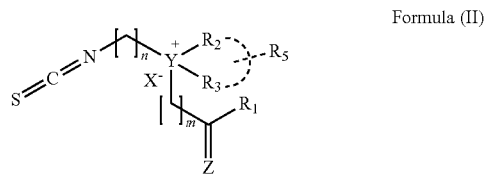

Formula (II)

wherein $R_1$ is H, $C_1$-$C_4$ alkoxy, Br, Cl, F, I, or is selected from

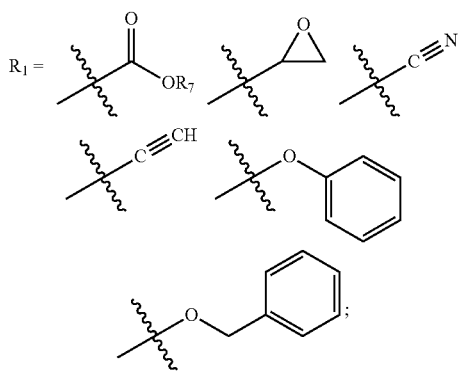

$R_1 =$

Y, $X^-$, n, $R_2$ and $R_3$ are as described in Formula (I); Z is O, $CH_2$, or H, H; m is 0, 1 or 2;

$R_5$ is hydroxyl, or hydroxyl alkyl, and $R_7$ is H, or $C_{1-4}$ alkyl.

In certain aspects, the invention provides one or more methods of inhibiting the conversion of choline or carnitine to trimethylamine (TMA) in an individual. The method comprises administering to the individual a compound set forth in Formula (II).

The compounds of Formula (I), or Formula (II) may be administered to an individual in an amount effective to inhibit the production of TMA by bacteria, for example from substrates including but not limited to choline and/or carnitine.

The invention further provides one or more methods of improving or maintaining cardiovascular health. A method comprises administering to the individual one or more compounds as set forth in Formula (I), or Formula (II), as described herein in an amount that improves or maintains cardiovascular health. The invention also provides one or more methods of improving a condition associated with the conversion of choline or carnitine to trimethylamine (TMA) in an individual. A method comprises administering to the individual one or more compositions comprising a compound as set forth in Formula (I), or Formula (II), as described herein in an amount effective to improve the condition. In some embodiments, the condition is trimethylaminuria, kidney disease, diabetes mellitus, or cardiovascular disease, e.g., angina, arrhythmia, atherosclerosis, cardiomyopathy, congestive heart failure, coronary artery disease (CAD), carotid artery disease, endocarditis, coronary thrombosis, myocardial infarction (MI), high blood pressure/hypertension, hypercholesterolemia/hyperlipidemia, peripheral artery disease (PAD), or stroke.

The invention further provides use of the compounds of Formula (I), or Formula (II), for inhibiting the conversion of choline or carnitine to TMA in vivo or in vitro, for improving or maintaining cardiovascular health, and for improving a condition associated with the conversion of choline or carnitine to TMA. Also provided is the compound of Formula (I), or Formula (II), for use in inhibiting the conversion of choline or carnitine to TMA in vivo or in vitro, for improving or maintaining cardiovascular health, and for improving a condition associated with the conversion of choline or carnitine to TMA.

The foregoing summary is not intended to define every aspect of the invention, and additional aspects are described in other sections, such as the Detailed Description. In addition, the invention includes, as an additional aspect, all embodiments of the invention narrower in scope in any way than the variations defined by specific paragraphs set forth herein. For example, certain aspects of the invention that are described as a genus, and it should be understood that every member of a genus is, individually, an aspect of the invention. Also, aspects described as a genus or selecting a member of a genus should be understood to embrace combinations of two or more members of the genus. With respect to aspects of the invention described or claimed with "a" or "an," it should be understood that these terms mean "one or more" unless context unambiguously requires a more restricted meaning. The term "or" should be understood to encompass items in the alternative or together, unless context unambiguously requires otherwise. If aspects of the invention are described as "comprising" a feature, embodiments also are contemplated "consisting of" or "consisting essentially of" the feature.

DETAILED DESCRIPTION OF THE INVENTION

The components of the present compositions are described in the following paragraphs.

The present invention provides one or more methods of reducing the production of TMA comprising: inhibiting the conversion of choline or carnitine to trimethylamine (TMA) by a bacterium using a composition comprising a compound set forth in Formula (I), or Formula (II). The present invention also provides synthesis methods to produce a series of amino and quaternary amino alkyl isothiocyanate derivatives, as exemplified in Formula (II). Such compounds maybe used to inhibit the production of TMA by bacteria. The compounds of Formula (I), or Formula (II) may be administered to an individual in an amount effective to inhibit the production of TMA and TMAO by bacteria in the gut of an individual, for example from substrates including but not limited to choline and/or carnitine.

Trimethylamine (TMA) synthesized by bacteria resident in the gut of mammals is oxidized in the liver to trimethylamine oxide (TMAO). Exemplary precursors to TMA include choline, betaine, phosphatidylcholine, phosphocholine, glycerophosphocholine, carnitine, acylcarnitines, gamma-butyrobetaine, crotonobetaine, dehydrocarnitine, TMAO, sphingomyelin, and lecithin, many of which are derived from dietary sources such as, for example, dairy products, whole eggs and meats and beef liver. These sources may act as substrates for bacteria that can metabolize them to TMA. Without wishing to be bound to a particular mechanism or biochemical pathway, the anaerobic conversion of choline to TMA is facilitated by a glycyl radical enzyme homologue, choline trimethylamine-lyase (CutC). Craciun et al., Proc. Natl. Acad. Sci. (2012), 109: 21307-21312. The reduction of choline conversion to TMA by bacteria in the gut of an individual leads to a reduction in TMA absorption from the gut, leading to a subsequent reduction in plasma TMAO following oxidation of TMA to TMAO by the Flavin Monooxygenase 3 (FMO3) enzyme in the liver. Wang et al., Nature (2011), 472: 57-63. Lower plasma TMAO levels are related to a lower incidence of major cardiovascular events in humans. Tang et al., NEJM (2013) 368: 1575-1584. The conversion of choline to TMA may be mediated by one species of bacteria or comprise a multi-step process involving two, three or more species of bacteria.

Without wishing to be bound to a particular mechanism or biochemical pathway, the conversion of carnitine to TMA is mediated by an oxygenase/reductase, CntAB. Zhu et al., Proc. Natl. Acad. Sci. (2014), 111: 4268-4273. The reduction of carnitine conversion to TMA by bacteria in the gut of an individual leads to a reduction in TMA absorption from the gut, leading to a subsequent reduction in plasma TMAO following oxidation of TMA to TMAO by the Flavin Monooxygenase enzymes (i.e. FMO3) in the liver. Wang et al., Nature (2011), 472: 57-63. Lower plasma TMAO levels are related to a lower incidence of major cardiovascular events in humans. Tang et al., NEJM (2013) 368: 1575-1584. The conversion of carnitine to TMA in the gut of an individual may occur via a multi-step process, for example, by a two-step process via the metabolism of carnitine to gamma-butyrobetaine followed by the metabolism of gamma butyrobetaine to TMA, facilitated by at least two functionally different bacteria. Koeth et al., Cell Metabolism (2014), 20: 799-812. It will be appreciated that modulating the "conversion of carnitine to TMA" encompasses the conversion of carnitine-associated intermediates to TMA, including intermediates such as, but not limited to, gamma-butyrobetaine, crotonobetaine, dehydrocarnitine (Koeth et al.; Kleber (1997) FEMS Microbiolo. Lett. 147: 1-9), and TMAO.

The invention further provides a method of improving or maintaining cardiovascular health. A method may comprise administering to the individual a composition comprising a compound as set forth in Formula (I), or Formula (II), as described herein in an amount that improves or maintains cardiovascular health. The invention also provides a method of improving a condition associated with the conversion of choline and/or carnitine to trimethylamine (TMA) in an individual. The method comprises administering to the individual a composition comprising a compound as set forth in Formula (I), or Formula (II), as described herein in an amount effective to improve the condition. In some embodiments, the condition is trimethylaminuria, kidney disease, diabetes mellitus, or cardiovascular disease, such as angina, arrhythmia, atherosclerosis, cardiomyopathy, congestive heart failure, coronary artery disease (CAD), carotid artery disease, endocarditis, coronary thrombosis, myocardial infarction (MI), high blood pressure/hypertension, hypercholesterolemia/hyperlipidemia, peripheral artery disease (PAD), or stroke. In some other embodiments, the condition is adverse ventricular remodeling, ventricular systolic dysfunction, ventricular diastolic dysfunction, cardiac dysfunction, ventricular arrhythmia, or oral biofilm formation due to periodontal disease as a symptom of cardiovascular disease.

Trimethylaminuria (TMAU) is a condition characterized by an inability of individuals to convert TMA to TMAO, wherein affected individuals may have a fish-like body odor present in their urine, sweat and/or breath. (Yamazaki et al. Life Sciences (2004) 74: 2739-2747). Such individuals may benefit from a reduction in metabolism of substrates to TMA by bacteria in the gut. Individuals with TMAU or those wishing to reduce their levels of TMA and TMAO, may also consume activated charcoal or copper chlorophyllin, which act as sequestering agents, for example to make TMA unavailable to transfer into the blood stream of an individual. Such sequestering agents may adsorb TMA, which is then excreted from the digestive tract along with the sequestering agent.

The invention further provides the compounds of Formula (I), or Formula (II) for use in inhibiting the conversion of choline or carnitine to TMA in vivo or in vitro, for improving or maintaining a condition associated with the conversion of choline or carnitine to TMA; and use of the compounds of Formula (I), or Formula (II), for inhibiting the conversion of choline or carnitine to TMA in vivo or in vitro, for improving or maintaining a condition associated with the conversion of choline or carnitine to TMA. As described previously, the present invention is based, at least in part, on the discovery that compounds of Formula (I), or Formula (II), inhibit choline and carnitine metabolism by gut microbiota resulting in reduction in the formation of trimethylamine (TMA) and trimethylamine N-oxide (TMAO). The disclosure provides compositions and methods that for example inhibit the conversion of choline or carnitine to TMA in vitro and in vivo, improve or maintain cardiovascular, cerebrovascular, and peripherovascular health, and improve or prevent a condition associated with TMA and TMAO.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at about 22° C. to 25° C. (i.e. room temperature) unless otherwise specified.

As used herein, "dose" refers to a volume of medication, such as liquid medication or oral dosage unit, containing an amount of a drug active suitable for administration on a single occasion, according to sound medical practice. A dose can be orally administered. In one example, a dose can be a liquid medication and can be about 30 mL, in another example about 25 mL, in another example about 20 mL, in another example about 15 mL, and in another example about 10 mL. In another example, a dose of liquid medication can be from about 10 mL to about 75 mL, in another example from about 15 mL to about 50 mL, in another example from about 25 mL to about 40 mL, and in another example from about 28 mL to about 35 mL. In another example, the dose can be a solid dosage form and can be from about 25 mg to about 5 g, in another example from about 100 mg to about 3 g, in another example from about 250 mg to about 2 g, in another example from about 500 mg to about 1.6 g, and in another example from about 750 mg to about 1 g. In addition, a dose may be a solid dosage form wherein one dose is about 3 g or a dose can be about 1.6 g. The concentration of active ingredients can be adjusted to provide the proper doses of actives given the liquid or solid dose size. In certain embodiments, a dose can be administered about every 4 hours, about every 6 hours, about every 8 hours, about every 12 hours, or about every 24 hours.

As used herein, "medication" refers to compositions comprising a compound of Formula (I), or Formula (II), such as pharmaceuticals, including prescription medications, over-the-counter medications, behind-the-counter medications and combinations thereof. In some examples, a medication can be a supplement which can contain vitamins, minerals, and supplements (VMS) including supplements such as botanicals.

Medication compositions can be in any suitable form including liquid compositions and solid oral dosage forms. Non limiting examples of liquid compositions can include syrups, beverages, supplemental water, foam compositions, gel compositions, particles suspended in a liquid formulation, a solid in a gelatin or foam, saline wash and combinations thereof. Non-limiting examples of solid oral dosage forms can include tablets, capsules, caplets, sachets, sublingual dosage forms, buccal dosage forms, soft gels, and other liquid filled capsules, dissolvable dosage forms including dissolvable strips, films, gums including a center filled gum, gummies including a center filled gummy, lozenges, edible foods, such as food bars, center filled tablets, powder, granules, pellets, microspheres, nanospheres, beads, or nonpareils, and combinations thereof. Tablets can include compressed tablets, chewable tablets, dissolvable tablets, and the like. In some examples, the medication can be applied to the skin, in an ointment such as a petroleum jelly based ointment. In some examples the medication may be provided in a delivery device. In other examples, the medication can be inhaled, such as a nose spray or inhaler. In other examples, the medication can be in a drink, such as a warm beverage. In other examples, the medication can contain a pharmaceutical active.

The medications can be in a form that is directly deliverable to the mouth, throat, and/or skin. In some example, the medication compositions can be delivered by a delivery device selected from droppers, pump, sprayers, liquid dropper, saline wash delivered via nasal passageway, cup, bottle, canister, pressurized sprayers, atomizers, air inhalation devices, squeezable sachets, power shots, blister cards, and other packaging and equipment, and combinations thereof. The sprayer, atomizer, and air inhalation devices can be associated with a battery or electric power source.

As used herein the term "individual" includes both humans and other types of mammals sharing the TMAO pathway, such as domesticated animals, including but not limited to, domestic dogs (canines), cats (feline), horses, cows, ferrets, rabbits, pigs, rats, mice, gerbils, hamsters, horses, and the like.

A wide variety of individuals may wish to reduce the level of TMA produced by bacteria in their digestive tract. For example, individuals diagnosed with cardiovascular disease may be directed by a physician to take prescription drugs or effect lifestyle changes to modulate blood cholesterol levels to reduce the risk of serious cardiovascular events. Other individuals not previously diagnosed with cardiovascular disease but who wish to improve or maintain cardiovascular health may also wish to reduce plasma TMAO levels by reducing the level of TMA produced by digestive tract bacteria. As described further herein, a reduction in TMA (and, by extension, TMAO) is achieved by the compositions described herein, which include, for example, a dietary supplement comprising isothiocyanates, such as the compounds of Formula (I), or Formula (II).

The disclosure includes, processes for the synthesis of amine and quaternary amine derivatives, one or more methods of inhibiting the conversion of choline or carnitine to trimethylamine (TMA), one or more methods of improving cardiovascular health, and one or more methods of improving a condition associated with conversion of choline or carnitine to trimethylamine (TMA) comprising administering to the individual a composition comprising a compound of Formula (I), or Formula (II). Features of the compositions and methods are described below. Section headings are for convenience of reading and not intended to be limiting per se. The entire document is intended to be related as a unified disclosure, and it should be understood that all combinations of features described herein are contemplated, even if the combination of features are not found together in the same sentence, or paragraph, or section of this document. It will be understood that any feature of the methods or compounds described herein can be deleted, combined with, or substituted for, in whole or part, any other feature described herein.

Compounds

In certain aspects, the invention provides one or more methods of reducing the production of TMAO comprising inhibiting the conversion of choline or carnitine to trimethylamine (TMA) by a bacterium using one or more compositions comprising a compound set forth in Formula (I).

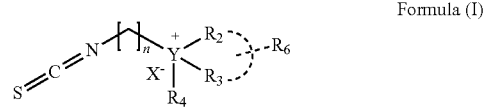

Formula (I)

wherein:

$Y^+$ is selected from a quaternary nitrogen; $X^-$ is Cl, Br, I, or trifluromethanesulfonate; n is selected from 1, 2 or 3; $R_2$ and $R_3$ are independently selected from $C_{1-4}$ alkyl or bound together forming an aliphatic, aromatic or heterocyclic ring system;

$R_4$ is selected from $C_{1-4}$ alkyl, alkenyl, alkynyl, alkoxy carbonyl, alkoxy dicarbonyl, acrylic, alkoxy, alkoxy alkyl, aryloxy alkyl, alkyl carboxylate as part of a betaine, inner salt, or Zwitterion form, halo alkyl, hydroxy alkyl, nitrile, or propargyl;

$R_6$ is selected from $C_{1-4}$ alkyl, alkoxy, hydroxy, alkoxy alkyl, hydroxy alkyl, or epoxy.

Formula (I) also includes one or more salts of any compound encompassed by Formula (I).

In certain embodiments, the compound may be selected from the group consisting of N-(2-Phenoxyethyl)-2-isothiocyanato-N,N-dimethylethan-1-aminium triflate, N-(2-isothiocyanatoethyl)-N,N-dimethylprop-2-yn-1-aminium bromide, 3-Isothiocyanato-N,N-diethyl-N-methylpropanaminium iodide, and N-(2-isothiocyanatoethyl)-2-(methoxycarbonyl)-N,N-dimethylprop-2-en-1-aminium bromide, and pharmaceutically acceptable salts thereof, and combinations thereof.

In certain embodiments, the compound may be selected from the group consisting of N,N-Diethyl-2-isothiocyanato-N-methylpropanaminium iodide, N-(2-Bromoethyl)-3-isothiocyanato-N,N-diethylpropan-1-aminium triflate, N-(Ethoxypropyl-2,3-dione)-3-isothiocyanato-N,N-diethyl-propan-1-aminium bromide, and pharmaceutically acceptable salts thereof, and combinations thereof.

The compound may be administered to an individual in an amount effective to achieve the desired effect, e.g., inhibit conversion of choline or carnitine to TMA, improve or maintain cardiovascular health, and/or improve a condition associated with conversion of choline or carnitine to TMA.

The invention further provides for methods to synthesize amino and quaternary amino alkyl isothiocyanate derivatives. Such compounds derivatives maybe used to inhibit the production of TMA by bacteria. Such compounds are described by Formula (II).

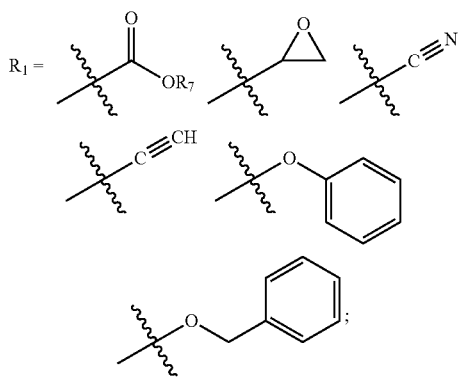

Formula (II)

Wherein $R_1$ is H, $C_1$-$C_4$ alkoxy, Br, Cl, F, I, or is selected from

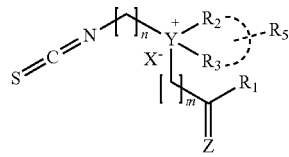

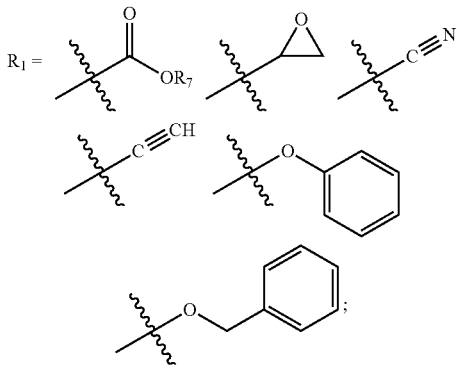

Y, $X^-$, n, $R_2$ and $R_3$ are as described in Formula (I), Z is O, $CH_2$, or H, H; m is 0, 1 or 2, $R_5$ is hydroxyl, or hydroxyl alkyl, and $R_7$ is H, or $C_{1-4}$ alkyl.

$X^-$ is an anion capable of forming a salt with a quaternary ammonium group. In certain embodiments, $X^-$ is a pharmaceutically acceptable anion selected from chloride, bromide, iodide, phosphate, and sulfate salts. Additional pharmaceutically acceptable acid addition salts include, for example, succinate, maleate, tartrate, citrate and glycolate thus $X^-$ may be selected from succinate, maleate, tartrate, citrate and glycolate. $X^-$ is preferably a chloride, bromide, iodide, or trifluoromethanesulfonate or triflate salt form.

Formula (II) also includes one or more salts of any compound encompassed by Formula (II).

Compounds of Formula (II) can be synthesized using the general scheme shown below, with more specific synthesis reactions provided in EXAMPLE 1.

Formula (II)

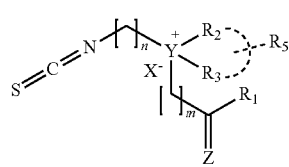

wherein $R_1$ is H, $C_1$-$C_4$ alkoxy, Br, Cl, F, I, or is selected from $Y^+$ is selected from a quaternary nitrogen; $X^-$ is any pharmaceutically acceptable salt; n is selected from 1, 2 or 3; $R_2$ and $R_3$ are independently selected from C1-4 alkyl or bound together forming an aliphatic, aromatic or heterocyclic ring system;

Z is O, $CH_2$, or H, H;

m is 0, 1 or 2;

$R_5$ is hydroxyl, or hydroxyl alkyl; and $R_7$ is H, or $C_{1-4}$ alkyl; and including any acceptable salts or solvates thereof;

reacting compound A;

Compound (A)

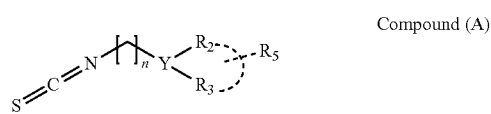

with a compound of structure B:

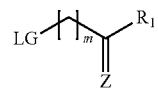

wherein LG is a suitable leaving group known to one skilled in the art.

"Alkyl" refers to straight chained and branched saturated hydrocarbon groups containing 1-30 carbon atoms (i.e., $C_1$-$C_{30}$), for example, 1-20 carbon atoms (i.e., $C_1$-$C_{20}$) or 1-10 carbon atoms (i.e., $C_1$-$C_{10}$). In various embodiments, the alkyl groups of $R_2$, and $R_3$ are independently selected from $C_1$-$C_4$ alkyls, i.e., alkyl groups having a number of carbon atoms encompassing the entire range (i.e., 1 to about 4 carbon atoms), as well as all subgroups (e.g., 1-2, 1-3, 1-4, 2-3, 2-4, 3-4, 1, 2, 3, and 4 carbon atoms). Nonlimiting examples of alkyl groups include allyl, methyl, ethyl, n-propyl, isopropyl, n-butyl, sec-butyl (2-methylpropyl), t-butyl (1,1-dimethylethyl) and propargyl. Unless otherwise indicated, an alkyl group can be an unsubstituted alkyl group or a substituted alkyl group. Alkyl groups optionally can be substituted, for example, with one or more of hydroxy (OH), alkoxy, carboxy, cycloalkyl, heterocycloalkyl, and halo.

The terms "heterocycloalkyl" or "heterocyclic" are defined similarly as cycloalkyl, except the ring contains one to three heteroatoms independently selected from oxygen, nitrogen, or sulfur. Nonlimiting examples of heterocycloalkyl groups include piperdine, tetrahydrofuran, tetrahydropyran, 4H-pyran, dihydrofuran, morpholine, thiophene, 1,4-dioxane, furan, pyridine, pyrrole, pyrrolidine, imidazole, pyrazole, triazole, thiazole, pyrazine, pyran, oxazole, oxazine, thiazine, pyrimidine, and the like. Cycloalkyl and heterocycloalkyl groups can be saturated or partially unsaturated ring systems optionally substituted with, for example, one to three groups, independently selected alkyl, alkenyl, OH, C(O)NH$_2$, NH$_2$, oxo (=O), aryl, haloalkyl, halo, and alkoxy. Heterocycloalkyl groups optionally can be further N-substituted with alkyl, hydroxyalkyl, alkoxyaryl, alkylenearyl, and alkyleneheteroaryl.

The terms "cycloalkyl" or "carbocyclic" refer to an aliphatic cyclic hydrocarbon group containing 3-8 carbon atoms (e.g., 3-5, 5-8, 3, 4, 5, 6, 7, or 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group.

The term "hydroxy" or "hydroxyl" refers to a "—OH" group. The term "amino" or "amine" refers to a —NH$_2$, or a —NH— group, wherein each hydrogen in each of Formula (I), or Formula (II), can be replaced with an alkyl, cycloalkyl, aryl, heteroaryl, or heterocycloalkyl group. "Amine" includes cyclic amines optionally substituted with one or more additional heteroatoms. The term "carboxy" or "carboxyl" refers to a "—COOH" group. The term "thiol" or "sulfhydryl" refers to a "—SH" group. The term "cyano" refers to a —C≡N group, also designated —CN. The term "isocyanyl" refers to a —N≡C group. The term "isocyano" refers to a —N=C=O group. The term "isothiocyano" refers to a —N=C=S group. The term "nitro" refers to a —NO$_2$ group.

A "substituted" alkyl, alkenyl, alkynyl, cycloalkyl, cycloalkenyl, aryl, heteroaryl, or alkoxyl refers to an alkyl, alkenyl, alkynyl, cycloalkyl, cycloalkenyl, aryl, heteroaryl, or alkoxyl having at least one hydrogen radical that is substituted with a non-hydrogen radical (i.e., a substituent). Examples of non-hydrogen radicals (or substituents) include, but are not limited to, alkyl, cycloalkyl, alkenyl, cycloalkenyl, alkynyl, ether, aryl, heteroaryl, heterocycloalkyl, hydroxyl, oxy (or oxo), alkoxyl, ester, thioester, acyl, carboxyl, cyano, nitro, amino, amido, or sulfur. When a substituted alkyl group includes more than one non-hydrogen radical, the substituents can be bound to the same carbon or two or more different carbon atoms.

Physiologically acceptable salts of quaternary amines are contemplated and can be formed by reacting a tertiary amine compound with an alkylating agent containing a suitable leaving group. Leaving groups commonly employed in alkylation reactions with amines are known in the art. Leaving groups such as, but not limited to those skilled in the art, include the halides (chlorine, bromine, iodine, etc.) and sulfonate esters of alcohols (tosylate, mesylate, triflate, etc.). Physiologically accepted salts can be formed directly from the alkylation reaction of a tertiary amine with an alkylating agent or can be prepared by an ion exchange process. Physiologically accepted salts include but are not limited to quaternary amine halides, phosphates, carboxylates, and sulfonates.

Salts, such as physiologically acceptable salts, of the disclosed compounds are contemplated and optionally are prepared by alkylation. Acids commonly employed to form physiologically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Physiologically acceptable salts include sulfate, pyrosulfate, bisulfate, sulfite, bisulfite, phosphate, monohydrogenphosphate, dihydrogenphosphate, metaphosphate, pyrophosphate, chloride, bromide, iodide, trifluoromethanesulfonate or triflate, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, O-hydroxybutyrate, glycolate, maleate, tartrate, bitartrate, methanesulfonate, propanesulfonate, naphthalene-1-sulfonate, naphthalene-2-sulfonate, mandelate and other salts. Physiologically acceptable acid addition salts include, e.g., those formed with mineral acids such as hydrochloric acid and hydrobromic acid and those formed with organic acids such as maleic acid.

Physiologically acceptable base addition salts may be formed with metals or amines, such as alkali and alkaline earth metals or organic amines. Physiologically acceptable salts of compounds may also be prepared with a physiologically acceptable cation. Suitable physiologically acceptable cations are well known in the art and include alkaline, alkaline earth, ammonium and quaternary ammonium cations. Carbonates or hydrogen carbonates are also options in this regard. Examples of metals used as cations are sodium, potassium, magnesium, ammonium, calcium, ferric, and the like. Examples of suitable amines include, but are not limited to, isopropylamine, histidine, N,N'-dibenzylethylenediamine, chloroprocaine, diethanolamine, dicyclohexylamine, ethylenediamine, N-methylglucamine, and procaine.

In various embodiments, the compound of Formula (I), or Formula (II), demonstrates an IC$_{50}$ of $1\times10^{-3}$ or less, $5\times10^{-3}$ or less, $1\times10^{-4}$ or less, $5\times10^{-4}$ or less, $1\times10^{-5}$ or less, $5\times10^{-5}$ or less, or $1\times10^{-6}$ or less, or $1\times10^{-7}$ or less, or $1\times10^{-8}$ or less, or $1\times10^{-9}$ or less, or between $1\times10^{-9}$ and $1\times10^{-3}$, or between $1\times10^{-9}$ and $1\times10^{-6}$, or between $1\times10^{-8}$ and $1\times10^{-6}$, or between $1\times10^{-6}$ and $1\times10^{-3}$, between $1\times10^{-6}$ and $1\times10^{-4}$, between $1\times10^{-6}$ and $1\times10^{-5}$, between $1\times10^{-5}$ and $1\times10^{-3}$, or between $1\times10^{-4}$ and $1\times10^{-3}$ (observed 50% inhibition of TMA (or TMAO) formation from choline or carnitine; mol/L), optionally in the assay described in the Examples. In various embodiments, the compound of Formula (I), or Formula (II) demonstrates an IC$_{50}$ of between $1\times10^{-8}$ to $1\times10^{-3}$, or between $1.2\times10^{-6}$ to $2\times10^{-3}$, or between $1\times10^{-6}$ to $1\times10^{-4}$ (observed 50% inhibition of TMA formation from choline; mol/L) in the assay described in Example 2. In various embodiments, the compound of Formula (I), or Formula (II) demonstrates an IC$_{50}$ of between $1\times10^{-5}$ to $1\times10^{-2}$, or $1\times10^{-4}$ to $1\times10^{-3}$ (observed 50% inhibition of TMA formation from carnitine; mol/L) in the assay described in Example 3.

The invention includes a method of inhibiting the conversion of choline or carnitine to trimethylamine (TMA) in an individual which may comprise administering to an individual a composition comprising a compound set forth in Formula (I), or Formula (II), as described previously. In certain embodiments, as described herein, an individual may be in need of reduced TMA levels, improvement of cardiovascular health, and the like. An individual may exhibit an elevated level of TMA or a metabolite thereof (e.g., TMAO, dimethylamine (DMA), or methylamine (MA, also known as monomethylamine or MMA)) prior to administration. In various embodiments, an individual suffers from cardiovascular disease, ingests a diet high in choline or carnitine, or exhibits one or more CVD risk factors (e.g., smoking, stress, high total cholesterol, high LDL cholesterol, low HDL cholesterol, age, hypertension, family history of CVD, obesity, prediabetes, diabetes, or the like).

A method of inhibiting the conversion of choline or carnitine to TMA in vitro is also contemplated. For example a method may comprise contacting a bacterium, such as a bacterium that is represented in the gut microbiota, or a bacterial lysate that metabolizes choline or carnitine to produce TMA with a compound of Formula (I), or Formula (II), as described previously. In various embodiments, a bacterium may be selected from *Proteus mirabilis, Desulfovibrio alaskensis, Clostridium ljungdahlii, C. scindens, C. aldenense, C. aminobutyricum, Collinsella tanakaei, Anaerococcus vaginalis, Streptococcus dysgalactiae, Desultitobacterium hafniense, Klebsiella variicola, K. pneumonia, Proteus penneri, Eggerthella lento, Edwardsiella tarda, Escherichia coli, E. fergusonii*, or a combination thereof. In certain embodiments the bacterium may be one which expresses the cutC/D gene cluster. In certain embodiments, the bacterium may be one which expresses oxygenase/reductase CntAB. The disclosure further provides a method of identifying a compound that inhibits TMA production. The method comprises contacting a bacterium, such as a bacterium that is part of the gut microbiota, or a bacterial lysate that metabolizes choline or carnitine to produce TMA with a candidate compound, such as a compound of Formula (I), or Formula (II), and detecting TMA (or a metabolite thereof). In certain embodiments, the level of TMA (or metabolite thereof) produced by the bacterium in contact with the candidate compound is compared to (a) the level of TMA produced by a bacterium or lysate not contacted with a candidate compound or known TMA inhibitor or (b) the level of TMA produced by the bacterium prior to contact with the candidate compound. A reduction in the level of TMA produced by the bacterium indicates that the candidate compound inhibits conversion of choline or carnitine to TMA.

A method of inhibiting the conversion of choline or carnitine to TMA in vitro also is contemplated. The method comprises contacting bacteria or bacterial lysate with one or more compounds of Formula (I), or Formula (II). In various embodiments, the bacteria comprises a single bacterial species or strain, or contains a mixture of two or more (for example three, four, five, or more) different bacterial species or bacterial strains. Similarly, a bacterial lysate may be produced from a single bacterial species or strain, or a mixture of two or more (for example three, four, five, or more) different bacterial species or bacterial strains.

It will be appreciated that "inhibiting conversion of choline or carnitine to TMA" does not require complete elimination of TMA production via choline or carnitine metabolism. Any reduction in TMA formation from choline or a choline related metabolite as a precursor is contemplated. Any reduction in TMA formation from carnitine or a carnitine related metabolite as a precursor is contemplated. For example at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% reduction; or from about 1% to about 100%, about 10% to about 90%, about 20% to about 80%, about 30% to about 70%, about 40% to about 60%; or any other numerical range which is narrower and which falls within such broader numerical range, as if such narrower numerical ranges were all expressly written herein.

Any suitable method for measuring TMA in vitro or in vivo can be used in the context of the invention. TMA, metabolites of TMA (including TMAO, DMA, or MA), stable isotopes of TMA (such as deuterium labeled TMA, such as d3-, d6-, or d9-TMA), stable isotopes of TMAO (such as deuterium labeled TMAO, such as d3-, d6-, or d9-TMAO), stable isotopes of DMA (such as deuterium labeled DMA, such as d3-, or d6-DMA), stable isotopes of MA (such as deuterium labeled MA, such as d3-MA), and/or choline (including stable isotopes of choline, for example d9-choline), and/or carnitine (including stable isotopes of carnitine, for example d9-carnitine), can be assessed quantitatively or qualitatively. Exemplary methods of detecting and quantifying TMA are described in, for example U.S. Pub. No. 2010/00285517, the disclosure of which is incorporated herein by reference in its entirety. For example, levels of TMA (or trimethylamine-N-oxide (TMAO), DMA, or MA), carnitine and/or choline are optionally measured via mass spectrometry, ultraviolet spectroscopy, or nuclear magnetic resonance spectroscopy. Mass spectrometers include an ionizing source (such as electrospray ionization, MS-ESI), an analyzer to separate the ions formed in the ionization source according to their mass-to-charge (m/z) ratios, and a detector for the charged ions. In tandem mass spectrometry, two or more analyzers are included. Such methods are standard in the art and include, for example, HPLC with on-line electrospray ionization (ESI) and tandem mass spectrometry.

In various embodiments, TMA and/or TMAO is measured in a biological sample from an individual. Biological samples include, but are not limited to, whole blood, plasma, serum, urine, feces, saliva, sweat, vaginal fluids, and/or tissue. The sample may be collected using any clinically-acceptable practice and, if desired, diluted in an appropriate buffer solution, heparinized, concentrated, or fractionated. Any of a number of aqueous buffer solutions at physiological pH, such as phosphate, Tris, or the like, can be used. Acidified buffers also may be used. For example, the final pH after adding buffer to sample may optionally be between pH 1 and pH 6, or between pH 1.5 and pH 3.0.

In addition, levels of TMA (or a metabolite or stable isotope thereof), carnitine, and/or choline in the biological sample may be compared to a control value. The control value utilized will depend on the embodiment of the invention. In certain embodiments, the control value may be the level of TMA and/or TMAO produced in the individual (or by the bacterium) prior to administration or exposure to a compound of Formula (I), or Formula (II). In addition, the control value may be based on levels measured in comparable samples obtained from a reference group such as a group of individuals from the general population, individuals diagnosed with a CVD or other TMA-associated condition, individuals not previously diagnosed with a TMA-associated condition, nonsmokers, and the like, who have not been exposed to a compound of Formula (I), or Formula (II). Levels of TMA and/or TMAO, carnitine, and/or choline may be compared to a single control value or to a range of control values. An individual is optionally identified as having an enhanced or elevated level of TMA prior to administration by comparing the amount of TMA in a biological sample from the individual with a control value.

The invention further provides a method of improving cardiovascular health of an individual. The method comprises administering to the individual a composition comprising a compound set forth in Formula (I), or Formula (II), as described above under the subheading "Compounds" in an amount effective to improve cardiovascular health. Cardiovascular health is assessed by testing arterial elasticity, blood pressure, ankle/brachial index, electrocardiogram, ventricular ultrasound, platelet function (for example platelet aggregation), and blood/urine tests to measure, for example cholesterol, albumin excretion, C-reactive protein, or plasma B-type peptide (BNP) concentration. In various aspects of the invention, administration of the compound of Formula (I), or Formula (II), improves or maintains one or more of the assay outcomes within normal ranges. Normal ranges of outcomes of each test are known in the art. Improvement in cardiovascular health is, in some embodiments, marked by a reduction in circulating total cholesterol levels, reduction in circulating low density lipoproteins (LDLs), reduction in circulating triglycerides, and/or reduction in blood pressure.

The invention also includes a method of improving a condition associated with conversion of choline or carnitine to trimethylamine (TMA) in an individual in need thereof. The method comprises administering to an individual a composition comprising a compound of Formula (I), or Formula (II), as described previously, in an amount effective to improve the condition. "Improving a condition" refers to any reduction in the severity and/or onset of symptoms associated with a disorder caused, at least in part, by TMA. One of ordinary skill in the art will appreciate that any degree of protection from, or amelioration of, a TMA-related disorder or symptom associated therewith is beneficial to an individual, such as a human. The quality of life of an individual is improved by reducing to any degree the severity of symptoms in an individual and/or delaying the appearance of symptoms. Accordingly, a method in certain aspects is performed as soon as possible after it has been determined that an individual is at risk for developing a TMA-related disorder or as soon as possible after a TMA-related disorder is detected.

In various embodiments, administration of the compound of Formula (I), or Formula (II), results in reduced TMA and/or TMAO levels, reduced total cholesterol levels, reduced LDL levels, increased HDL levels, reduced triglyceride levels, and/or normalized levels of other biomarkers associated with CVD (for example excreted albumin, C-reactive protein, or plasma B-type peptide (BNP)). In some embodiments, the compound of Formula (I), or Formula (II), reduces the risk of cardiovascular disease, reduced or impaired kidney function, chronic kidney disease, trimethylaminuria, or diabetes mellitus, when administered to an individual.

Administration Regimens and Compositions

The amount of compound administered to the individual is sufficient to inhibit (in whole or in part) formation of TMA from choline or carnitine. In various aspects of the disclosure, the amount improves cardiovascular health and/or achieves a beneficial biological response with respect to an unwanted condition associated with TMA (for instance the amount is sufficient to ameliorate, slow the progression, or prevent a condition (such as CVD)). The effect can be detected by, for example, an improvement in clinical condition, reduction in symptoms, or by any of the assays or clinical diagnostic tests described herein. The precise effective amount for an individual can depend upon the individual's body weight, size, and health; the nature and extent of the condition; and the compound or combination of agents selected for administration. In various aspects, the amount of compound administered to an individual is about 0.001 mg/kg to about 1000 mg/kg. Specific ranges of doses in mg/kg include about 0.1 mg/kg to about 500 mg/kg, about 0.5 mg/kg to about 200 mg/kg, about 1 mg/kg to about 100 mg/kg, about 2 mg/kg to about 50 mg/kg, and about 5 mg/kg to about 30 mg/kg. An effective amount may be administered to an individual as a single deployment of compound or as a divided dose (such as a single dose administered in multiple subunits contemporaneously or close in time). An amount of compound is optionally delivered one, two, or three times a day; one, two, or three times a week; or one, two, three, or four times a month. The compound may be delivered as a prodrug which is converted to an active drug in vitro or in vivo.

The compound or composition comprising the compound is administered by any route that allows inhibition of choline conversion to TMA, or carnitine conversion to TMA. The compound or composition comprising the compound is, in various aspects of the invention, delivered to an individual parenterally (for example intravenously, intraperitoneally, intrapulmonary, subcutaneously or intramuscularly), intrathecally, topically, transdermally, rectally, orally, sublingually, nasally or by inhalation. In various embodiments, the compound is administered to the gastrointestinal tract via, such as by ingestion. Sustained release formulations may also be employed to achieve a controlled release of the compound when in contact with body fluids in the gastrointestinal tract. Sustained release formulations are known in the art, and typically include a polymer matrix of a biological degradable polymer, a water-soluble polymer, or a mixture of both, optionally with suitable surfactants.

The invention provides a composition comprising the compound of Formula (I), or Formula (II), formulated with one or more physiologically acceptable excipients, carriers, stabilizers, or diluent for use in the methods described herein. Excipients include, but are not limited to, carrier molecules that include large, slowly metabolized macromolecules such as proteins, polysaccharides, polylactic acids, polyglycolic acids, polymeric amino acids, amino acid copolymers, antioxidants (for example ascorbic acid), chelating agents (for example EDTA), carbohydrates (for example dextrin, hydroxyalkylcellulose, and/or hydroxyalkylmethylcellulose), liposomes, stearic acid, liquids (for example oils, water, saline, glycerol and/or ethanol), wetting or emulsifying agents, pH buffering substances, and the like.

Formulations, such as for parenteral or oral administration, are typically solids (for example, a lyophilized powder or cake), liquid solutions, emulsions or suspensions, while inhalable formulations for pulmonary administration are generally liquids or powders. Exemplary dosage forms include, but are not limited to, tablets, troches, lozenges, aqueous or oil suspensions, non-aqueous solutions, powders, dispersible powders or granules (including micronized particles or nanoparticles), emulsions, hard or soft capsules, hard or soft liquid-filled capsules, gelatin capsules, syrups, and elixirs. Solid dose formulations, for example tablets or liquid filled capsules may be uncoated or may be coated by known techniques including microencapsulation to delay disintegration and adsorption in the gastrointestinal tract. Solid dose formulations may be coated to target delivery to a specific region of the digestive tract. For example, the formulation may be enteric coated to target delivery of the formulation to the small intestine, the large intestine, or to the colon. Additional exemplary dosage forms may comprise coated microcapsules or coated microbeads in a suspension or liquid chassis. In some embodiments, the compound of Formula (I), or Formula (II), is provided as a dietary (for example food or drink) supplement. Dietary supplements are orally dosed and typically comprise vitamins, minerals, herbs or other botanicals, amino acids, enzymes, organ tissues, tissues from glands, or metabolites. For example the compound of Formula (I), or Formula (II), may be provided as a food in the form of a bar.

In some embodiments, the compounds described herein may be formulated for oral administration in a lipid-based formulation suitable for low solubility compounds. Lipid-based formulations can generally enhance the oral bioavailability of such compounds. As such, the composition comprises in some aspects, an amount of a compound described herein together with at least one excipient selected from medium chain fatty acids and propylene glycol esters thereof (e.g., propylene glycol esters of edible fatty acids, such as caprylic and capric fatty acids) and physiologically acceptable surfactants, such as polyoxyl 40 hydrogenated castor oil.

In some embodiments, the compounds described herein may be provided in a delayed release formulation, and are optionally released in a specific region of the digestive tract of an individual. For example, the formulation may be provided such that the compounds are released from an orally dosed formulation in the distal portion of the digestive tract such as the ileum or the colon. In certain embodiments, the delayed release formulation releases the compounds at a specific pH, or at a range of pH for targeted delivery within the digestive tract of an individual. The compounds may be released, for example, between pH 6.0 and pH 9.0, between pH 6.5 and pH 8.0, between pH 6.5 and pH 7.5, between pH 7.0 and pH 7.5, or between pH 7.0 and pH 8.0.

A method of the invention may comprise administering a second agent to an individual. The term "second agent" merely serves to distinguish the agent from the compound of Formula (I), or Formula (II), and is not meant to limit the number of additional agents used in a method or denote an order of administration. One or more second agents are optionally incorporated in the composition with the compound of Formula (I), or Formula (II), administered concurrently but in separate dosage forms, or administered separately in time.

Exemplary second agents include, but are not limited to: antimicrobials (such as antibiotics that kill bacteria in the gut); agents that improve intestinal motility (such as fiber or psyllium); agents that further reduce TMA levels in the gut including sequestering agents (such as activated charcoal or copper chlorophyllin); agents that further reduce the production of TMA metabolites; agents that improve one or more aspects of cardiovascular health, such as agents that normalize blood pressure, decrease vascular inflammation, reduce platelet activation, normalize lipid abnormalities; agents that promote the excretion of TMA from the body; or agents that bind TMA so that it cannot be converted into TMAO In various embodiments, the second agent is selected from the group consisting of Omega 3 oil, salicylic acid (aspirin), dimethylbutanol, garlic oil, olive oil, hill oil, Co enzyme Q-10, a probiotic, a prebiotic, a dietary fiber, psyllium husk, bismuth salts, phytosterols, grape seed oil, green tea extract, vitamin D, an antioxidant (such as vitamin C and vitamin E), turmeric, curcumin, resveratrol, activated charcoal, or copper chlorophyllin. Optionally, the composition comprises dimethylbutanol and/or inhibitors of the formation of TMA from precursors other than choline or carnitine (for example betaine, phosphatidylcholine, or crotonobetaine).

Alternatively or in addition, a method of the disclosure may further comprise administration of one or more cardiovascular disease therapies. Examples of therapies include, but are not limited to, statins (e.g., Lipitor™ (atorvastatin), Pravachol™ (pravastatin), Zocor™ (simvastatin), Mevacor™ (lovastatin), and Lescol™ (fluvastatin)) or other agents that interfere with the activity of HMGCoA reductase, nicotinic acid (niacin, which lowers LDL cholesterol levels), fibrates (which lower blood triglyceride levels and include, for example Bezafibrate (such as Bezalip®), Ciprofibrate (such as Modalim®), Clofibrate, Gemfibrozil (such as Lopid®) and Fenofibrate (such as TriCor®)), bile acid resins (such as Cholestyramine, Colestipol (Colestid), and Cholsevelam (Welchol)), cholesterol absorption inhibitors (such as Ezetimibe (Zetia®, Ezetrol®, Ezemibe®)), phytosterols such as sitosterol (Take Control (Lipton)), sitostanol (Benechol), or stigmastanol), alginates and pectins, lecithin, and nutraceuticals (such as extract of green tea and other extracts that include polyphenols, particularly epigallocatechin gallate (EGCG), Cholest-Arrest™ (500 mg garlic and 200 mg lecithin). Cholestaway™ (700 mg Calcium carbonate, 170 mg magnesium oxidem 50 μg chromium picolinate), Cholest-Off™ (900 mg of plant sterols/stanols), Guggul Bolic (750 mg gugulipid (Commiphora mukul gum resin), and Kyolic® (600 mg aged garlic extract and 380 mg lecithin)).

In related variations of the preceding embodiments, a composition comprising a compound of Formula (I), or Formula (II), described herein, alone or in combination with one or more second agents(s), may optionally be arranged in a kit or package or unit dose, such as a kit or package or unit dose permitting co-administration of multiple agents. In another aspect, the composition comprising a compound of Formula (I), or Formula (II), and the one or more second agents are in admixture. In various embodiments, the component(s) of the kit or package or unit dose are packaged with instructions for administering the component(s) to an individual.

Other aspects and advantages of the present invention will be understood upon consideration of the following illustrative examples, which are not intended to be limiting in any way.

Structures of representative compounds of Formula (I), and Formula (II) are set forth in TABLE 1. In TABLE 1, compounds marked by * fall under Formula (I), and compounds marked by # fall under Formula (II). Salt forms may include chloride, bromide, iodide or triflate.

TABLE 1

| ID | * or # | Structure | Compound |
|---|---|---|---|
| 1 | * | 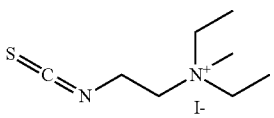 | N,N-Diethyl-2-isothiocyanato-N-methylpropanaminium iodide |

TABLE 1-continued

| ID | * or # | Structure | Compound |
|---|---|---|---|
| 2 | * | 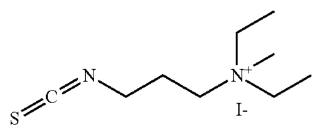 | 3-Isothiocyanato-N,N-diethyl-N-methylpropanaminium iodide |
| 3 | *, # | 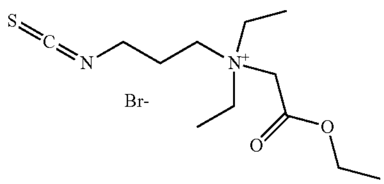 [SMILES: CCOC(=O)C[N+](CC)(CC)CCCN=C=S ; [Br-]] | N-(Ethoxycarbonylethyl)-3-isothiocyanato-N,N-diethylpropan-1-aminium bromide |
| 4 | *, # | 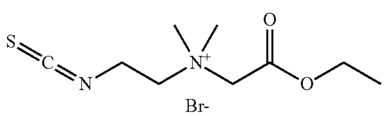 | N-(Ethoxycarbonylethyl)-2-isothiocyanato-N,N-dimethylethan-1-aminium bromide |
| 5 | *, # | 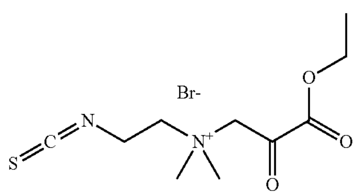 [SMILES: CCOC(=O)C(=O)C[N+](C)(C)CCN=C=S ; [Br-]] | N-(Ethoxypropyl-2,3-dione)-2-isothiocyanato-N,N-dimethylethan-1-aminium bromide |
| 6 | *, # | 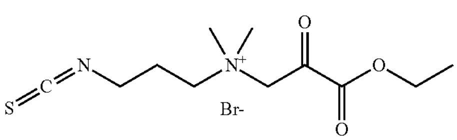 [SMILES: CCOC(=O)C(=O)C[N+](C)(C)CCCN=C=S ; [Br-]] | N-(Ethoxypropyl-2,3-dione)-3-isothiocyanato-N,N-diethylpropan-1-aminium bromide |
| 7 | *, # | 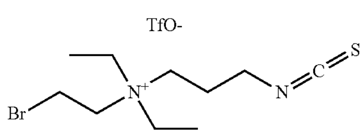 | N-(2-Bromoethyl)-3-isothiocyanato-N,N-diethylpropan-1-aminium triflate |
| 8 | *, # | 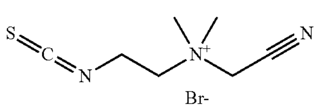 | N-Cyanomethyl-2-isothiocyanato-N,N-diethylethan-1-aminium bromide |
| 9 | *, # | 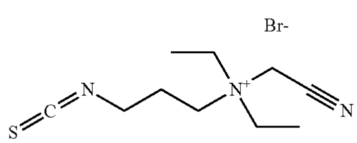 | N-Cyanomethyl-3-isothiocyanato-N,N-diethylpropan-1-aminium bromide |
| 10 | *, # | 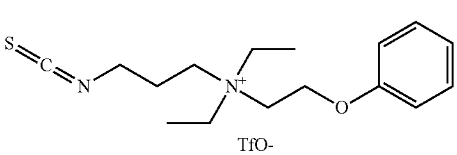 | N-(2-Phenoxyethyl)-3-isothiocyanato-N,N-diethylpropan-1-aminium triflate |
| 11 | *, # | 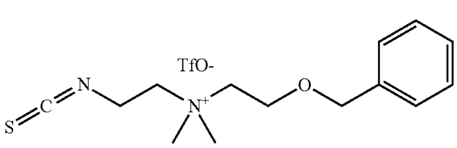 [SMILES: C[N+](C)(CCN=C=S)CCOCc1ccccc1 ; "TfO-"] | N-(2-Benzyloxyethyl)-2-isothiocyanato-N,N-dimethylethan-1-aminium triflate |

TABLE 1-continued

| ID | * or # | Structure | Compound |
|---|---|---|---|
| 12 | *, # | 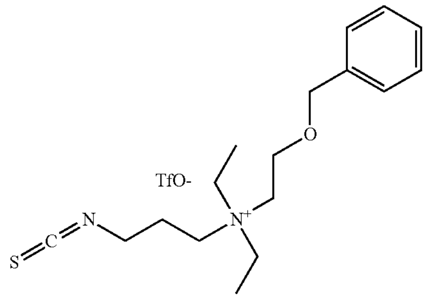 [SMILES: CC[N+](CC)(CCCN=C=S)CCOCc1ccccc1 ; "TfO-"] | N-(2-Benzyloxyethyl)-3-isothiocyanato-N,N-diethylpropan-1-aminium triflate |
| 13 | *, # | 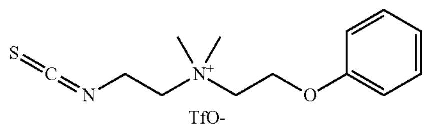 | N-(2-Phenoxyethyl)-2-isothiocyanato-N,N-dimethylethan-1-aminium triflate |
| 14 | *, # | 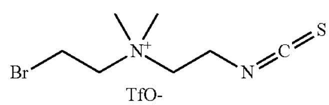 | N-(2-Bromoethyl)-2-isothiocyanato-N,N-dimethylethan-1-aminium triflate |
| 15 | *, # | 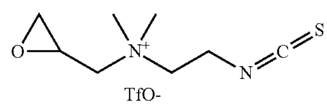 | N-(Oxiranylmethyl)-2-isothiocyanato-N,N-dimethylethan-1-aminium triflate |
| 16 | *, # | 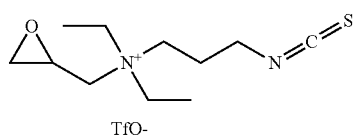 | N-(Oxiranylmethyl)-3-isothocyanato-N,N-diethylpropan-1-aminium triflate |
| 17 | *, # | 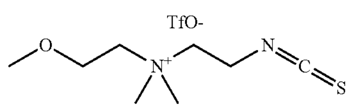 | N-(2-Methoxyethyl)-2-isothiocyanato-N,N-dimethylethan-1-aminium triflate |
| 18 | *, # | 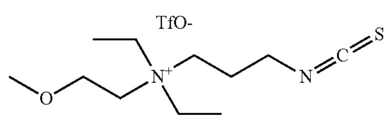 | N-(2-Methoxyethyl)-3-isothiocyanato-N,N-diethylpropan-1-aminium triflate |
| 19 | *, # | 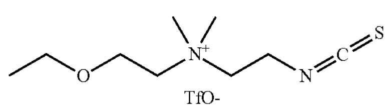 | N-(2-Ethoxyethyl)-2-isothiocyanato-N,N-dimethylethan-1-aminium triflate |
| 20 | *, # | 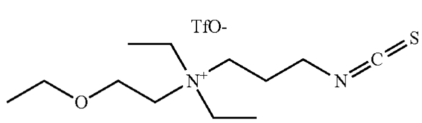 [SMILES: CCOCC[N+](CC)(CC)CCCN=C=S ; "TfO-"] | N-(2-Ethoxyethyl)-3-isothiocyanato-N,N-diethylpropan-1-aminium triflate |
| 21 | *, # | 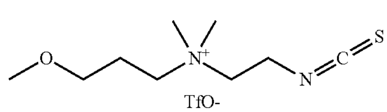 | N-(3-Methoxypropyl)-2-isothiocyanato-N,N-dimethylethan-1-aminium triflate |
| 22 | *, # | 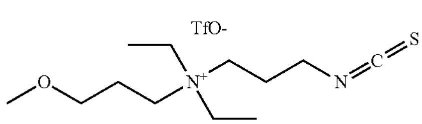 [SMILES: CC[N+](CC)(CCCN=C=S)CCCOC ; "TfO-"] | N-(3-Methoxyethyl)-3-isothiocyanato-N,N-diethylpropan-1-aminium triflate |

TABLE 1-continued

| ID | * or # | Structure | Compound |
|---|---|---|---|
| 23 | *, # | 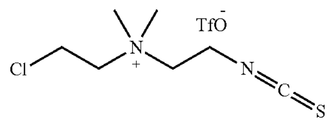 | N-(2-Chloroethyl)-2-isothiocyanato-N,N-dimethylethan-1-triflate |
| 24 | *, # | 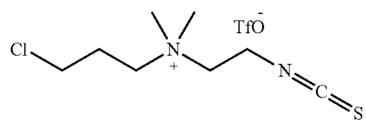 | N-(3-Chloropropyl)-2-isothiocyanato-N,N-dimethylethan-1-aminium triflate |
| 25 | *, # | 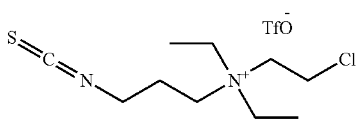 | N-(2-Chloroethyl)-3-isothiocyanato-N,N-diethylpropan-1-aminium triflate |
| 26 | *, # | 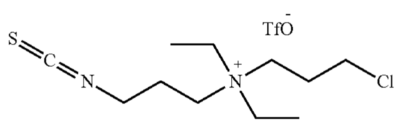 | N-(3-Chloropropyl)-3-isothiocyanato-N,N-diethylpropan-1-aminium triflate |
| 27 | *, # | 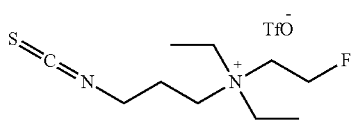 | N-(2-Fluoroethyl)-3-isothiocyanato-N,N-diethylpropan-1-aminium triflate |
| 28 | *, # | 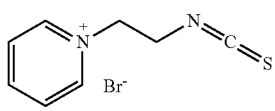 | 1-(2-Isothiocyanatoethyl)pyridin-1-ium bromide |
| 29 | *, # | 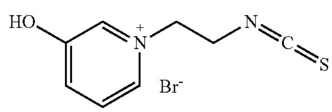 | 1-(2-Isothiocyanatoethyl)-3-hydroxypyridinium bromide |
| 30 | *, # | 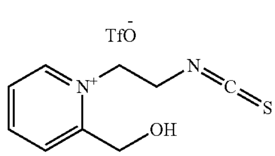 [SMILES: OCc1cccc[n+]1CCN=C=S] | 1-(2-Isothiocyanatoethyl)-(2-hydroxymethyl)pyridinium triflate |
| 31 | *, # | 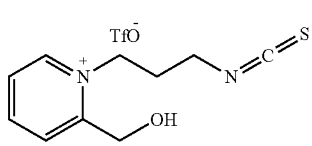 | 2-(hydroxymethyl)-1-(3-isothiocyanatopropyl)pyridin-1-ium trifluoromethanesulfonate |
| 32 | *, # | 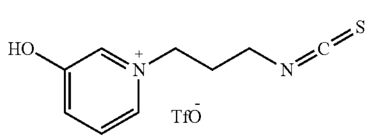 | 3-hydroxy-1-(3-isothiocyanatopropyl)pyridin-1-ium trifluoromethanesulfonate |
| 33 | *, # | 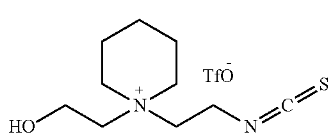 | 1-(2-hydroxyethyl)-1-(2-isothiocyanatoethyl)piperidin-1-ium trifluoromethanesulfonate |

TABLE 1-continued

| ID | * or # | Structure | Compound |
|---|---|---|---|
| 34 | *, # | 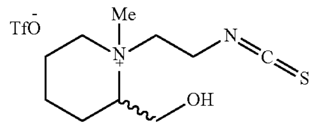 [SMILES: C[N+]1(CCN=C=S)CCCCC1CO] | 2-(hydroxymethyl)-1-(2-isothiocyanatoethyl)-1-methylpiperidin-1-ium trifluoromethanesulfonate |
| 35 | *, # | 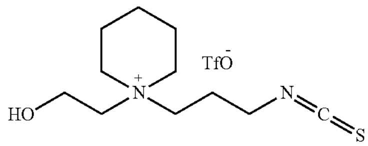 | 1-(2-hydroxyethyl)-1-(3-isothiocyanatopropyl)piperidin-1-ium trifluoromethanesulfonate |
| 36 | *, # | 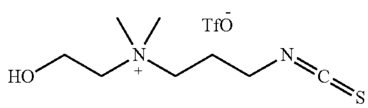 | N-(2-hydroxyethyl)-3-isothiocyanato-N,N-dimethylpropan-1-aminium trifluoromethanesulfonate |
| 37 | *, # | 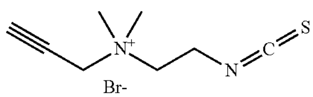 | N-(2-isothiocyanatoethyl)-N,N-dimethylprop-2-yn-1-aminium bromide |
| 38 | *, # | 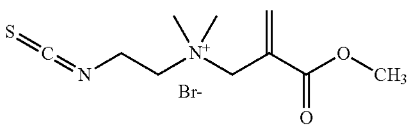 | N-(2-isothiocyanatoethyl)-2-(methoxycarbonyl)-N,N-dimethylprop-2-en-1-aminium bromide |
| 39 | *, # | 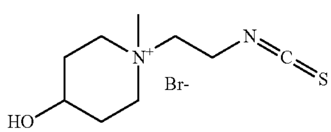 | 4-hydroxy-1-(2-isothiocyanatoethyl)-1-methylpiperidin-1-ium bromide |
| 40 | *, # | 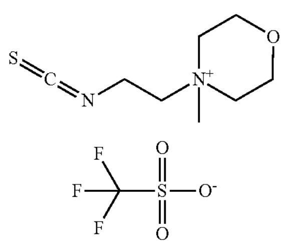 | 4-Methyl-4-(2-isothiocyanatoethyl)morpholinium trifluoromethanesulfonate |
| 41 | *, # | 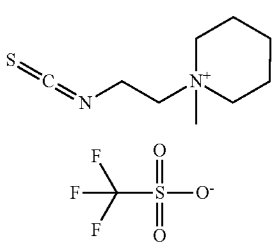 | 1-Methyl-1-(2-isothiocyanatoethyl)piperidium trifluoromethanesulfonate |
| 42 | *, # | 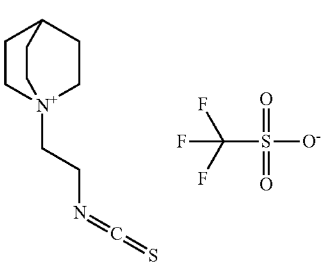 [SMILES: S=C=NCC[N+]12CCC(CC1)CC2 ; O=S(=O)([O-])C(F)(F)F] | 1-(2-Isothiocyanatoethyl)quinuclidinium trifluoromethanesulfonate |

TABLE 1-continued

| ID | * or # | Structure | Compound |
|---|---|---|---|
| 43 | *, # | 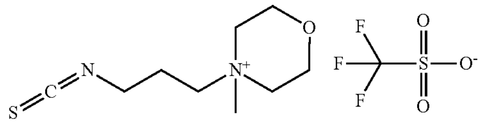 | 4-Methyl-4-(3-isothiocyanatopropyl)morpholinium trifluoromethanesulfonate |
| 44 | *, # | 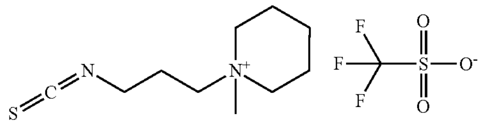 | 1-Methyl-1-(3-isothiocyanatopropyl)piperidinium trifluoromethanesulfonate |
| 45 | *, # | 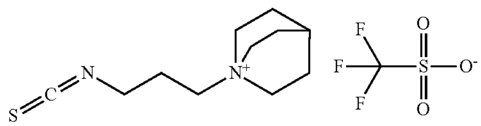 [SMILES: S=C=NCCC[N+]12CCC(CC1)CC2 ; O=S(=O)([O-])C(F)(F)F] | 1-(3-Isothiocyanatopropyl)quinuclidinium trifluoromethanesulfonate |

EXAMPLES

Example 1: Syntheses of Compounds of Formula (I) or Formula (II)

All synthesis procedures were performed at room temperature (RT) and atmospheric pressure unless stated otherwise.

Example 1.1: Synthesis of N,N-Diethyl-2-isothiocyanato-N-methylpropanaminium iodide

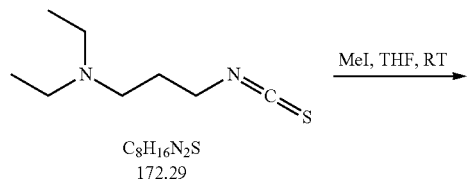

To a solution of 3-isothiocyanato-N,N-dimethylpropanamine (118 mg, 0.385 mmol) in THF (1 mL), add MeI (methyl iodide) (51 μL, 1.2 molar equivalents (eq.)). The mixture was stirred at RT (room temperature) for 24 hrs resulting in two layers. The bottom layer was washed with THF three times (3×) and dried in high vacuum to give 0.189 g (90%) as brown oil. MS-ESI (mass spectrometry electrospray ionization): 186.64 (M-I⁻).

Example 1.2: Synthesis of 3-Isothiocyanato-N,N-diethyl-N-methylpropanaminium iodide

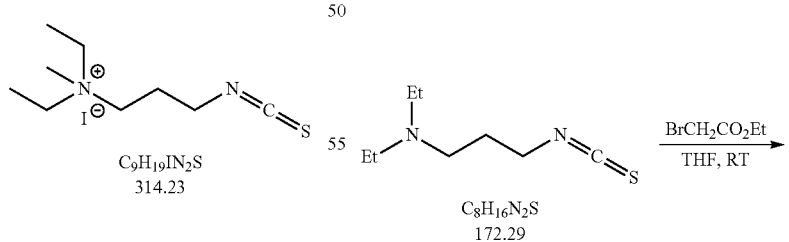

To a solution of 2-Isothiocyanato-N,N-dimethylethanamine (45 mg, 0.261 mmol) in toluene (1 mL) was added MeI (33 μL, 2 eq.). The mixture was stirred at RT for 2 days resulting in two layers with a thick oil on the bottom. The top liquid was decanted, washed with toluene once, ether twice and dried in high vacuum to give 82 mg (quantitative yield) as a brown solid. MS-ESI: 186.50 (M-I⁻).

Example 1.3: Synthesis of N-(Ethoxycarbonylethyl)-3-isothiocyanato-N,N-diethylpropan-1-aminium bromide

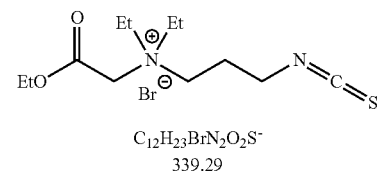

To a solution of 3-isothiocyanato-N,N-diethylpropanamine (91 mg, 0.528 mmol) in THF (0.7 mL) was added ethyl bromoacetate (70 µL, 1.2 eq.). The mixture was stirred at RT for 21 hrs resulting in two layers. The bottom layer was washed with THF (3×) and dried in high vacuum to give 0.045 g (25.1%) as brown oil. MS-ESI: 172.72 (M-CH$_2$CO$_2$Et-Br$^-$), 230.84 (M-Et-Br$^-$), 258.87 (M-Br$^-$).

Example 1.4: Synthesis of N-(Ethoxycarbonylethyl)-2-isothiocyanato-N,N-dimethylethan-1-aminium bromide

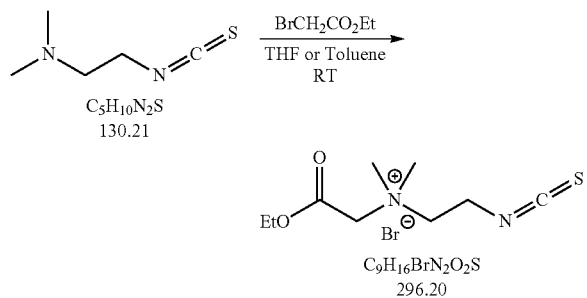

To a solution of 3-isothiocyanato-N,N-dimethylpropanamine (56 mg, 0.431 mmol) in toluene (1 mL) was added ethyl bromoacetate (95 µL, 2 eq.). The mixture was stirred at RT for 18 hrs resulting in two layers. The solid was collected by filtration (very hygroscopic) and dried in high vacuum to give 72 mg (56.2%) as a white solid. MS-ESI: 216.57 (M-B$^-$).

Example 1.5: Synthesis of N-(Ethoxypropyl-2,3-dione)-2-isothiocyanato-N,N-dimethylethan-1-aminium bromide

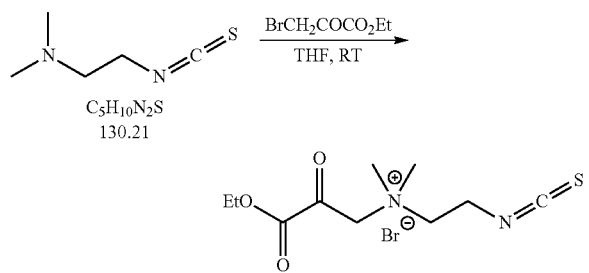

To a solution of 3-isothiocyanato-N,N-dimethylpropanamine (70 mg, 0.538 mmol) in THF (1 mL) was added ethyl bromopyruvate (88 µL, 1.3 eq.). The mixture was stirred at RT for 16 hrs resulting in two layers. The top liquid was decanted and the lower oil layer was washed with THF (3×). The residue was dried in high vacuum to give a solid, which was triturated in EtOH (ethanol). The solid was filtered and dried in high vacuum to give 32 mg (18.3%) as an off-white solid. MS-ESI: 130.31 (M-CH$_2$COCO$_2$Et-Br$^-$), 244.54 (M-Br$^-$).

Example 1.6: Synthesis of N-(Ethoxypropyl-2,3-dione)-3-isothiocyanato-N,N-diethylpropan-1-aminium bromide

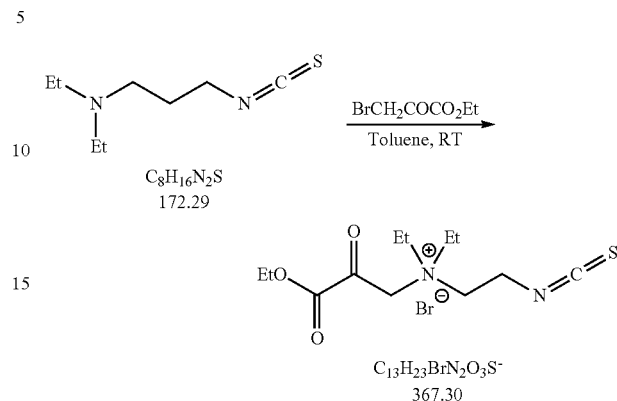

To a solution of 3-isothiocyanato-N,N-dimethylpropanamine (93 mg, 0.540 mmol) in toluene (1 mL) was added ethyl bromopyruvate (82 µL, 1.2 eq.). The mixture was stirred at RT for 24 hrs resulting in two layers. The top liquid was decanted and the lower oil layer was washed with toluene (3×). The residue was dried in high vacuum to give 87 mg (60.3%) a brown oil. MS-ESI: 172.64 (M-CH$_2$COCO$_2$Et-Br$^-$), 258.84 (M-B$^-$).

Example 1.7: Synthesis of N-(2-Bromoethyl)-3-isothiocyanato-N,N-diethylpropan-1-aminium triflate

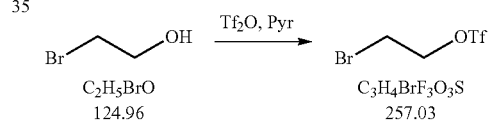

Synthesis of 2-bromoethyl triflate: To a solution of 2-bromoethanol (0.878, 7.026 mmol) in dry DCM (dichloromethane) (10 mL) was added pyridine (0.625 mL, 1.1 eq.) at RT. The solution was cooled to −78° C. and Tf$_2$O (Trifluoromethanesulfonic anhydride) (1.18 mL, 1.1 eq.) was added dropwise. After the addition, the reaction was stirred at RT for 30 min. The mixture was washed with 1M HCl, sated. NaHCO$_3$, dried over anhydrous MgSO$_4$ and evaporated on a rotary evaporator. The residue was distilled using a Kugelrohr apparatus to give 0.892 g (49.6%). $^1$H NMR (300 MHz, CDCl3): δ 4.78 (t, J=6.3 Hz, 2H), 3.64 (t, J=6.3 Hz, 2H).

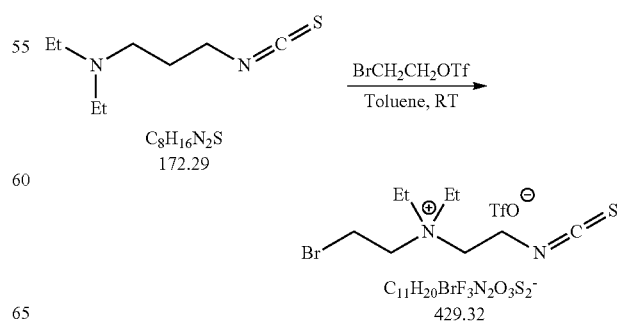

Synthesis of N-(2-Bromoethyl)-3-isothiocyanato-N,N-diethylpropan-1-aminium triflate: To a solution of 3-isothiocyanato-N,N-diethylpropanamine (76 mg, 0.442 mmol) in toluene (1 mL) was added 2-bromoethyl triflate (137 mg, 1.2 eq.). The mixture was stirred at RT for 24 hrs resulting in two layers. The top liquid was decanted and the lower oil layer was dissolved in DCM (0.3 mL) and ether (1 mL) was added slowly with vigorous stirring to precipitate the oil. This process was repeated three times (3×). The residue was dried in high vacuum to give 165 mg (87.2%) as a brown oil. MS-ESI: 172.58 (M-BrCH2CH2-TfO$^-$), 280.70 (M-TfO$^-$).

Example 1.8: Synthesis of N-Cyanomethyl-2-isothiocyanato-N,N-diethylethan-1-aminium bromide

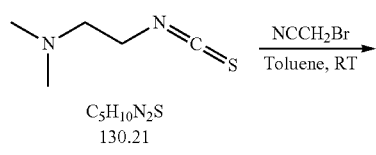

To a solution of 3-isothiocyanato-N,N-dimethylpropanamine (59 mg, 0.343 mmol) in toluene (1 mL) was added bromoacetonitrile (49.4 μL, 1.2 eq.). The mixture was stirred at RT for 2 hrs. The solid was collected by filtration and dried in high vacuum to give 15.3 mg (11.6%) as a white solid. MS-ESI: 169.49 (M-Br−).

Example 1.9: Synthesis of N-Cyanomethyl-3-isothiocyanato-N,N-diethylpropan-1-aminium bromide

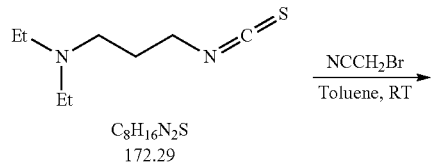

To a solution of 3-isothiocyanato-N,N-dimethylpropanamine (59 mg, 0.343 mmol) in toluene (1 mL) was added bromoacetonitrile (49.4 μL, 1.2 eq.). The mixture was stirred at RT for 18 hrs. The solid was collected by filtration and dried in high vacuum to give 15.3 mg (15.3%) as an off-white solid. MS-ESI: 172.61 (M-CH2CN—Br$^-$), 211.70 (M-Br$^-$).

Example 1.10: Synthesis of N-(2-Phenoxyethyl)-3-isothiocyanato-N,N-diethylpropan-1-aminium triflate

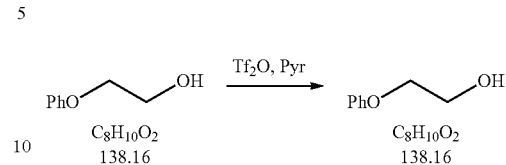

Synthesis of 2-phenoxyethyl triflate: To a solution of 2-phenoxyethanol (0.327 g, 2.367 mmol) in dry DCM (5 mL) was added pyridine (0.25 mL, 1.3 eq.) at RT. The solution was cooled to −78° C. and 667 mg Tf2O was added dropwise. After the addition, the reaction was stirred at RT for 30 min. The mixture was washed with 0.5M HCl, sated. NaHCO3, dried over anhydrous MgSO4 and evaporated on a rotary evaporator to give 0.646 g (quantitative yield). $^1$H NMR (300 MHz, CDCl3): δ 7.35 (dt, J=2.1, 7.8 Hz, 2H), 7.05 (t, J=7.2 Hz, 1H), 6.95 (dt, J=2.1, 7.8 Hz, 2H), 4.86 (dd, J=4.2, 6.0 Hz, 2H), 4.33 (dd, J=4.2, 6.0 Hz, 2H).

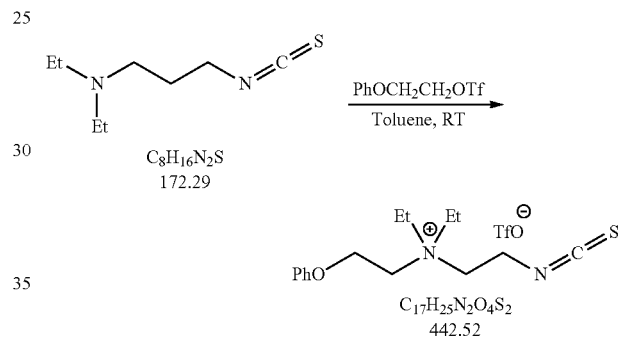

Synthesis of N-(2-Phenoxyethyl)-3-isothiocyanato-N,N-diethylpropan-1-aminium triflate: To a solution of 3-isothiocyanato-N,N-dimethylpropanamine (47.6 mg, 0.276 mmol) in toluene (1 mL) was added 2-phenoxyethyl triflate (89.5 μL, 1.2 eq.). The mixture was stirred at RT for 2 hrs resulting in two layers. The top liquid was decanted and the lower oil layer was dissolved in DCM (0.3 mL) and ether (1 mL) was added slowly with vigorous stirring to precipitate the oil. This process was repeated three times (3×). The residue was dried in high vacuum to give 68.5 mg (56.1%) as a brown oil. MS-ESI: 172.61 (M-PhOCH2CH2-TfO$^-$), 199.61 (M-PhO-TfO$^-$), 292.83 (M-TfO$^-$).

Example 1.11: Synthesis of N-(2-Benzyloxyethyl)-2-isothiocyanato-N,N-dimethylethan-1-aminium triflate

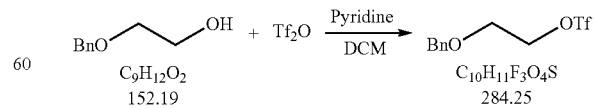

Synthesis of 2-benzyloxy triflate: To a solution of glydicol (0.545 g, 3.582 mmol) in dry DCM (5 mL) was added pyridine (0.38 mL, 1.3 eq.) at RT. The solution was cooled to −78° C. and Tf2O (2.97 mL, 1.2 eq.) was added dropwise.

After the addition, the reaction was stirred at RT for 30 min. The mixture was washed with 0.5M HCl, sated. NaHCO$_3$, dried over anhydrous MgSO$_4$ and evaporated on a rotary evaporator to give 0.989 g (97.1%) as a slightly tan oil, slowly turned to brown color on standing on a bench. The triflate product was stored at −18° C. $^1$H NMR (300 MHz, CDCl3): δ 7.35-7.49 (m, 5H), 4.68 (dd, J=0.6, 4.5 Hz, 2H), 4.63 (s, 2H), 3.81 (dd, J=0.6, 4.5 Hz, 2H).

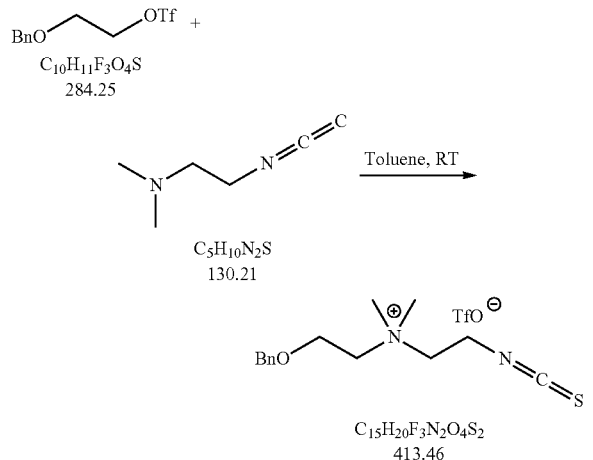

Synthesis of N-(2-Benzyloxyethyl)-2-isothiocyanato-N,N-dimethylethan-1-aminium triflate: To a solution of 2-isothiocyanato-N,N-dimethylethanamine (23.5 mg, 0.181 mmol) in toluene (1 mL) was added 2-benzyloxy triflate (77 mg, 1.5 eq.). The mixture was stirred at RT for 20 hrs resulting in two layers. The top liquid was decanted, washed with toluene once, ether twice and dried in high vacuum to give 75 mg (quantitative yield) as a colorless oil. MS-ESI: 130.34 (M-BnOCH2CH2-TfO$^-$), 264.66 (M-TfO$^-$).

Example 1.12: Synthesis of N-(2-Benzyloxyethyl)-3-isothiocyanato-N,N-diethylpropan-1-aminium triflate

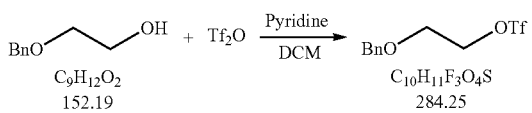

Synthesis of 2-benzyloxy triflate: To a solution of glydicol (0.545 g, 3.582 mmol) in dry DCM (5 mL) was added pyridine (0.38 mL, 1.3 eq.) at RT. The solution was cooled to −78° C. and Tf$_2$O (2.97 mL, 1.2 eq.) was added dropwise. After the addition, the reaction was stirred at RT for 30 min. The mixture was washed with 0.5M HCl, sated. NaHCO$_3$, dried over anhydrous MgSO$_4$ and evaporated on a rotary evaporator to give 0.989 g (97.1%) as a slightly tan oil, slowly turned to brown color on standing on a bench. The triflate product was stored at −18° C. $^1$H NMR (300 MHz, CDCl3): δ 7.35-7.49 (m, 5H), 4.68 (dd, J=0.6, 4.5 Hz, 2H), 4.63 (s, 2H), 3.81 (dd, J=0.6, 4.5 Hz, 2H).

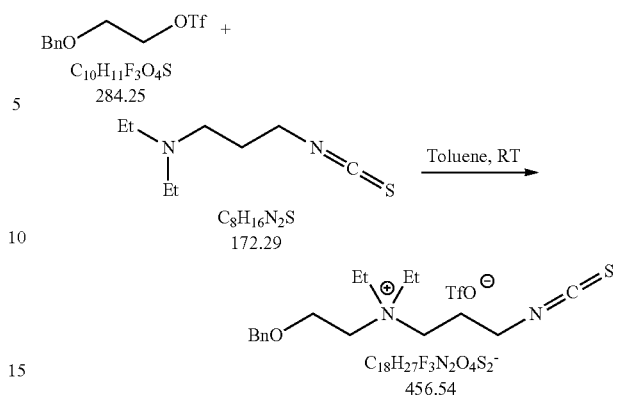

Synthesis of N-(2-Benzyloxyethyl)-3-isothiocyanato-N,N-diethylpropan-1-aminium triflate: To a solution of 3-isothiocyanato-N,N-diethylpropanamine (24 mg, 0.140 mmol) in toluene (1 mL) was added 2-benzyloxyethyl triflate (59 mg, 1.5 eq.). The mixture was stirred at RT for 20 hrs resulting in two layers. The top liquid was decanted, washed with toluene once, ether twice and dried in high vacuum to give 46 mg (72.3%) as a brown oil. MS-ESI: 172.58 (M-BnOCH2CH2-TfO$^-$), 278.81 (M-Et-TfO$^-$), 306.91 (M-TfO$^-$).

Example 1.13: Synthesis of N-(2-Phenoxyethyl)-2-isothiocyanato-N,N-dimethylethan-1-aminium triflate

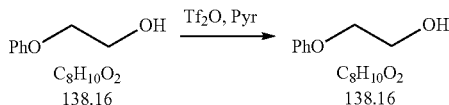

Synthesis of 2-phenoxyethyl triflate: To a solution of 2-phenoxyethanol (0.327 g, 2.367 mmol) in dry DCM (5 mL) was added pyridine (0.25 mL, 1.3 eq.) at RT. The solution was cooled to −78° C. and 667 mg Tf$_2$O was added dropwise. After the addition, the reaction was stirred at RT for 30 min. The mixture was washed with 0.5M HCl, sated. NaHCO$_3$, dried over anhydrous MgSO$_4$ and evaporated on a rotary evaporator to give 0.646 g (quantitative yield). $^1$H NMR (300 MHz, CDCl3): δ 7.35 (dt, J=2.1, 7.8 Hz, 2H), 7.05 (t, J=7.2 Hz, 1H), 6.95 (dt, J=2.1, 7.8 Hz, 2H), 4.86 (dd, J=4.2, 6.0 Hz, 2H), 4.33 (dd, J=4.2, 6.0 Hz, 2H).

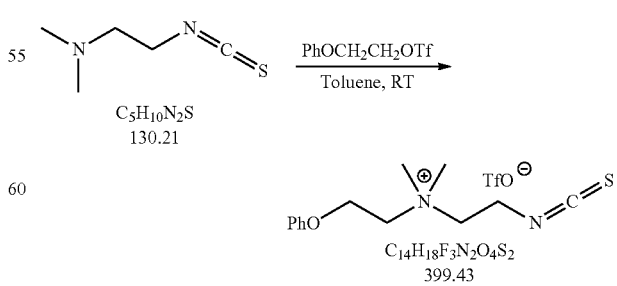

Synthesis of N-(2-Phenoxyethyl)-2-isothiocyanato-N,N-dimethylethan-1-aminium triflate: To a solution of 2-isothiocyanato-N,N-dimethylethanamine (23.9 mg, 0.184 mmol) in toluene (1 mL) was added 2-phenoxyethyl triflate (54.6 mg, 1.1 eq.). The mixture was stirred at RT for 16 hr resulting in a precipitate. The solid was collected by filtration, washed with toluene once, ether twice and dried in high vacuum to give 69.5 mg (94%) as a white solid. MS-ESI: 172.47 (M-Ph-TfO⁻), 250.63 (M-TfO⁻).

Example 1.14: Synthesis of N-(2-Bromoethyl)-2-isothiocyanato-N,N-dimethylethan-1-aminium triflate

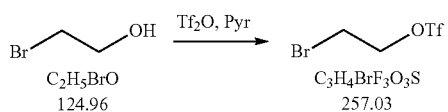

Synthesis of 2-bromoethyl triflate: To a solution of 2-bromoethanol (0.878, 7.026 mmol) in dry DCM (10 mL) was added pyridine (0.625 mL, 1.1 eq.) at RT. The solution was cooled to −78° C. and Tf₂O (1.18 mL, 1.1 eq.) was added dropwise. After the addition, the reaction was stirred at RT for 30 min. The mixture was washed with 1M HCl, sated. NaHCO₃, dried over anhydrous MgSO₄ and evaporated on a rotary evaporator. The residue was distilled using a Kugelrohr apparatus to give 0.892 g (49.6%). ¹H NMR (300 MHz, CDCl3): δ 4.78 (t, J=6.3 Hz, 2H), 3.64 (t, J=6.3 Hz, 2H).

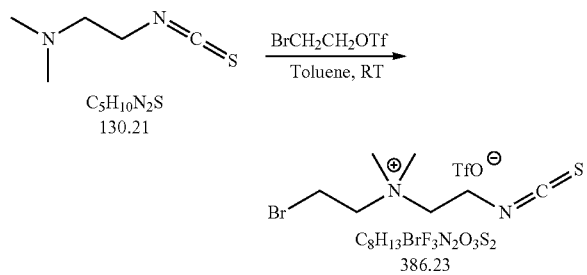

Synthesis of N-(2-Bromoethyl)-2-isothiocyanato-N,N-dimethylethan-1-aminium triflate: To a solution of 2-isothiocyanato-N,N-diethylethanamine (20.3 mg, 0.156 mmol) in toluene (1 mL) was added 2-bromoethyl triflate (40 mg, 1 eq.). The mixture was stirred at RT for 1 day resulting in two layers. The top liquid was decanted and the lower oil layer was washed with toluene and ether. The oil layer was dissolved in DCM:MeOH (9:1) and absorbed to silica gel. The product was purified by dry-loading flash chromatography using DMC:MeOH (9:1) to elute to give 53 mg (88%) as a slightly tan oil. MS-ESI: 238.63 (M-OTs⁻).

Example 1.15: Synthesis of N-(Oxiranylmethyl)-2-isothiocyanato-N,N-dimethylethan-1-aminium triflate

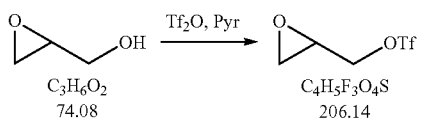

Synthesis of oxiranylmethyl triflate: To a solution of glydicol (1.089, 14.70 mmol) in dry DCM (15 mL) was added pyridine (1.55 mL, 1.3 eq.) at RT. The solution was cooled to −78° C. and Tf₂O (2.97 mL, 1.2 eq.) was added dropwise. After the addition, the reaction was stirred at RT for 30 min. The mixture was washed with 0.5M HCl, sated. NaHCO₃, dried over anhydrous MgSO₄ and evaporated on a rotary evaporator to give 3.00 g as a light brown oil, which was distilled at 33-36° C./0.2 mm Hg. The fraction was collected in a dry ice-acetone bath to give 1.211 g (39.8%) as a colorless oil. ¹H NMR (300 MHz, CDCl3): δ 4.78 (dd, J=3.0, 11.7 Hz, 1H), 4.40 (dd, J=6.3, 11.4 Hz, 1H), 3.37-3.42 (m, 1H), 2.99 (t, J=4.2 Hz, 1H), 2.77 (dd, J=2.4, 4.8 Hz, 1H). ¹⁹F NMR (282 MHz, CDCl3): δ 74.9 (s, 3F).

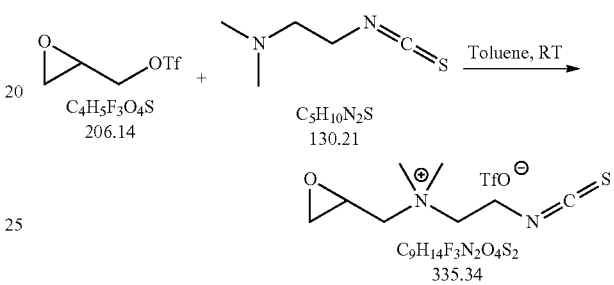

Synthesis of N-(Oxiranylmethyl)-2-isothiocyanato-N,N-dimethylethan-1-aminium triflate: To a solution of 2-isothiocyanato-N,N-dimethylethanamine (21.7 mg, 0.167 mmol) in toluene (1 mL) was added oxiranylmethyl triflate (35 mg, 1 eq.). The mixture was stirred at RT for 1 hr resulting in two layers. The top liquid was decanted, washed with toluene. The lower oil layer was dissolved in DCM (0.3 mL) and ether (1 mL) was added slowly with vigorous stirring to precipitate the oil. The oil was dissolved in DCM:MeOH (9:1) and dry-loaded to a pre-packed silica gel column and eluted with DCM:MeOH (9:1) to give 46 mg (81.7%) as a slightly tan oil after drying at high vacuum. MS-ESI: 186.54 (M-TfO⁻).

Example 1.16: Synthesis of N-(Oxiranylmethyl)-3-isothiocyanato-N,N-diethylpropan-1-aminium triflate

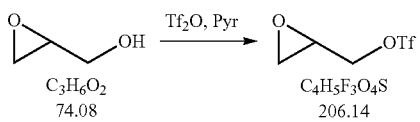 [SMILES: OCC1CO1 ; O=S(=O)(OCC1CO1)C(F)(F)F]

Synthesis of oxiranylmethyl triflate: To a solution of glydicol (1.089, 14.70 mmol) in dry DCM (15 mL) was added pyridine (1.55 mL, 1.3 eq.) at RT. The solution was cooled to −78° C. and Tf₂O (2.97 mL, 1.2 eq.) was added dropwise. After the addition, the reaction was stirred at RT for 30 min. The mixture was washed with 0.5M HCl, sated. NaHCO₃, dried over anhydrous MgSO₄ and evaporated on a rotary evaporator to give 3.00 g as a light brown oil, which was distilled at 33-36° C./0.2 mm Hg. The fraction was collected in a dry ice-acetone bath to give 1.211 g (39.8%) as a colorless oil. ¹H NMR (300 MHz, CDCl3): δ 4.78 (dd, J=3.0, 11.7 Hz, 1H), 4.40 (dd, J=6.3, 11.4 Hz, 1H), 3.37-3.42

(m, 1H), 2.99 (t, J=4.2 Hz, 1H), 2.77 (dd, J=2.4, 4.8 Hz, 1H). ¹⁹F NMR (282 MHz, CDCl3): δ 74.9 (s, 3F).

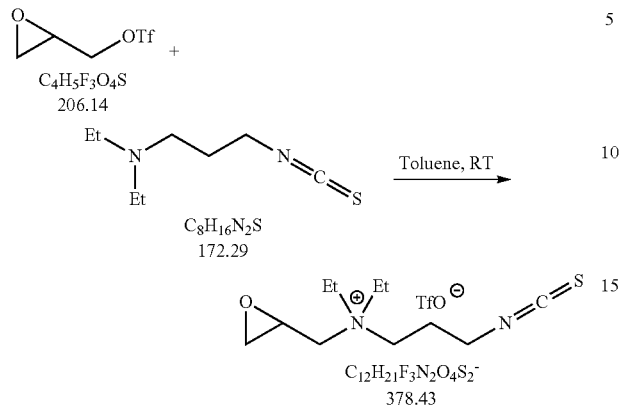

Synthesis of N-(Oxiranylmethyl)-3-isothiocyanato-N,N-diethylpropan-1-aminium triflate: To a solution of 2-isothiocyanato-N,N-dimethylethanamine (48 mg, 0.279 mmol) in toluene (1 mL) was added oxiranylmethyl triflate (58 mg, 1 eq.). The mixture was stirred at RT for 3 hrs resulting in two layers. The top liquid was decanted, washed with toluene. The lower oil layer was dissolved in DCM (0.3 mL) and ether (1 mL) was added slowly with vigorous stirring to precipitate the oil. The oil was dissolved in DCM:MeOH (9:1) and dry-loaded to a pre-packed silica gel column and eluted with DCM:MeOH (9:1) to give 47 mg (61.1%) as a slightly tan oil. MS-ESI: 228.79 (M-TfO⁻).

Example 1.17: Synthesis of N-(2-Methoxyethyl)-2-isothiocyanato-N,N-dimethylethan-1-aminium triflate

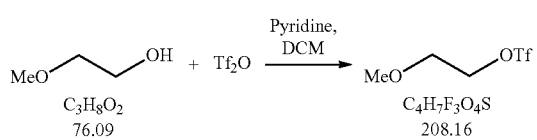 [SMILES: "Tf2O" ; COCCO ; COCCOS(=O)(=O)C(F)(F)F]

Synthesis of 2-methoxyethyl triflate: To a solution of 2-methoxyethanol (0.284 g, 3.732 mmol) in dry DCM (5 mL) was added pyridine (0.332 mL, 1.1 eq.) at RT. The solution was cooled to −70° C. and Tf₂O (0.691 mL, 1.1 eq.) was added dropwise. After the addition, the reaction was stirred at RT for 30 min. The mixture was washed with 0.5M HCl, sated. NaHCO₃, dried over anhydrous MgSO₄ and evaporated on a rotary evaporator. The residue was distilled using a Kugelrohr apparatus at 0.5 Torr with the heating chamber temperature at <45° C. to give 0.521 g (66.8%) as a colorless oil. ¹H NMR (300 MHz, CDCl3): δ 4.65 (t, J=4.2 Hz, 2H), 3.73 (t, J=4.2 Hz, 2H). ¹⁹F NMR (282 MHz, CDCl3): δ 75.2 (s, 3F).

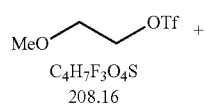

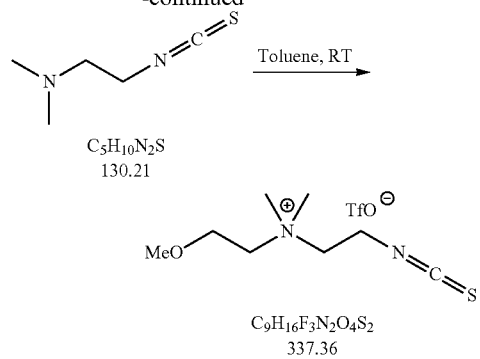

Synthesis of N-(2-Methoxyethyl)-2-isothiocyanato-N,N-dimethylethan-1-aminium triflate: A solution of 2-isothiocyanato-N,N-dimethylethanamine (25 mg, 0.192 mmol) and 2-methoxyethyl triflate (44 mg, 1.1 eq.) in toluene (1 mL) was stirred at RT for 2 hrs resulting in two layers. The top liquid was decanted and the bottom layer was washed with toluene once. The viscous oil was dissolved in DCM (0.3 mL) and ether (1 mL) was added to precipitate the oil. The solvent layer was decanted and this process was repeated twice. The oil was dried in high vacuum to give 42 mg (64.5%) as a colorless oil. MS-ESI: 130.41 (M-MeOCH2CH2-TfO⁻), 188.54 (M-TfO⁻).

Example 1.18: Synthesis of N-(2-Methoxyethyl)-3-isothiocyanato-N,N-diethylpropan-1-aminium triflate

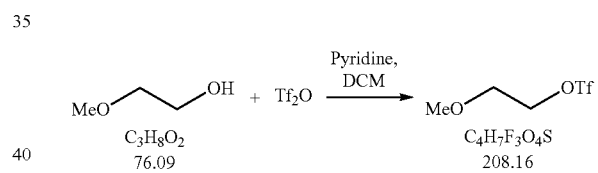

Synthesis of 2-methoxyethyl triflate: To a solution of 2-methoxyethanol (0.284 g, 3.732 mmol) in dry DCM (5 mL) was added pyridine (0.332 mL, 1.1 eq.) at RT. The solution was cooled to −70° C. and Tf₂O (0.691 mL, 1.1 eq.) was added dropwise. After the addition, the reaction was stirred at RT for 30 min. The mixture was washed with 0.5M HCl, sated. NaHCO₃, dried over anhydrous MgSO₄ and evaporated on a rotary evaporator. The residue was distilled using a Kugelrohr apparatus at 0.5 Torr with the heating chamber temperature at <45° C. to give 0.521 g (66.8%) as a colorless oil. ¹H NMR (300 MHz, CDCl3): δ 4.65 (t, J=4.2 Hz, 2H), 3.73 (t, J=4.2 Hz, 2H). ¹⁹F NMR (282 MHz, CDCl3): δ 75.2 (s, 3F).

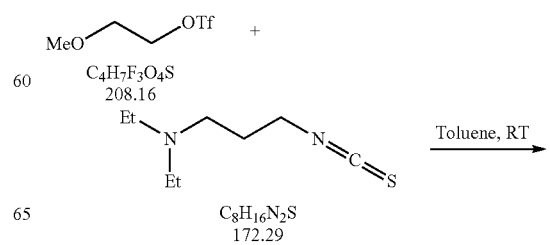

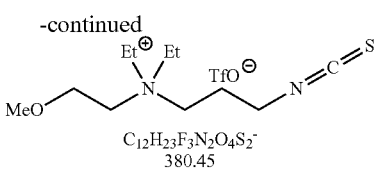

Synthesis of N-(2-Methoxyethyl)-3-isothiocyanato-N,N-diethylpropan-1-aminium triflate: A solution of 3-isothiocyanato-N,N-diethylpropanamine (27 mg, 0.157 mmol) and 2-methoxyethyl triflate (36 mg, 1.1 eq.) in toluene (1 mL) was stirred at RT for 3 hrs resulting in two layers. The top liquid was decanted and the bottom layer was washed with toluene once. The viscous oil was dissolved in DCM (0.3 mL) and ether (1 mL) was added to precipitate the oil. The solvent layer was decanted and this process was repeated twice. The oil was dried in high vacuum to give 34 mg (56.8%) as yellow oil. MS-ESI: 172.61 (M-MeOCH2CH2-TfO$^-$), 230.73 (M-TfO$^-$).

Example 1.19: Synthesis of N-(2-Ethoxyethyl)-2-isothiocyanato-N,N-dimethylethan-1-aminium triflate

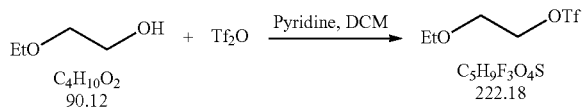 [SMILES: "Tf2O" ; CCOCCO ; CCOCCOS(=O)(=O)C(F)(F)F]

Synthesis of 2-methoxyethyl triflate: To a solution of 2-ethoxyethanol (0.582 g, 6.458 mmol) in dry DCM (10 mL) was added pyridine (0.63 mL, 1.2 eq.) at RT. The solution was cooled to −70° C. and Tf$_2$O (1.19 mL, 1.1 eq.) was added dropwise. After the addition, the reaction was stirred at RT for 30 min. The mixture was washed with 0.5M HCl, sated. NaHCO$_3$, dried over anhydrous MgSO$_4$ and evaporated on a rotary evaporator. The residue was distilled using a Kugelrohr apparatus at 0.4 Torr with the heating chamber temperature at <55° C. to give 1.125 g (78.1%) as a colorless oil. $^1$H NMR (300 MHz, CDCl3): δ 4.65 (t, J=4.5 Hz, 2H), 3.77 (t, J=4.5 Hz, 2H), 3.59 (q, J=6.6 Hz, 2H), 1.25 (t, J=6.6 Hz, 2H). $^{19}$F NMR (282 MHz, CDCl3): δ 75.1 (s, 3F).

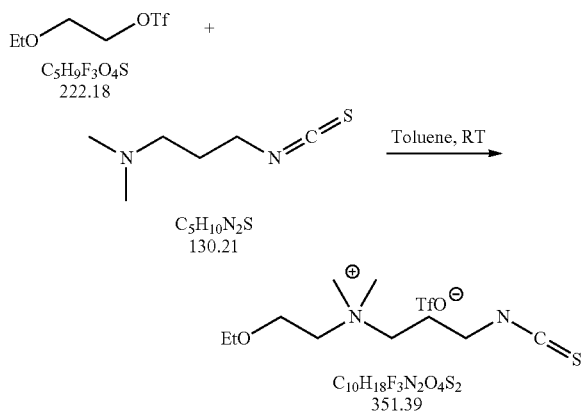

Synthesis of N-(2-Ethoxyethyl)-2-isothiocyanato-N,N-dimethylethan-1-aminium triflate: A solution of 2-isothiocyanato-N,N-dimethylethanamine (31 mg, 0.238 mmol) and 2-methoxyethyl triflate (58.5 mg, 1.1 eq.) in toluene (1 mL) was stirred at RT for 2 hrs resulting in two layers. The top liquid was decanted and the bottom layer was washed with toluene once. The viscous oil was dissolved in DCM (0.3 mL) and ether (1 mL) was added to precipitate the oil. The solvent layer was decanted and this process was repeated twice. The oil was dried in high vacuum to give 70 mg (83.3%) as a colorless oil. MS-ESI: 202.61 (M-TfO$^-$).

Example 1.20: Synthesis of N-(2-Ethoxyethyl)-3-isothiocyanato-N,N-diethylpropan-1-aminium triflate

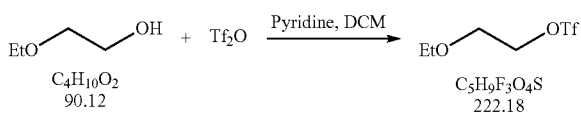 [SMILES: "Tf2O" ; CCOCCO ; CCOCCOS(=O)(=O)C(F)(F)F]

Synthesis of 2-methoxyethyl triflate: To a solution of 2-ethoxyethanol (0.582 g, 6.458 mmol) in dry DCM (10 mL) was added pyridine (0.63 mL, 1.2 eq.) at RT. The solution was cooled to −70° C. and Tf$_2$O (1.19 mL, 1.1 eq.) was added dropwise. After the addition, the reaction was stirred at RT for 30 min. The mixture was washed with 0.5M HCl, sated. NaHCO$_3$, dried over anhydrous MgSO$_4$ and evaporated on a rotary evaporator. The residue was distilled using a Kugelrohr apparatus at 0.4 Torr with the heating chamber temperature at <55° C. to give 1.125 g (78.1%) as a colorless oil. $^1$H NMR (300 MHz, CDCl3): δ 4.65 (t, J=4.5 Hz, 2H), 3.77 (t, J=4.5 Hz, 2H), 3.59 (q, J=6.6 Hz, 2H), 1.25 (t, J=6.6 Hz, 2H). $^{19}$F NMR (282 MHz, CDCl3): δ 75.1 (s, 3F).

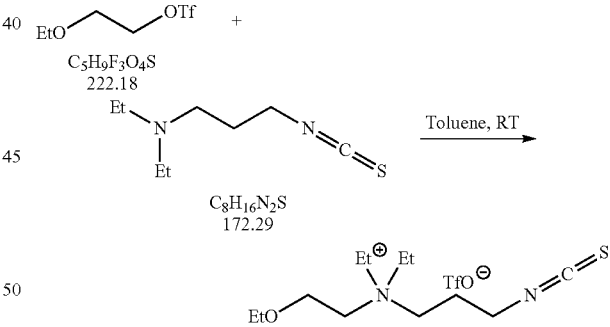

Synthesis of N-(2-Ethoxyethyl)-3-isothiocyanato-N,N-diethylpropan-1-aminium triflate: A solution of 3-isothiocyanato-N,N-diethylpropanamine (28.5 mg, 0.166 mmol) and 2-methoxyethyl triflate (40.6 mg, 1.1 eq.) in toluene (1 mL) was stirred at RT for 3 hrs resulting in two layers. The top liquid was decanted and the bottom layer was washed with toluene once. The viscous oil was dissolved in DCM (0.3 mL) and ether (1 mL) was added to precipitate the oil. The solvent layer was decanted and this process was repeated twice. The oil was dried in high vacuum to give 31.2 mg (47.5%) as yellow oil. MS-ESI: 172.52 (M-EtOCH2CH2-TfO$^-$), 244.72 (M-TfO$^-$).

Example 1.21: Synthesis of N-(3-Methoxypropyl)-2-isothiocyanato-N,N-dimethylethan-1-aminium triflate

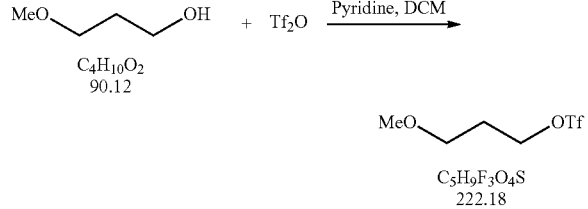

Synthesis of 3-methoxypropyl triflate: To a solution of 3-mthoxypropanol (0.528 g, 5.829 mmol) in dry DCM (8 mL) was added pyridine (0.52 mL, 1.1 eq.) at RT. The solution was cooled to −70° C. and Tf$_2$O (1.08 mL, 1.1 eq.) was added dropwise. After the addition, the reaction was stirred at RT for 30 min. The mixture was washed with 0.5M HCl, sated. NaHCO$_3$, dried over anhydrous MgSO$_4$ and evaporated on a rotary evaporator. The residue was distilled using a Kugelrohr apparatus at 0.5 Torr with the heating chamber temperature at <50° C. to give 0.832 g (63.7%) as a colorless oil. $^1$H NMR (300 MHz, CDCl3): δ 4.68 (t, J=6.6 Hz, 2H), 3.51 (t, J=6.0 Hz, 2H), 3.37 (s, 3H), 2.09 (quint, J=6.0 Hz, 2H). $^{19}$F NMR (282 MHz, CDCl3): δ 75.3 (s, 3F).

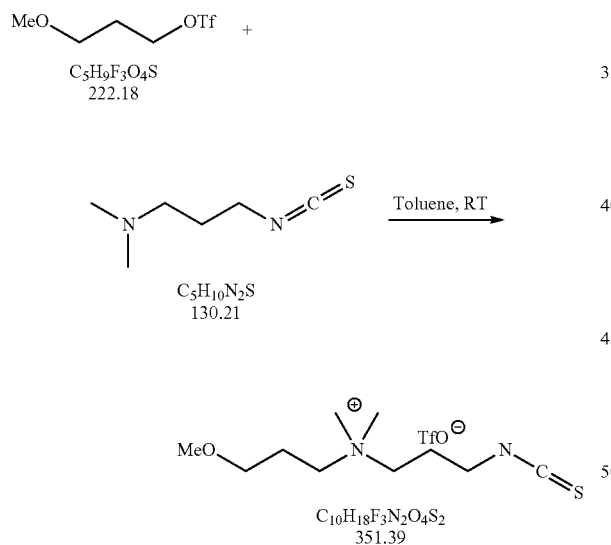

Synthesis of N-(3-Methoxypropyl)-2-isothiocyanato-N,N-dimethylethan-1-aminium triflate: A solution of 2-isothiocyanato-N,N-dimethylethanamine (27.7 mg, 0.213 mmol) and 3-methoxypropyl triflate (52 mg, 1.1 eq.) in toluene (1 mL) was stirred at RT for 2 hrs resulting in two layers. The top liquid was decanted and the bottom layer was washed with toluene once. The viscous oil was dissolved in DCM (0.3 mL) and ether (1 mL) was added to precipitate the oil. The solvent layer was decanted and this process was repeated twice. The oil was dried in high vacuum to give 62.5 mg (83.3%) as a colorless oil. MS-ESI: 202.64 (M-TfO$^-$).

Example 1.22: Synthesis of N-(3-Methoxyethyl)-3-isothiocyanato-N,N-diethylpropan-1-aminium triflate

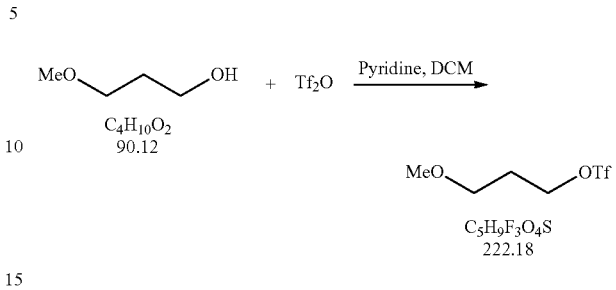

Synthesis of 3-methoxypropyl triflate: To a solution of 3-mthoxypropanol (0.528 g, 5.829 mmol) in dry DCM (8 mL) was added pyridine (0.52 mL, 1.1 eq.) at RT. The solution was cooled to −70° C. and Tf$_2$O (1.08 mL, 1.1 eq.) was added dropwise. After the addition, the reaction was stirred at RT for 30 min. The mixture was washed with 0.5M HCl, sated. NaHCO$_3$, dried over anhydrous MgSO$_4$ and evaporated on a rotary evaporator. The residue was distilled using a Kugelrohr apparatus at 0.5 Torr with the heating chamber temperature at <50° C. to give 0.832 g (63.7%) as a colorless oil. $^1$H NMR (300 MHz, CDCl3): δ 4.68 (t, J=6.6 Hz, 2H), 3.51 (t, J=6.0 Hz, 2H), 3.37 (s, 3H), 2.09 (quint, J=6.0 Hz, 2H). $^{19}$F NMR (282 MHz, CDCl3): δ 75.3 (s, 3F).

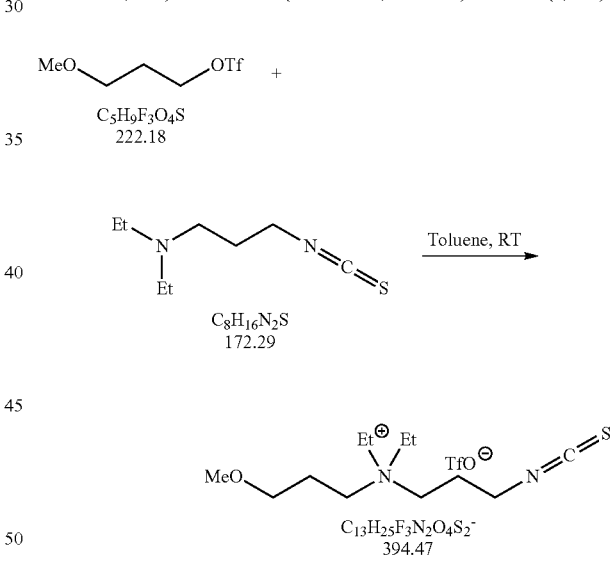

Synthesis of N-(3-Methoxyethyl)-3-isothiocyanato-N,N-diethylpropan-1-aminium triflate: A solution of 3-isothiocyanato-N,N-diethylpropanamine (31.5 mg, 0.183 mmol) and 3-methoxypropyl triflate (45 mg, 1.1 eq.) in toluene (1 mL) was stirred at RT for 3 hrs resulting in two layers. The top liquid was decanted and the bottom layer was washed with toluene once. The viscous oil was dissolved in DCM (0.3 mL) and ether (1 mL) was added to precipitate the oil. The solvent layer was decanted and this process was repeated twice. The oil was dried in high vacuum to give 49.3 mg (68.4%) as yellow oil. MS-ESI: 172.53 (M-EtOCH2CH2-TfO$^-$), 244.71 (M-TfO$^-$).

Example 1.23: Synthesis of N-(2-Chloroethyl)-2-isothiocyanato-N,N-dimethylethan-1-aminium triflate

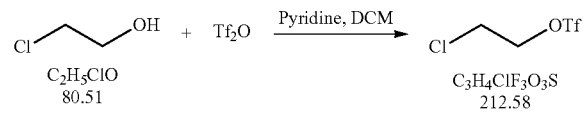

C₂H₅ClO
80.51

C₃H₄ClF₃O₃S
212.58

Synthesis of 2-chloroethyl triflate: To a solution of 2-chloroethanol (0.518 g, 6.433 mmol) in dry DCM (8 mL) was added pyridine (0.57 mL, 1.1 eq.) at RT. The solution was cooled to −70° C. and Tf₂O (1.19 mL, 1.1 eq.) was added dropwise. After the addition, the reaction was stirred at RT for 30 min. The mixture was washed with 0.5M HCl, sated. NaHCO₃, dried over anhydrous MgSO₄ and evaporated on a rotary evaporator. The residue was distilled using a Kugelrohr apparatus at 1 Torr with the heating chamber temperature at <50° C. to give 0.85 g (62.2%) as a colorless oil. $^1$H NMR (300 MHz, CDCl3): δ 4.73 (t, J=5.7 Hz, 2H), 3.83 (t, J=6.0 Hz, 2H). $^{19}$F NMR (282 MHz, CDCl3): δ 74.9 (s, 3F).

C₃H₄ClF₃O₃S
212.58

C₅H₁₀N₂S
130.21

C₈H₁₃ClF₃N₂O₃S₂
341.78

Synthesis of N-(2-Chloroethyl)-2-isothiocyanato-N,N-dimethylethan-1-aminium triflate: A solution of 2-isothiocyanato-N,N-dimethylethanamine (32.6 mg, 0.251 mmol) and 2-chloroethyl triflate (58.6 mg, 1.1 eq.) in toluene (1 mL) was stirred at RT for 2 hrs resulting in two layers. The top liquid was decanted and the bottom layer was washed with toluene once. The viscous oil was dissolved in DCM (0.3 mL) and ether (1 mL) was added to precipitate the oil. The solvent layer was decanted and this process was repeated twice. The oil was dried in high vacuum to give 65.2 mg (75.8%) as a colorless oil. MS-ESI: 192.48 (M-TfO⁻).

Example 1.24: Synthesis of N-(3-Chloropropyl)-2-isothiocyanato-N,N-dimethylethan-1-aminium triflate C₃H₇ClO
94.54

C₄H₆ClF₃O₃S
226.60

Synthesis of 3-Chloropropyl triflate: To a solution of 2-chloroethanol (0.653 g, 6.907 mmol) in dry DCM (8 mL) was added pyridine (0.614 mL, 1.1 eq.) at RT. The solution was cooled to −70° C. and Tf₂O (1.28 mL, 1.1 eq.) was added dropwise. After the addition, the reaction was stirred at RT for 30 min. The mixture was washed with 0.5M HCl, sated. NaHCO₃, dried over anhydrous MgSO₄ and evaporated on a rotary evaporator. The residue was distilled using a Kugelrohr apparatus at 0.3 Torr with the heating chamber temperature at <50° C. to give 0.1.02 g (64.9%) as a colorless oil. $^1$H NMR (300 MHz, CDCl3): δ 4.75 (t, J=6.0 Hz, 2H), 3.71 (t, J=6.0 Hz, 2H), 2.31 (quint, J=6.0 Hz, 2H). $^{19}$F NMR (282 MHz, CDCl3): δ 75.0 (s, 3F).

C₄H₆ClF₃O₃S
226.60

C₅H₁₀N₂S
130.21

C₉H₁₅ClF₃N₂O₃S₂
355.81

Synthesis of N-(3-Chloropropyl)-2-isothiocyanato-N,N-dimethylethan-1-aminium triflate: A solution of 3-isothiocyanato-N,N-diethylpropanamine (24.6 mg, 0.189 mmol) and 3-chloropropyl triflate (47.4 mg, 1.1 eq.) in toluene (1 mL) was stirred at RT for 4 hrs resulting in two layers. The top liquid was decanted and the bottom layer was washed with toluene once. The viscous oil was dissolved in DCM (0.3 mL) and ether (1 mL) was added to precipitate the oil. The solvent layer was decanted and this process was repeated twice. The oil was dried in high vacuum to give 67.8 mg (100%) as colorless oil. MS-ESI: 206.55 (M-TfO⁻).

Example 1.25: Synthesis of N-(2-Chloroethyl)-3-isothiocyanato-N,N-diethylpropan-1-aminium triflate C₂H₅ClO
80.51

C₃H₄ClF₃O₃S
212.58

Synthesis of 2-chloroethyl triflate: To a solution of 2-chloroethanol (0.518 g, 6.433 mmol) in dry DCM (8 mL) was added pyridine (0.57 mL, 1.1 eq.) at RT. The solution was cooled to −70° C. and Tf₂O (1.19 mL, 1.1 eq.) was added dropwise. After the addition, the reaction was stirred at RT for 30 min. The mixture was washed with 0.5M HCl, sated. NaHCO₃, dried over anhydrous MgSO₄ and evaporated on a rotary evaporator. The residue was distilled using a Kugelrohr apparatus at 1 Torr with the heating chamber temperature at <50° C. to give 0.85 g (62.2%) as a colorless oil. ¹H NMR (300 MHz, CDCl3): δ 4.73 (t, J=5.7 Hz, 2H), 3.83 (t, J=6.0 Hz, 2H). ¹⁹F NMR (282 MHz, CDCl3): δ 74.9 (s, 3F).

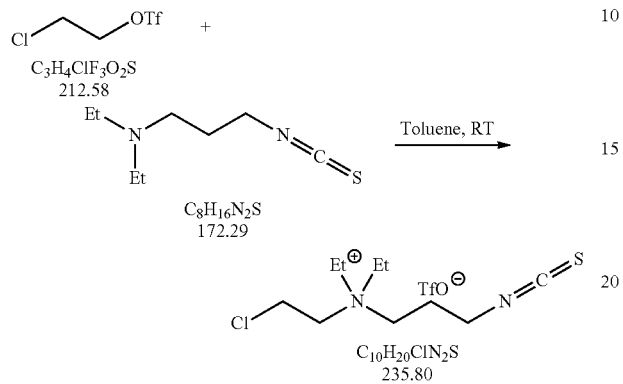

Synthesis of N-(2-Chloroethyl)-3-isothiocyanato-N,N-diethylpropan-1-aminium triflate: A solution of 3-isothiocyanato-N,N-diethylpropanamine (26.6 mg, 0.155 mmol) and 2-chloroethyl triflate (36.2 mg, 1.1 eq.) in toluene (1 mL) was stirred at RT for 3 hrs resulting in two layers. The top liquid was decanted and the bottom layer was washed with toluene once. The viscous oil was dissolved in DCM (0.3 mL) and ether (1 mL) was added to precipitate the oil. The solvent layer was decanted and this process was repeated twice. The oil was dried in high vacuum to give 37 mg (62.1%) as yellow oil. MS-ESI: 172.43 (M-ClCH2CH2-TfO⁻), 234.54 (M-TfO⁻).

Example 1.26: Synthesis of N-(3-Chloropropyl)-3-isothiocyanato-N,N-diethylpropan-1-aminium triflate

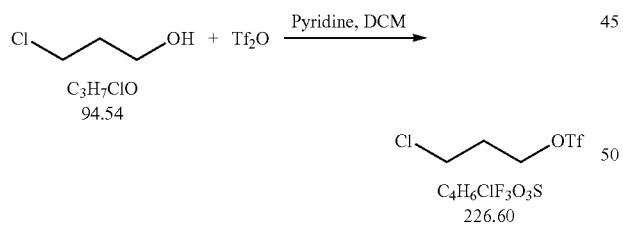

Synthesis of 3-Chloropropyl triflate: To a solution of 2-chloroethanol (0.653 g, 6.907 mmol) in dry DCM (8 mL) was added pyridine (0.614 mL, 1.1 eq.) at RT. The solution was cooled to −70° C. and Tf₂O (1.28 mL, 1.1 eq.) was added dropwise. After the addition, the reaction was stirred at RT for 30 min. The mixture was washed with 0.5M HCl, sated. NaHCO₃, dried over anhydrous MgSO₄ and evaporated on a rotary evaporator. The residue was distilled using a Kugelrohr apparatus at 0.3 Torr with the heating chamber temperature at <50° C. to give 0.1.02 g (64.9%) as a colorless oil. ¹H NMR (300 MHz, CDCl3): δ 4.75 (t, J=6.0 Hz, 2H), 3.71 (t, J=6.0 Hz, 2H), 2.31 (quint, J=6.0 Hz, 2H). ¹⁹F NMR (282 MHz, CDCl3): δ 75.0 (s, 3F).

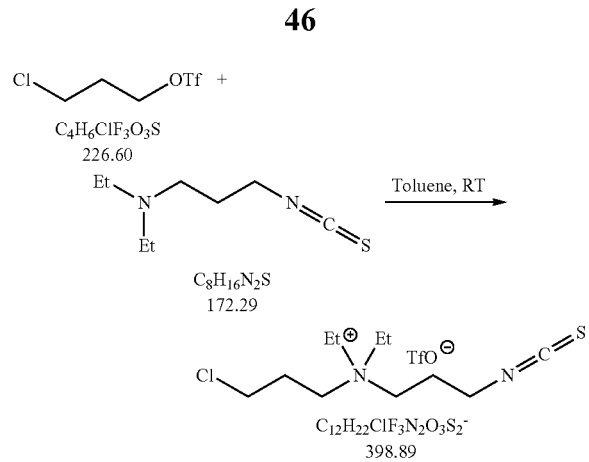

Synthesis of N-(3-Chloropropyl)-3-isothiocyanato-N,N-diethylpropan-1-aminium triflate: A solution of 3-isothiocyanato-N,N-diethylpropanamine (26.5 mg, 0.154 mmol) and 3-chloropropyl triflate (38.6 mg, 1.1 eq.) in toluene (1 mL) was stirred at RT for 4 hrs resulting in two layers. The top liquid was decanted and the bottom layer was washed with toluene once. The viscous oil was dissolved in DCM (0.3 mL) and ether (1 mL) was added to precipitate the oil. The solvent layer was decanted and this process was repeated twice. The oil was dried in high vacuum to give 36 mg (58.8%) as colorless oil. MS-ESI: 172.49 (M-ClCH2CH2-TfO⁻), 248.65 (M-TfO⁻).

Example 1.27: Synthesis of N-(2-Fluoroethyl)-3-isothiocyanato-N,N-diethylpropan-1-aminium triflate

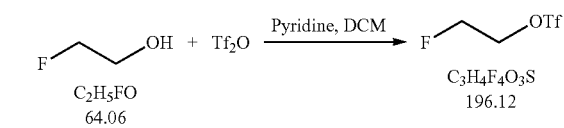

Synthesis of 2-fluoroethyl triflate: To a solution of 2-fluoroethanol (0.401 g, 6.260 mmol) in dry DCM (8 mL) was added pyridine (0.56 mL, 1.1 eq.) at RT. The solution was cooled to −70° C. and Tf₂O (1.16 mL, 1.1 eq.) was added dropwise. After the addition, the reaction was stirred at RT for 30 min. The mixture was washed with 0.5M HCl, sated. NaHCO₃, dried over anhydrous MgSO₄ and evaporated on a rotary evaporator. The residue was distilled using a Kugelrohr apparatus at 2 Torr with the heating chamber temperature at <40° C. to give 0.256 g (20.9%) as a colorless oil. ¹H NMR (300 MHz, CDCl3): δ 4.76-4.83 (m, 2H), 4.63-4.72 (m, 2H). ¹⁹F NMR (282 MHz, CDCl3): δ 50.0 (s, 3F), 4.3 (m, 1F).

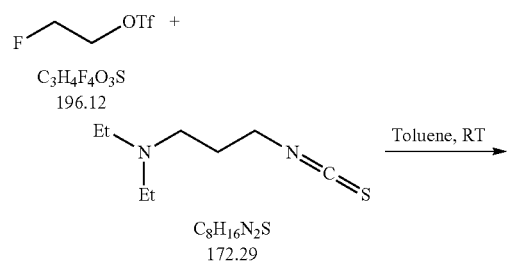

-continued

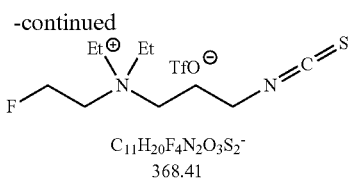

C₁₁H₂₀F₄N₂O₃S₂⁻
368.41

Synthesis of N-(2-Fluoroethyl)-3-isothiocyanato-N,N-diethylpropan-1-aminium triflate: A solution of 3-isothiocyanato-N,N-diethylpropanamine (34 mg, 0.198 mmol) and 2-fluoroethyl triflate (43 mg, 1.1 eq.) in toluene (1 mL) was stirred at RT for 3 hrs resulting in two layers. The top liquid was decanted and the bottom layer was washed with toluene once. The viscous oil was dissolved in DCM (0.3 mL) and ether (1 mL) was added to precipitate the oil. The solvent layer was decanted and this process was repeated twice. The oil was dried in high vacuum to give 36.6 mg (50.1%) as yellow oil. MS-ESI: 172.43 (M-FCH2CH2-TfO⁻), 218.86 (M-TfO⁻).

Example 1.28: Synthesis of 1-(2-Isothiocyanatoethyl)pyridin-1-ium bromide

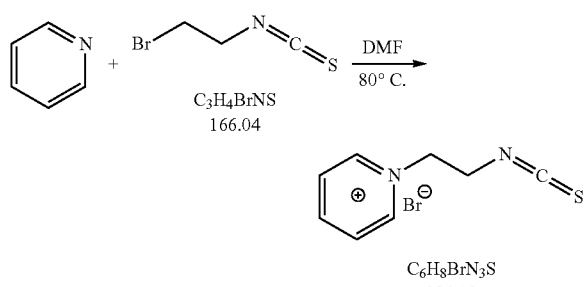

A solution of 2-isothiocyanatoethyl bromide (44 mg, 0.265 mmol) and pyridine (43 mg, 2.0 eq.) in DMF (dimethylformamide) (1 mL) was heated at 80° C. for 2 hrs resulting in a precipitate. The top solvent layer was decanted and the precipitate was washed with DMF (0.5 mL) once. The oil was dissolved in DCM:MeOH (9:1, 0.3 mL) and precipitated in ether (1 mL). This process was repeated twice. The oil was dried in high vacuum to give 51.7 mg (32.5%) as a tan solid. MS-ESI: 79.52 (M-CH2CH2NCS—Br—), 164.55 (M-Br—).

Example 1.29: Synthesis of 1-(2-Isothiocyanatoethyl)-3-hydroxypyridinium bromide

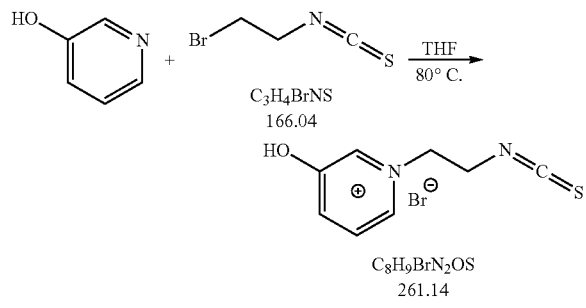

A solution of 2-isothiocyanatoethyl bromide (49 mg, 0.295 mmol) and 3-hydroxypyridine (30.9 mg, 1.1 eq.) in THF (1 mL) was heated at 80° C. for 4 days. The top solvent layer was decanted and the precipitate was washed with THF (2×0.5 mL). The combined solvent was evaporated in reduced pressure. The residue was dissolved in DCM (0.3 mL) and precipitated in ether (1 mL). This process was repeated twice and the oil was dried in high vacuum to give 26 mg (33.8%) as tan oil. MS-ESI: 180.57 (M-B⁻).

Example 1.30: Synthesis of 1-(2-Isothiocyanato-ethyl)-(2-hydroxymethyl)pyridinium triflate

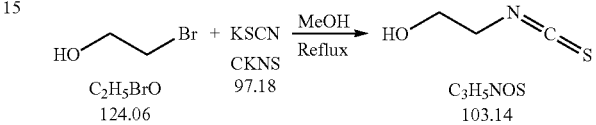

Synthesis of 2-Isothiocyanatoethanol: To a solution of potassium thiocyanate (1.159 g, 11.948 mmol) in MeOH (10 mL) was added 2-bromoethanol (1.971 g, 1 eq.) at RT. The solution was heated at reflux for 24 hrs. A white precipitate was formed during the heating. After cooing, the precipitate was removed by filtration and the filtrate was evaporated. The residue was analyzed by ¹H NMR showing about 5:1 ratio of the product to starting material. The oil was distilled using a Kugelrohr apparatus at 0.3 Torr with the heating chamber temperature at <50° C. The undistilled residue gave 1.189 g (96.5%) as a light tan oil. ¹H NMR (300 MHz, CDCl3): δ 4.03 (t, J=6.0 HZ, 2H), 3.16 (t, J=6.0 Hz, 2H).

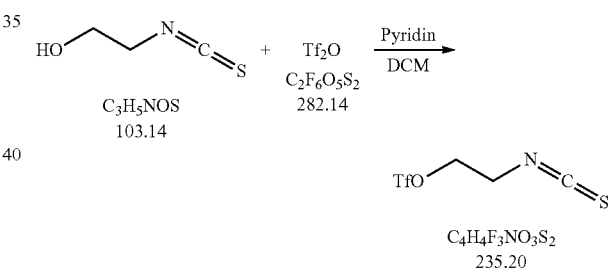

Synthesis of 2-Isothiocyanatoethyl trifluoromethanesulfonate: To a solution of 2-isothiocyanatoethanol (1.189 g, 11.544 mmol) and pyridine (1.03 mL, 1.1 eq.) in DCM (10 mL) was added Tf₂O (2.146 mL, 1.1 eq.) dropwise at −70° C. After the addition, the mixture was stirred at −70° C. for 10 min and RT for 30 min. The mixture was washed with 0.5N HCl, saturated NaHCO₃, dried over anhydrous MgSO₄ and evaporated. The residue was distilled using a Kugelrohr apparatus at 0.05 Torr with the heating chamber temperature at <85° C. to give 1.532 g (56.4%) as a colorless oil. ¹H NMR (300 MHz, CDCl3): δ 4.82 (t, J=6.0 HZ, 2H), 3.37 (t, J=6.0 Hz, 2H). ¹⁹F NMR (282 MHz, CDCl3): δ 74.6 (s, 3F).

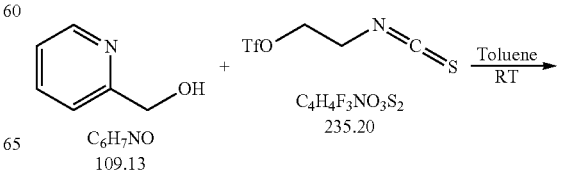

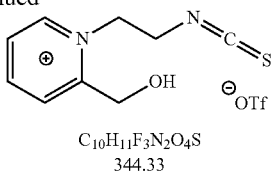

C₁₀H₁₁F₃N₂O₄S
344.33

Synthesis of 1-(2-Isothiocyanatoethyl)-(2-hydroxymethyl)pyridinium triflate: A solution of 2-Isothiocyanatoethyl trifluoromethanesulfonate (51.1 mg, 0.217 mmol) and 2-hydroxymethylpyridine (23.7 mg, 1 eq.) in toluene (1 mL) was stirred at RT for 4 hrs resulting in a precipitate. The top solvent layer was decanted and the precipitate was washed with toluene once and ether three times. The solid was dried in high vacuum to give 55.5 mg (74.3%) as a greenish solid. MS-ESI: 109.60 (M-CH2CH2NCS—OTf⁻), 135.57 (M-HNCS—OTf⁻), 194.68 (M-OTf⁻).

Example 1.31: Synthesis of 2-(hydroxymethyl)-1-(3-isothiocyanatopropyl)pyridin-1-ium trifluoromethanesulfonate

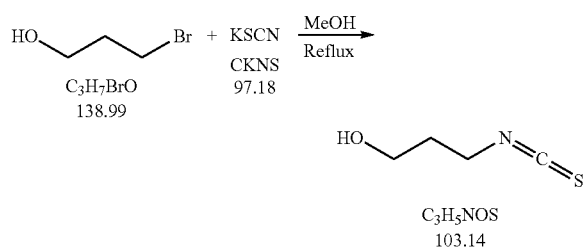

Synthesis of 3-isothiocyanatopropanol: To a solution of potassium thiocyanate (1.074 g, 11.052 mmol, 1.2 eq.) in MeOH (10 mL) was added 3-bromopropanol (1.280 g, 9.209 mmol) at RT. The solution was heated at reflux for 20 hrs. A white precipitate was formed during the heating. After cooing, the precipitate was removed by filtration, the residue was suspended in DCM (10 mL), the white solid was removed by filtration and the filtrate was evaporated. The residue was distilled using a Kugelrohr apparatus at 0.05 Torr with the heating chamber temperature at <40° C. The undistilled residue gave 1.063 g (84.6%) as a nearly clear oil. 1H NMR (300 MHz, CDCl3): δ 3.85 (t, J=6.0 HZ, 2H), 3.14 (t, J=6.6 Hz, 2H), 2.10 (quint, J=6.0 Hz, 2H).

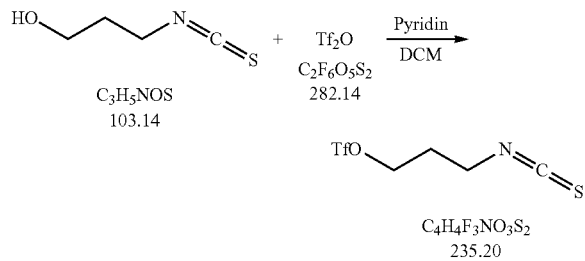

Synthesis of 3-isothiocyanatopropyl triflate: To a solution of 3-isothiocyanatopropanol (1.063 g, 90.85 mmol) and pyridine (0.81 mL, 1.1 eq.) in DCM (10 mL) was added Tf₂O (1.68 g, 1.1 eq.) dropwise at −70° C. After the addition, the mixture was stirred at −70° C. for 10 min and RT for 30 min. The mixture was washed with 0.5N HCl, saturated NaHCO₃, dried over anhydrous MgSO₄ and evaporated. The residue was distilled using a Kugelrohr apparatus at 0.06 Torr with the heating chamber temperature at <85° C. to give 0.590 g (26.1%) as a colorless oil. ¹H NMR (300 MHz, CDCl3): δ 4.71 (t, J=6.0 HZ, 2H), 3.11 (t, J=6.9 Hz, 2H), 2.39 (quint. J=6.3 Hz, 2H). ¹⁹F NMR (282 MHz, CDCl3): δ 74.9 (s, 3F).

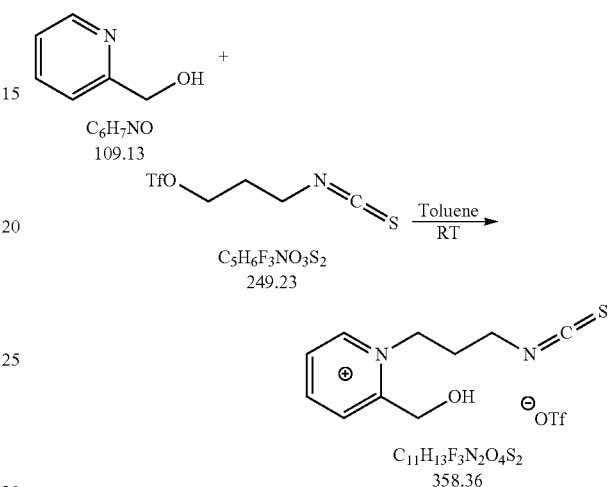

Synthesis of 2-(hydroxymethyl)-1-(3-isothiocyanatopropyl)pyridin-1-ium trifluoromethanesulfonate: A solution of 3-isothiocyanatopropyl triflate (49 mg, 0.197 mmol) and 2-hydroxymethylpyridine (22 mg, 1 eq.) in toluene (1 mL) was stirred at RT for 20 hrs resulting in an oil precipitate. The top solvent layer was decanted and the precipitate was washed with toluene once and DCM three times. The solid was dried in high vacuum to give 67 mg (95%) as a tan oil. MS-ESI: 109.56 (M-CH2CH2NCS—OTf⁻), 149.58 (M-HNCS—OTf⁻), 208.66 (M-OTf⁻).

Example 1.32: Synthesis of 3-hydroxy-1-(3-isothiocyanatopropyl)pyridin-1-ium trifluoromethanesulfonate

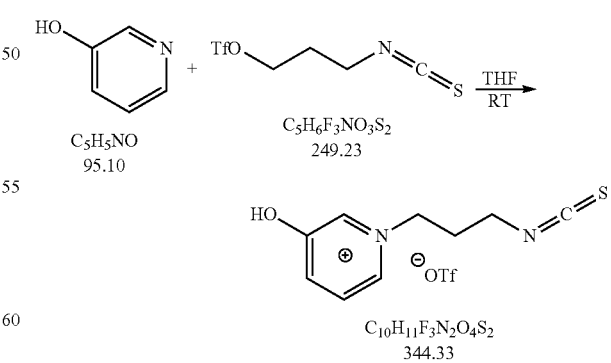

3-Hydroxypyridine (36 mg, 0.379 mmol) was dissolved in THF (0.5 mL) and 3-isothiocyanatopropyl triflate (104 mg, 0.418 mmol) was added. The solution was stirred at RT for 2 hrs. The solvent was evaporated to ⅕ volume and ether (1 mL) was added to precipitate. The top solvent layer was decanted. The process was repeated three times. The oil was dried in high vacuum to give 0.125 g (86.9%) as colorless oil. MS-ESI: 95.60 (M-CH2CH2NCS—OTf⁻), 135.59 (M-HNCS—OTf⁻), 194.67 (M-OTf⁻).

Example 1.33: Synthesis of 1-(2-hydroxyethyl)-1-(2-isothiocyanatoethyl)piperidin-1-ium trifluoromethanesulfonate

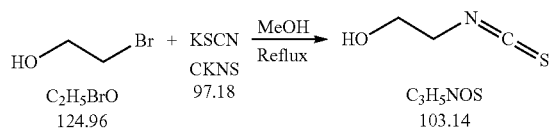

C₂H₅BrO  
124.96

CKNS  
97.18

C₃H₅NOS  
103.14

Synthesis of 2-Isothiocyanatoethanol: To a solution of potassium thiocyanate (1.159 g, 11.948 mmol) in MeOH (10 mL) was added 2-bromoethanol (1.971 g, 1 eq.) at RT. The solution was heated at reflux for 24 hrs. A white precipitate was formed during the heating. After cooing, the precipitate was removed by filtration and the filtrate was evaporated. The residue was analyzed by $^1$H NMR showing about 5:1 ratio of the product to starting material. The oil was distilled using a Kugelrohr apparatus at 0.3 Torr with the heating chamber temperature at <50° C. The undistilled residue gave 1.189 g (96.5%) as a light tan oil. $^1$H NMR (300 MHz, CDCl3): δ 4.03 (t, J=6.0 HZ, 2H), 3.16 (t, J=6.0 Hz, 2H).

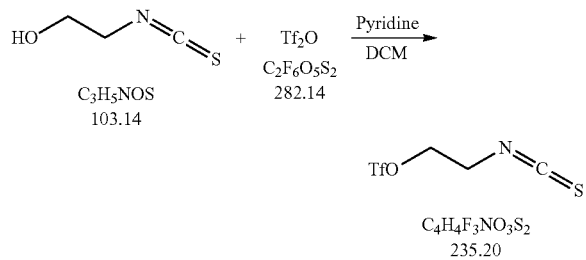

C₃H₅NOS  
103.14

C₂F₆O₅S₂  
282.14

C₄H₄F₃NO₃S₂  
235.20

Synthesis of 2-Isothiocyanatoethyl trifluoromethanesulfonate: To a solution of 2-isothiocyanatoethanol (1.189 g, 11.544 mmol) and pyridine (1.03 mL, 1.1 eq.) in DCM (10 mL) was added Tf₂O (2.146 mL, 1.1 eq.) dropwise at −70° C. After the addition, the mixture was stirred at −70° C. for 10 min and RT for 30 min. The mixture was washed with 0.5N HCl, saturated NaHCO₃, dried over anhydrous MgSO₄ and evaporated. The residue was distilled using a Kugelrohr apparatus at 0.05 Torr with the heating chamber temperature at <85° C. to give 1.532 g (56.4%) as a colorless oil. $^1$H NMR (300 MHz, CDCl3): δ 4.82 (t, J=6.0 HZ, 2H), 3.37 (t, J=6.0 Hz, 2H). $^{19}$F NMR (282 MHz, CDCl3): δ 74.6 (s, 3F).

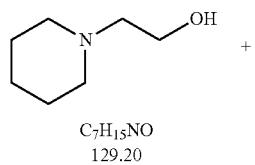

C₇H₁₅NO  
129.20

+

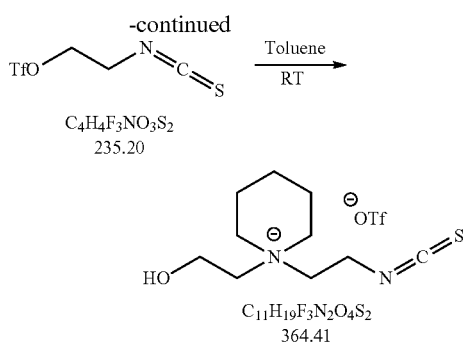

C₄H₄F₃NO₃S₂  
235.20

C₁₁H₁₉F₃N₂O₄S₂  
364.41

Synthesis of 1-(2-hydroxyethyl)-1-(2-isothiocyanatoethyl)piperidin-1-ium trifluoromethanesulfonate: A solution of 2-Isothiocyanatoethyl trifluoromethanesulfonate (25 mg, 0.106 mmol) and N-hydroxyethylpiperidine (14.8 mg, 1.05 eq.) in toluene (1 mL) was stirred at RT for 2 hrs. The solvent was decanted and the residual oil was washed with DCM (3×0.3 mL). The solid was dried in high vacuum to give 27.2 mg (70.5%) as colorless oil. MS-ESI: 129.67 (M-CH2CH2NCS—OTf⁻), 135.57 (M-HNCS—OTf⁻), 214.81 (M-OTf⁻).

Example 1.34: Synthesis of 2-(hydroxymethyl)-1-(2-isothiocyanatoethyl)-1-methylpiperidin-1-ium trifluoromethanesulfonate

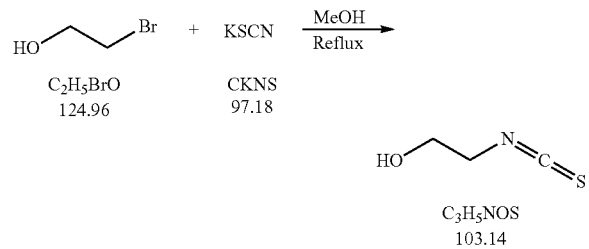

C₂H₅BrO  
124.96

CKNS  
97.18

C₃H₅NOS  
103.14

Synthesis of 2-Isothiocyanatoethanol: To a solution of potassium thiocyanate (1.159 g, 11.948 mmol) in MeOH (10 mL) was added 2-bromoethanol (1.971 g, 1 eq.) at RT. The solution was heated at reflux for 24 hrs. A white precipitate was formed during the heating. After cooing, the precipitate was removed by filtration and the filtrate was evaporated. The residue was analyzed by $^1$H NMR showing about 5:1 ratio of the product to starting material. The oil was distilled using a Kugelrohr apparatus at 0.3 Torr with the heating chamber temperature at <50° C. The undistilled residue gave 1.189 g (96.5%) as a light tan oil. $^1$H NMR (300 MHz, CDCl3): δ 4.03 (t, J=6.0 HZ, 2H), 3.16 (t, J=6.0 Hz, 2H).

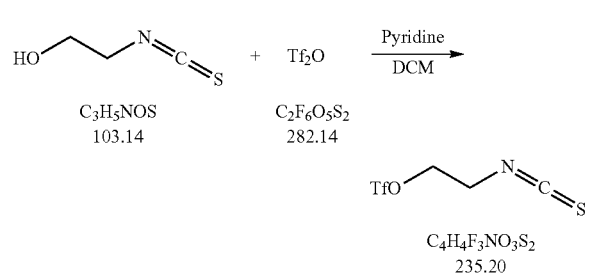

C₃H₅NOS  
103.14

C₂F₆O₅S₂  
282.14

C₄H₄F₃NO₃S₂  
235.20

Synthesis of 2-Isothiocyanatoethyl trifluoromethanesulfonate: To a solution of 2-isothiocyanatoethanol (1.189 g, 11.544 mmol) and pyridine (1.03 mL, 1.1 eq.) in DCM (10 mL) was added Tf$_2$O (2.146 mL, 1.1 eq.) dropwise at −70° C. After the addition, the mixture was stirred at −70° C. for 10 min and RT for 30 min. The mixture was washed with 0.5N HCl, saturated NaHCO$_3$, dried over anhydrous MgSO$_4$ and evaporated. The residue was distilled using a Kugelrohr apparatus at 0.05 Torr with the heating chamber temperature at <85° C. to give 1.532 g (56.4%) as a colorless oil. $^1$H NMR (300 MHz, CDCl3): δ 4.82 (t, J=6.0 HZ, 2H), 3.37 (t, J=6.0 Hz, 2H). $^{19}$F NMR (282 MHz, CDCl3): δ 74.6 (s, 3F).

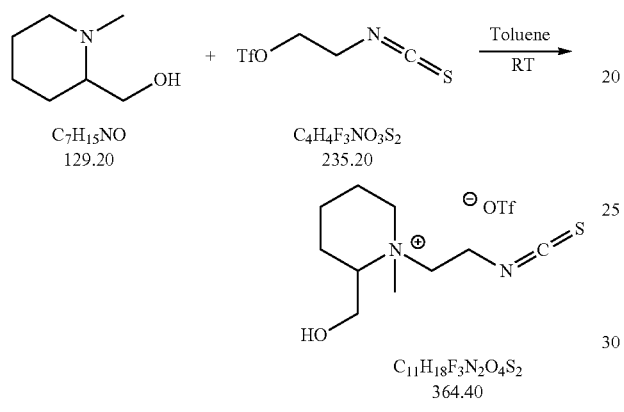

Synthesis of 2-(hydroxymethyl)-1-(2-isothiocyanatoethyl)-1-methylpiperidin-1-ium trifluoromethanesulfonate: A solution of 2-Isothiocyanatoethyl trifluoromethanesulfonate (30.2 mg, 0.128 mmol) and (1-methylpiperidin-2-yl)methanol (17.4 mg, 1.05 eq.) in toluene (0.5 mL) was stirred at RT for 2 hrs. The solvent was decanted and the residual oil was dissolved in DCM (0.3 mL) and Et2O (diethyl ether) (1 mL) was added to precipitate the salt. The top solvent layer was decanted. This process repeated twice. The residue was dried in high vacuum to give 41.9 mg (89.7%) as colorless oil. MS-ESI: 129.84 (M-CH2CH2NCS—OTf$^-$), 215.07 (M-OTf$^-$).

Example 1.35: Synthesis of 1-(2-hydroxyethyl)-1-(3-isothiocyanatopropyl)piperidin-1-ium trifluoromethanesulfonate

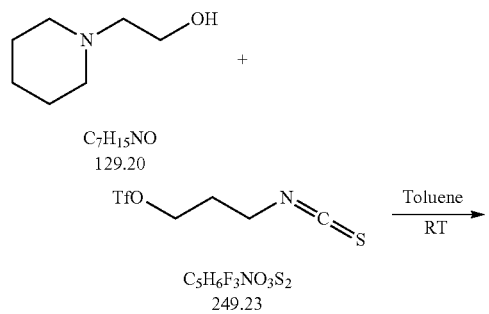

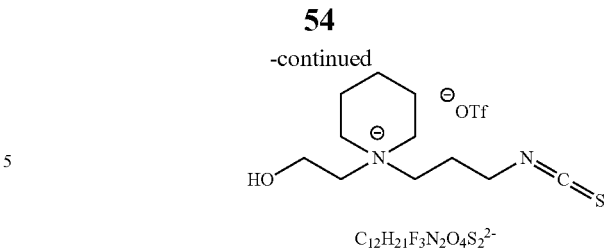

A solution of 2-isothiocyanatopropyl triflate (28.7 mg, 0.115 mmol) and N-hydroxyethylpiperidine (14.9 mg, 1 eq.) in toluene (1 mL) was stirred at RT for 2 hrs. The solvent was decanted and the residual oil was slurried in DCM and precipitated in Et2O (diethyl ether). The solvents were decanted. This process was repeated twice. The oil was dried in high vacuum to give 37.3 mg (85.7%) as light brown oil. MS-ESI: 129.59 (M-CH2CH2NCS—OTf$^-$), 228.76 (M-OTf$^-$).

Example 1.36: Synthesis of N-(2-hydroxyethyl)-3-isothiocyanato-N,N-dimethylpropan-1-aminium trifluoromethanesulfonate

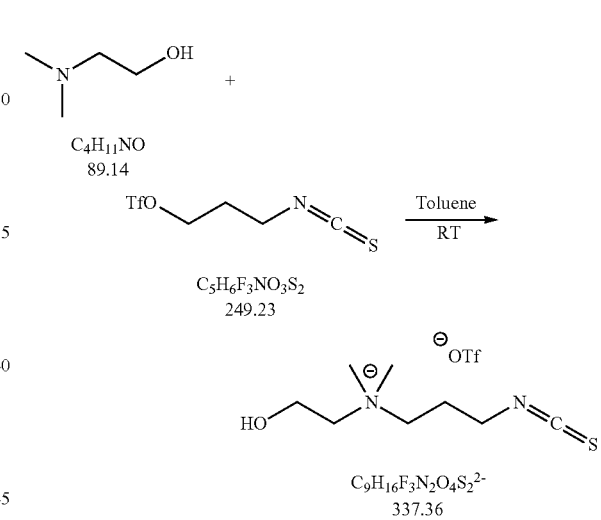

A solution of 2-isothiocyanatopropyl triflate (46.9 mg, 0.188 mmol) and dimethylaminoethanol (16.8 mg, 1 eq.) in toluene (1 mL) was stirred at RT for 2 hrs. The solvent was decanted and the residual oil was washed with toluene once, slurried in DCM and precipitated in Et2O. The solvents were decanted. This process was repeated twice. The oil was dried in high vacuum to give 55.4 mg (87.2%) as light brown oil. MS-ESI: 89.66 (M-CH2CH2CH2NCS—OTf$^-$), 129.62 (M-HNCS—OTf$^-$), 188.71 (M-OTf$^-$).

Example 1.37: Synthesis of N-(2-isothiocyanatoethyl)-N,N-dimethylprop-2-yn-1-aminium bromide

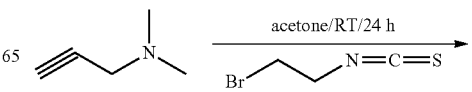

-continued

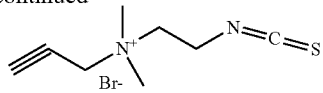

Chemical Formula: C₈H₁₃BrN₂S
Exact Mass: 248.00
Molecular Weight: 249.17

In a 500 mL round-bottomed flask equipped with a reflux condenser was generated a solution of N,N-dimethylpropargyl amine (CAS #7223-38-3, 3.25 mL) in 250 mL acetone. To this solution was added bromoethylisothiocyanate (5 g) in one portion at RT. The reaction was refluxed for 24 h, then cooled to RT. The reaction was then cooled in an ice-water bath for 1 h, and the crystals formed were collected via filtration using a Buchner funnel (5-10 mm Hg) under vacuum. The resulting white solid was washed with acetone (3×200 mL), dried under vacuum at RT (5-10 mm Hg, 24 h), and then collected to provide the final product. 1.17 g. LC/MS (ESI): 170 (M-Br—).

Example 1.38: Synthesis of N-(2-isothiocyanatoethyl)-2-(methoxycarbonyl)-N,N-dimethylprop-2-en-1-aminium bromide

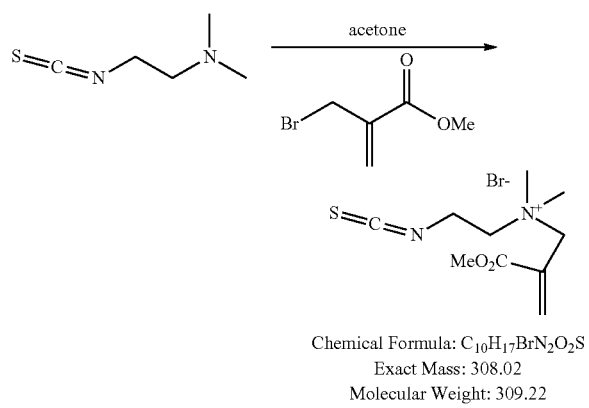

Chemical Formula: C₁₀H₁₇BrN₂O₂S
Exact Mass: 308.02
Molecular Weight: 309.22

In a 250 mL round-bottomed flask equipped with a reflux condenser was generated a solution of aminoisothiocyanate (CAS #7092-89-4, Enamine, 2.5 g) in 125 mL acetone. To this solution was added bromomethylmethylacrylate (CAS #4224-69-5, Sigma Aldrich, 3.6 g) in one portion at RT. The reaction was refluxed for 24 h, and then cooled to RT. The crystals formed were collected via filtration using a Buchner funnel (5-10 mm Hg) under vacuum. The resulting white solid was washed with Et2O (2×250 mL), dried under vacuum at RT (5-10 mm Hg, 24 h), and then collected to provide the final product. 122 mg. LC/MS (ES–): 308.

Example 1.39: Synthesis of 4-hydroxy-1-(2-isothiocyanatoethyl)-1-methylpiperidin-1-ium bromide

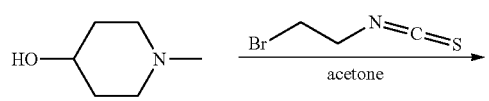

-continued

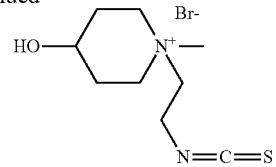

Chemical Formula: C₉H₁₇BrN₂OS
Exact Mass: 280.02
Molecular Weight: 281.21\

In a 250 mL round-bottomed flask equipped with a stir bar was added a 1-methylpiperin-4-ol (CAS #106-52-5, Aldrich, 0.945 mL) and 125 mL acetone. To this was added bromoethylisothiocyanate (CAS #1483-41-6, Matrix, 2 g) in a single portion. The reaction was stirred at RT for 24 h. The solvent was stripped off (rotary evaporator/5-10 mm Hg) and the residue was triturated with 3×100 mL Et₂O. The residue was then pumped under house vacuum (5-10 mm Hg) for 24 h to provide a brown waxy solid. 412 mg. LC/MS: (ES+-Br—) 201.

Example 1.40: Synthesis of 4-Methyl-4-(2-isothiocyanatoethyl)morpholinium trifluoromethanesulfonate

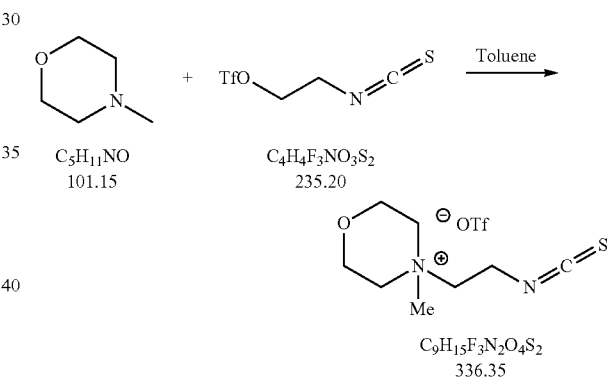

A mixture of 2-isothiocyanatoethyl trifluoromethanesulfonate (74.6 mg, 0.317 mmol) and N-methylmorpholine (42 μL, 1.2 eq.) in toluene (0.5 mL) was stirred at RT for 18 hrs resulting in a precipitate. The liquid layer was decanted, the solid was washed with toluene once and ether twice. The residue was dried in high vacuum to give 91.4 mg (85.8%) as a white solid. MS-ESI: 187.56 (M-OTf⁻).

Example 1.41: Synthesis of 1-Methyl-1-(2-isothiocyanatoethyl)piperidium trifluoromethanesulfonate

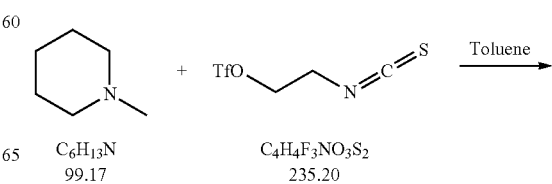

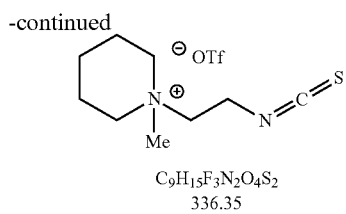

C₉H₁₅F₃N₂O₄S₂
336.35

A mixture of 2-isothiocyanatoethyl trifluoromethanesulfonate (81.2 mg, 0.346 mmol) and N-methylpiperidine (41.1 µL, 1.2 eq.) in toluene (0.5 mL) was stirred at RT for 18 hrs resulting in a precipitate. The liquid layer was decanted, the solid was washed with toluene once and ether twice. The residue was dried in high vacuum to give 109.5 mg (94.8%) as a white solid. MS-ESI: 185.51 (M-OTf⁻).

Example 1.42: Synthesis of 1-(2-Isothiocyanatoethyl)quinuclidinium trifluoromethanesulfonate

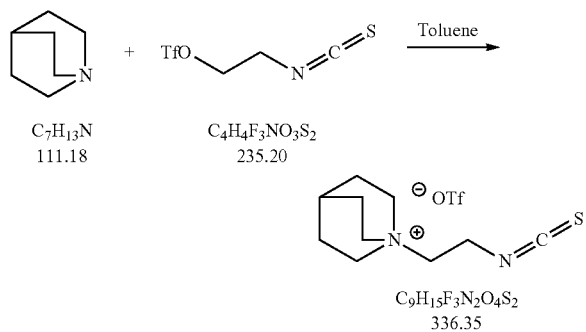

C₇H₁₃N
111.18

C₄H₄F₃NO₃S₂
235.20

C₉H₁₅F₃N₂O₄S₂
336.35

A mixture of 2-isothiocyanatoethyl trifluoromethanesulfonate (78.2 mg, 0.333 mmol) and quinuclidine (37 mg, 1 eq.) in toluene (0.5 mL) was stirred at RT for 8 hrs resulting in a precipitate. The solid was collected by filtration, washed with toluene once and ether twice. The residue was dried in high vacuum to give 104.6 mg (90.8%) as a white solid. MS-ESI: 197.64 (M-OTf⁻).

Example 1.43: Synthesis of 4-Methyl-4-(3-isothiocyanatopropyl) morpholinium trifluoromethanesulfonate

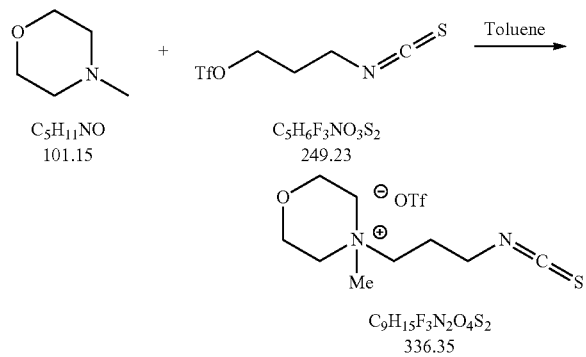

C₅H₁₁NO
101.15

C₅H₆F₃NO₃S₂
249.23

C₉H₁₅F₃N₂O₄S₂
336.35

A mixture of 2-isothiocyanatopropyl trifluoromethanesulfonate (91.2 mg, 0.366 mmol) and N-methylmorpholine (44.5 mg, 0.366 mmol) in toluene (0.5 mL) was stirred at RT for 18 hrs resulting in a precipitate. The solid was collected by filtration, washed with toluene once and ether twice. The residue was dried in high vacuum to give 130 mg (96.3%) as a white solid. MS-ESI: 201.64 (M-OTf⁻).

Example 1.44: Synthesis of 1-Methyl-1-(3-isothiocyanatopropyl)piperidinium trifluoromethanesulfonate

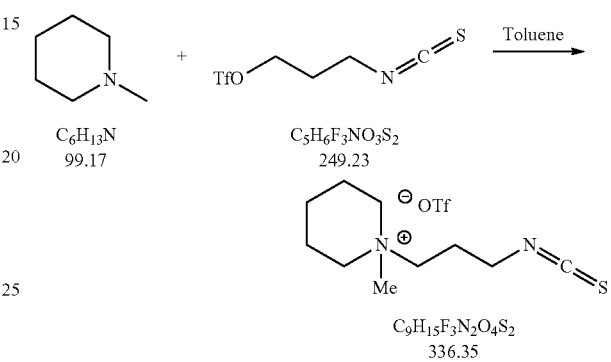

C₆H₁₃N
99.17

C₅H₆F₃NO₃S₂
249.23

C₉H₁₅F₃N₂O₄S₂
336.35

A mixture of 3-isothiocyanatopropyl trifluoromethanesulfonate (87.4 mg, 0.363 mmol) and N-methylpiperidine (43 mg, 1.2 eq.) in toluene (0.5 mL) was stirred at RT for 18 hrs resulting in a precipitate. The liquid layer was decanted, the solid was washed with toluene once and ether twice. The residue was dried in high vacuum to give 115 mg (88.5%) as a white solid. MS-ESI: 199.53 (M-OTf⁻).

Example 1.45: Synthesis of 1-(3-Isothiocyanatopropyl) quinuclidinium trifluoromethanesulfonate

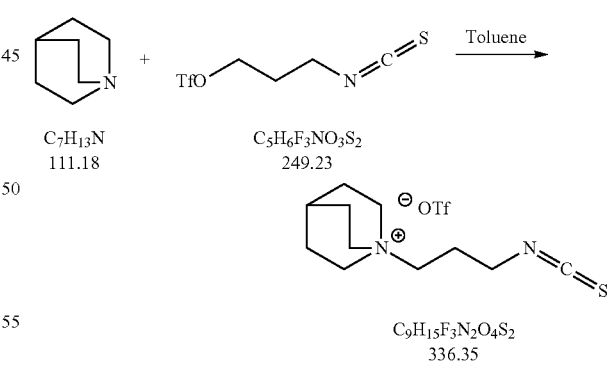

C₇H₁₃N
111.18

C₅H₆F₃NO₃S₂
249.23

C₉H₁₅F₃N₂O₄S₂
336.35

A mixture of 3-isothiocyanatopropyl trifluoromethanesulfonate (119 mg, 0.476 mmol) and quinuclidine (52.9 mg, 1 eq.) in toluene (0.5 mL) was stirred at RT for 18 hrs resulting in a precipitate. The liquid layer was decanted, the solid was washed with toluene once and ether twice. The residue was dried in high vacuum to give 163 mg (94.8%) as a white solid. MS-ESI: 211.60 (M-OTf⁻).

EXAMPLES 2 and 3 provide exemplary methods of identifying and quantitating TMA in a sample, as well as screening candidate inhibitory compounds of Formula (I), or Formula (II). All compounds in TABLE 2 were found to inhibit the conversion of choline to TMA. All compounds in TABLE 3 were found to inhibit the conversion of carnitine to TMA.

EXAMPLE 2 Assay for identifying and characterizing compounds that inhibit the formation of TMA from choline.

This example provides an exemplary assay for identifying and characterizing compounds that inhibit the formation of TMA from choline.

*Proteus mirabilis* 29906 (Pm) strain was grown aerobically overnight in 500 ml of Nutrient Broth media (3 g/L beef extract, 5 g/L Peptone; Difco #234000) at 37° C. with 250 rpm shaking. The biomass was pelleted by centrifugation at 6000×g for 12 minutes at 4° C. The cell pellet was suspended in 240 mL of ice-cold 1× Phosphate Buffered Saline ($Ca^{2+}$ and $Mg^{2+}$ free). Ninety micrograms of Lysozyme (Sigma #L6876 Lot #SLBG8654V; Sigma-Aldrich Corp., St. Louis, Mo.) was added and incubated with 320 rpm shaking for 30 minutes at 4° C. Lysis was achieved via French press with a 4° C. prechilled 1" diameter chamber at 1000 psi (high ratio; internal PSI equivalent ~16000). The lysate was centrifuged at 6,000×g for 12 minutes at 4° C. to pellet extra debris. A protein concentration of the centrifuged lysate supernatant was determined by a BCA Protein Assay Kit (Pierce #23225; Thermo Fisher Scientific Co., Waltham, Mass.) and protein concentration adjusted to 3 mg/ml with 1× Dulbecco's phosphate buffered saline (DPBS). The centrifuged supernatant lysate was aliquoted into 20 mL volumes and stored frozen at −80° C.

*Proteus mirabilis* 29906 (Pm) lysate was diluted to 1.5 mg/mL protein with 1×DPBS. Choline chloride (CC) (1M stock) was added to reach a final concentration of 2.5 mM choline chloride. The mixture was mixed using a vortex mixer for approximately 15 seconds and incubated at 37° C. for 22 hours. After incubation, 150 μL of CC-treated Pm lysate was dispensed into a deep-well plate (polypropylene, 2 mL volume, Corning Axygen catalogue #P-DW-20-C). Candidate $IC_{50}$ compounds from TABLE 1 and vehicle control (respective vehicle control of DMSO or water), or control compounds (IC50 control, 8-Quinolinol hemisulfate salt (Sigma Catalog #55100)) were added at a 1:100 dilution (e.g., 1.5 μL per well). The plates were agitated on a plate shaker for 1 minute. d9-choline chloride (1.5 μL of 5 mM) was added to all wells to reach a final d9-choline chloride concentration of 50 μM.

The plates were again agitated on a plate shaker for 1 minute and incubated at 37° C. for two hours. After incubation, 1.5 μL of formic acid was added to each well (final concentration=1% formic acid). The plates were agitated on a plate shaker for 1 minute and placed on ice. Cell lysate samples were spiked with stable isotope labeled internal standard (22.5 μL of 6 μg/mL of 13C3-trimethylamine (13C3-TMA) was added to each sample), then d9-trimethylamine (d9-TMA), trimethylamine (TMA) and 13C3-TMA were isolated from the lysate after protein precipitation as described below. Acetonitrile acidified with 0.1% formic acid, 600 μL, was added to each sample which was then centrifuged (2,100 g for 20 minutes) to pellet the protein and other precipitates. The supernatant was removed and analyzed as described below. The TMA, d9-TMA and 13C3-TMA in the isolated supernatant samples were subjected to gradient High Performance Liquid Chromatography (HPLC) analysis on a Waters Atlantis HILIC Silica column, from Waters Corp., Milford, Mass., (2.1×50 mm, 3 μm particles) with an Atlantis Silica HILIC Sentry guard column, from Waters Corp., Milford, Mass., (100 Å, 3 μm, 2.1 mm×10 mm), 10 mM ammonium formate in water with 0.1% formic acid as mobile phase A and 0.1% formic acid in acetonitrile as mobile phase B. Detection and quantitation was achieved by tandem mass spectrometry operating under multiple reaction monitoring (MRM) MS/MS conditions (m/z 60.1→44.1 for TMA, m/z 69.1→49.1 for d9-TMA, m/z 63.0→46.1 for 13C3-TMA). TMA and d9-TMA calibration standards (STD), prepared in 80/20/0.1% acetonitrile/Water/Formic Acid, were used to construct a regression curve by plotting the response (peak area TMA/peak area 13C3-TMA) versus concentration for each standard. The concentrations of TMA and d9-TMA in the cell lysate were determined by interpolation from the quadratic (1/x2) regression curve.

$IC_{50}$ measurements for inhibition of conversion of choline to TMA, as outlined in EXAMPLE 2, for representative compounds of Formula (I), or Formula (II), are set forth in TABLE 2.

TABLE 2

| ID | Compound | TMA Inhibition (IC50, mol/L) | SMILES |
|---|---|---|---|
| 1 | N,N-Diethyl-2-isothiocyanato-N-methylpropanaminium iodide | 1.519E−05 | S=C=NCC[N+](CC)(C)CC•[I−] |
| 2 | 3-Isothiocyanato-N,N-diethyl-N-methylpropanaminium iodide | 1.062E−05 | CC[N+](CC)(C)CCCN=C=S•[I−] |
| 3 | N-(Ethoxycarbonylethyl)-3-isothiocyanato-N,N-diethylpropan-1-aminium bromide | 8.260E−05 | S=C=NCCC[N+](CC(OCC)=O)(CC)CC•[Br−] |
| 4 | N-(Ethoxycarbonylethyl)-2-isothiocyanato-N,N-dimethylethan-1-aminium bromide | 2.206E−04 | C[N+](CC(OCC)=O)(C)CCN=C=S•[Br−] |
| 5 | N-(Ethoxypropyl-2,3-dione)-2-isothiocyanato-N,N-dimethylethan-1-aminium bromide | 7.691E−04 | C[N+](CC(C(OCC)=O)=O)(C)CCN=C=S•[Br−] |
| 6 | N-(Ethoxypropyl-2,3-dione)-3-isothiocyanato-N,N-diethylpropan-1-aminium | 1.443E−05 | C[N+](CC(C(OCC)=O)=O)(C)CCCN=C=S•[Br−] |

TABLE 2-continued

| ID | Compound | TMA Inhibition (IC50, mol/L) | SMILES |
|---|---|---|---|
| | bromide | | |
| 7 | N-(2-Bromoethyl)-3-isothiocyanato-N,N-diethylpropan-1-aminium triflate | 1.824E−05 | S═C═NCCC[N+](CCBr)(CC)CC•O═S(C(F)(F)F)([O−])═O |
| 8 | N-Cyanomethyl-2-isothiocyanato-N,N-diethylethan-1-aminium bromide | 4.305E−05 | S═C═NCC[N+](C)(CC#N)C•[Br−] |
| 9 | N-Cyanomethyl-3-isothiocyanato-N,N-diethylpropan-1-aminium bromide | 6.053E−05 | N#CC[N+](CCCN═C═S)(CC)CC•[Br−] |
| 10 | N-(2-Phenoxyethyl)-3-isothiocyanato-N,N-diethylpropan-1-aminium triflate | 2.964E−05 | S═C═NCCC[N+](CCOC1═CC═CC═C1)(CC)CC•O═S(C(F)(F)F)([O−])═O |
| 11 | N-(2-Benzyloxyethyl)-2-isothiocyanato-N,N-dimethylethan-1-aminium triflate | 1.613E−05 | C[N+](CCOCC1═CC═CC═C1)(C)CCN═C═S•O═S(C(F)(F)F)([O−])═O |
| 12 | N-(2-Benzyloxyethyl)-3-isothiocyanato-N,N-diethylpropan-1-aminium triflate | 2.910E−05 | CC[N+](CCCN═C═S)(CCOCC1═CC═CC═C1)CC•O═S(C(F)(F)F)([O−])═O |
| 13 | N-(2-Phenoxyethyl)-2-isothiocyanato-N,N-dimethylethan-1-aminium triflate | 1.326E−06 | C[N+](CCOC1═CC═CC═C1)(C)CCN═C═S•O═S(C(F)(F)F)([O−])═O |
| 14 | N-(2-Bromoethyl)-2-isothiocyanato-N,N-dimethylethan-1-aminium triflate | 2.495E−05 | C[N+](CCBr)(C)CCN═C═S•O═S(C(F)(F)F)([O−])═O |
| 15 | N-(Oxiranylmethyl)-2-isothiocyanato-N,N-dimethylethan-1-aminium triflate | 1.945E−04 | C[N+](CC1CO1)(C)CCN═C═S•O═S(C(F)(F)F)([O−])═O |
| 16 | N-(Oxiranylmethyl)-3-isothiocyanato-N,N-diethylpropan-1-aminium triflate | 3.981E−05 | CC[N+](CCCN═C═S)(CC1OC1)CC•O═S(C(F)(F)F)([O−])═O |
| 17 | N-(2-Methoxyethyl)-2-isothiocyanato-N,N-dimethylethan-1-aminium triflate | 3.162E−05 | C[N+](CCOC)(C)CCN═C═S•O═S(C(F)(F)F)([O−])═O |
| 18 | N-(2-Methoxyethyl)-3-isothiocyanato-N,N-diethylpropan-1-aminium triflate | 3.981E−05 | S═C═NCCC[N+](CCOC)(CC)CC•O═S(C(F)(F)F)([O−])═O |
| 19 | N-(2-Ethoxyethyl)-2-isothiocyanato-N,N-dimethylethan-1-aminium triflate | 6.310E−05 | C[N+](CCOCC)(C)CCN═C═S•O═S(C(F)(F)F)([O−])═O |
| 20 | N-(2-Ethoxyethyl)-3-isothiocyanato-N,N-diethylpropan-1-aminium triflate | 1.995E−05 | S═C═NCCC[N+](CCOCC)(CC)CC•O═S(C(F)(F)F)([O−])═O |
| 21 | N-(3-Methoxypropyl)-2-isothiocyanato-N,N-dimethylethan-1-aminium triflate | 3.162E−05 | C[N+](CCCOC)(C)CCN═C═S•O═S(C(F)(F)F)([O−])═O |
| 22 | N-(3-Methoxyethyl)-3-isothiocyanato-N,N-diethylpropan-1-aminium triflate | 3.162E−05 | S═C═NCCC[N+](CCCOC)(CC)CC•O═S(C(F)(F)F)([O−])═O |
| 23 | N-(2-Chloroethyl)-2-isothiocyanato-N,N-dimethylethan-1-aminium triflate | 2.512E−05 | C[N+](CCCl)(C)CCN═C═S•O═S(C(F)(F)F)([O−])═O |
| 24 | N-(3-Chloropropyl)-2-isothiocyanato-N,N-dimethylethan-1-aminium triflate | 6.310E−05 | C[N+](CCCCl)(C)CCN═C═S•O═S(C(F)(F)F)([O−])═O |
| 25 | N-(2-Chloroethyl)-3-isothiocyanato-N,N- | 1.995E−05 | ClCC[N+](CC)(CC)CCCN═C═S•O═S(C(F)(F)F)([O−])═O |

TABLE 2-continued

| ID | Compound | TMA Inhibition (IC50, mol/L) | SMILES |
|---|---|---|---|
| | diethylpropan-1-aminium triflate | | |
| 26 | N-(3-Chloropropyl)-3-isothiocyanato-N,N-diethylpropan-1-aminium triflate | 5.012E−05 | S═C═NCCC[N+](CC)(CC)CCCCl•O═S(C(F)(F)F)([O−])═O |
| 27 | N-(2-Fluorooethyl)-3-isothiocyanato-N,N-diethylpropan-1-aminium triflate | 3.162E−05 | FCC[N+](CC)(CC)CCCN═C═S•O═S(C(F)(F)F)([O−])═O |
| 28 | 1-(2-Isothiocyanatoethyl)pyridin-1-ium bromide | 3.162E−05 | S═C═NCC[N+]1═CC═CC═C1•[Br−] |
| 29 | 1-(2-Isothiocyanatoethyl)-3-hydroxypyridinium bromide | 1.259E−03 | S═C═NCC[N+]1═CC(O)═CC═C1•[Br−] |
| 30 | 1-(2-Isothiocyanatoethyl)-(2-hydroxymethyl)pyridinium triflate | 2.512E−05 | S═C═NCC[N+]1═CC═CC═C1CO•O═S(C(F)(F)F)([O−])═O |
| 31 | 2-(hydroxymethyl)-1-(3-isothiocyanatopropyl)pyridin-1-ium trifluoromethanesulfonate | 2.512E−04 | OCC1═CC═CC═[N+]1CCCN═C═S•O═S(C(F)(F)F)([O−])═O |
| 32 | 3-hydroxy-1-(3-isothiocyanatopropyl)pyridin-1-ium trifluoromethanesulfonate | 1.995E−03 | S═C═NCCC[N+]1═CC(O)═CC═C1•O═S(C(F)(F)F)([O−])═O |
| 33 | 1-(2-hydroxyethyl)-1-(2-isothiocyanatoethyl)piperidin-1-ium trifluoromethanesulfonate | 1.995E−04 | S═C═NCC[N+]1(CCCCC1)CCO•O═S(C(F)(F)F)([O−])═O |
| 34 | 2-(hydroxymethyl)-1-(2-isothiocyanatoethyl)-1-methylpiperidin-1-ium trifluoromethanesulfonate | 3.162E−04 | S═C═NCC[N+]1(C)C(CO)CCCC1•O═S(C(F)(F)F)([O−])═O |
| 35 | 1-(2-hydroxyethyl)-1-(3-isothiocyanatopropyl)piperidin-1-ium trifluoromethanesulfonate | 1.259E−03 | OCC[N+]1(CCCCC1)CCCN═C═S•O═S(C(F)(F)F)([O−])═O |
| 36 | N-(2-hydroxyethyl)-3-isothiocyanato-N,N-dimethylpropan-1-aminium trifluoromethanesulfonate | 1.000E−04 | C[N+](CCO)(C)CCCN═C═S•O═S(C(F)(F)F)([O−])═O |
| 37 | N-(2-isothiocyanatoethyl)-N,N-dimethylprop-2-yn-1-aminium bromide | 1.987E−06 | C[N+](CCN═C═S)(C)CC#C•[Br−] |
| 38 | N-(2-isothiocyanatoethyl)-2-(methoxycarbonyl)-N,N-dimethylprop-2-en-1-aminium bromide | 1.406E−05 | S═C═NCC[N+](C)(C)CC(C(OC)═O)═C•[Br−] |
| 39 | 4-hydroxy-1-(2-isothiocyanatoethyl)-1-methylpiperidin-1-ium bromide | 2.588E−05 | OC1CC[N+](CCN═C═S)(C)CC1•[Br−] |
| 40 | 4-Methyl-4-(2-isothiocyanatoethyl)morpholinium trifluoromethanesulfonate | 2.865E−04 | S═C═NCC[N+]1(C)CCOCC1•O═S(C(F)(F)F)([O−])═O |
| 41 | 1-Methyl-1-(2-isothiocyanatoethyl)piperidium trifluoromethanesulfonate | 3.172E−05 | S═C═NCC[N+]1(C)CCCCC1•O═S(C(F)(F)F)([O−])═O |
| 42 | 1-(2-Isothiocyanatoethyl)quinuclidinium trifluoromethanesulfonate | 1.209E−05 | S═C═NCC[N+]12CCC(CC2)CC1•O═S(C(F)(F)F)([O−])═O |
| 43 | 4-Methyl-4-(3-isothiocyanatopropyl)morpholinium trifluoromethanesulfonate | >1.000E−03 | S═C═NCCC[N+]1(C)CCOCC1•O═S(C(F)(F)F)([O−])═O |
| 44 | 1-Methyl-1-(3-isothiocyanatopropyl)piperidinium trifluoromethanesulfonate | >1.000E−03 | S═C═NCCC[N+]1(C)CCCCC1•O═S(C(F)(F)F)([O−])═O |
| 45 | 1-(3-Isothiocyanatopropyl)quinuclidinium trifluoromethanesulfonate | 1.152E−04 | S═C═NCCC[N+]12CCC(CC2)CC1•O═S(C(F)(F)F)([O−])═O |

Example 3

EXAMPLE 3 provides an exemplary assay for identifying and characterizing compounds from Formula (I), or Formula (II), that inhibit the formation of TMA from carnitine.

*Escherichia coli* BL21*DE3::pET30a-Ec yeaWX #1 (Ec YeaWX) strain was generated as described below. The contiguous *Escherichia coli* coding sequence yeaW (equivalent to uniprot ID P0ABR7.1 (YeaW) (SEQ ID NO: 2)) and yeaX (equivalent to uniprot ID P76254.1 (YeaX) (SEQ ID NO: 3)) were PCR amplified from *Escherichia coli* strain K-12 substr. BW25113 genomic DNA. PCR primers (YeaW_Nde I_fwd2-SEQ ID NO: 4; YeaX_rev2-SEQ ID NO: 5) were designed to create a 5' NdeI restriction site including the ATG start codon of yeaW and create a PstI restriction site just 3' of the yeaX TAG stop codon.

The amplicon was restricted and cloned into the NdeI and PstI sites of the plasmid pET30a downstream of the inducible T7 promoter. A blast search of the resulting cloned amplicon DNA sequence (SEQ ID NO: 1) corresponded to nucleotide range 1884665 to 1886810 of *Escherichia coli* str. K-12 substr. MG1655 (NCBI Accession #NC_000913). The construct was transformed and grown in *E. coli* BL21 (DE3) and the recombinant yeaWX overexpressed by addition of isopropyl β-D-1-thiogalactopyranoside (IPTG).

| SEQ ID NO | Sequence |
| --- | --- |
| 1 | *Escherichia coli* yeaWX amplicon sequence |
| 2 | uniprot ID P0ABR7.1, YeaW |
| 3 | uniprot ID P76254.1, YeaX |
| 4 | YeaW_Nde I_fwd2 |
| 5 | YeaX_rev2 |

A sequence listing that sets forth the nucleotide sequences for SEQ ID NO: 1 to 5 herein is being filed concurrently with the present application as an ASCII text file titled "14606_Nucleotide_Sequence_Listing_ST25." The ASCII text file was created on 28 Nov. 2016 and is 10 Kbytes in size. In accordance with MPEP § 605.08 and 37 CFR § 1.52(e), the subject matter in the ASCII text file is incorporated herein by reference.

The bacteria were grown aerobically in 50 mL LB broth (Difco #244620; 10 g/L Tryptone, 5 g/L yeast extract, 10 g/L NaCl, 50 µg/mL kanamycin), in a 500 mL Erlenmeyer flask. The cultures were inoculated from glycerol stock of BL21*DE3::pET30a-Ec yeaWX #1 strain. Strains were cultured all day at 37° C. with 250 rpm shaking. Two 300 mL Minimal M9 Medium (6 g/L $Na_2HPO_4$, 3 g/L $KH_2PO_4$, 0.5 g/L NaCl, 1 g/L $NH_4Cl$, 0.1 mM $CaCl_2$, 1 mM $MgSO_4$, 0.2% Dextrose, 1 mg/L Thiamine, 50 µg/mL kanamycin), in 1 L Erlenmeyer flasks, were inoculated with 5 mL of the LB broth day culture and cultured overnight at 37° C. with 250 rpm shaking. The overnight cultures were used to inoculate twelve 1 L cultures of Minimal M9 media in 2.8 L fluted Erlenmeyer flasks to an OD 600 nm of 0.05 (typically approximately 28 mLs), which were grown at 37° C. with 250 rpm shaking until an OD600 of approximately 0.4 was reached. Expression of YeaWX was induced with 1 mM IPTG and the induced cultures were further grown overnight at 37° C. with 250 rpm shaking. The biomass was pelleted by centrifugation at 6000×g for 12 minutes at 4° C. The cell pellet was suspended in 240 mL of ice-cold 1× Phosphate Buffered Saline ($Ca^{2+}$ and $Mg^{2+}$ free). Ninety micrograms of Lysozyme (Sigma #L6876 Lot #SLBG8654V; Sigma-Aldrich Corp., St. Louis, Mo.) was added and incubated with 320 rpm shaking for 30 minutes at 4° C. Lysis was achieved via French press with a 4° C. prechilled 1" diameter chamber at 1000 psi (high ratio; internal PSI equivalent ~16000). The lysate was centrifuged at 6,000×g for 12 minutes at 4° C. to pellet extra debris. Glycerol was added to the centrifuged lysate supernatant at a final concentration of 15% A protein concentration of the centrifuged lysate supernatant was determined by a BCA Protein Assay Kit (Pierce #23225), typically in the 2.5 to 4.5 mg/ml range. The centrifuged Ec YeaWX lysate supernatant was aliquoted into 20 mL volumes and stored frozen at −80° C.

Ec YeaWX lysate was diluted to 2.0 mg/mL protein with 1× Dulbecco's phosphate buffered saline (DPBS) plus 15% glycerol. Nicotinamide adenine dinucleotide phosphate (NADPH) was added to 250 µM. One hundred and fifty microliters of Ec YeaWX lysate was dispensed into a deep-well plate (polypropylene, 2 mL volume, Corning Axygen catalogue #P-DW-20-C). Candidate $IC_{50}$ compounds from TABLE 1 and vehicle control (respective vehicle control of DMSO or water), or control compounds (IC50 control, 8-Quinolinol hemisulfate salt (Sigma Catalog #55100)) were added at a 1:100 dilution (e.g., 1.5 µL per well). The plates were agitated on a plate shaker for 1 minute. d9-carnitine chloride (1.5 µL of 5 mM) was added to all wells to reach a final d9-carnitine chloride concentration of 50 µM.

The plates were again agitated on a plate shaker for 1 minute and incubated at 37° C. for two hours. After incubation, 1.5 µL of formic acid was added to each well (final concentration=1% formic acid). The plates were agitated on a plate shaker for 1 minute and placed on ice. Cell lysate samples were spiked with stable isotope labeled internal standard (22.5 µL of 6 µg/mL of 13C3-trimethylamine (13C3-TMA) was added to each sample), then d9-trimethylamine (d9-TMA), trimethylamine (TMA) and 13C3-TMA were isolated from the lysate after protein precipitation as described below. Acetonitrile acidified with 0.1% formic acid, 600 µL, was added to each sample which was then centrifuged (2,100 g for 20 minutes) to pellet the protein and other precipitates. The supernatant was removed and analyzed as described below. The TMA, d9-TMA and 13C3-TMA in the isolated supernatant samples were subjected to gradient High Performance Liquid Chromatography (HPLC) analysis on a Waters Atlantis HILIC Silica column, from Waters Corp., Milford, Mass., (2.1×50 mm, 3 µm particles) with an Atlantis Silica HILIC Sentry guard column, from Waters Corp., Milford, Mass., (100 Å, 3 µm, 2.1 mm×10 mm), 10 mM ammonium formate in water with 0.1% formic acid as mobile phase A and 0.1% formic acid in acetonitrile as mobile phase B. Detection and quantitation was achieved by tandem mass spectrometry operating under multiple reaction monitoring (MRM) MS/MS conditions (m/z 60.1→44.1 for TMA, m/z 69.1→49.1 for d9-TMA, m/z 63.0→46.1 for 13C3-TMA). TMA and d9-TMA calibration standards (STD), prepared in 80/20/0.1% acetonitrile/Water/Formic Acid, were used to construct a regression curve by plotting the response (peak area TMA/peak area 13C3-TMA) versus concentration for each standard. The concentrations of TMA and d9-TMA in the cell lysate were determined by interpolation from the quadratic (1/x2) regression curve.

$IC_{50}$ measurements for inhibition of conversion of carnitine to TMA, as outlined in EXAMPLE 3, for representative compounds of Formula (I), or Formula (II), are set forth in TABLE 3.

TABLE 3

| ID | Compound | TMA Inhibition (IC50, mol/L) | SMILES |
|---|---|---|---|
| 1 | N,N-Diethyl-2-isothiocyanato-N-methylpropanaminium iodide | 0.00011 | S=C=NCC[N+](CC)(C)CC•[I-] |
| 2 | 3-Isothiocyanato-N,N-diethyl-N-methylpropanaminium iodide | 0.00020 | CC[N+](CC)(C)CCCN=C=S•[I-] |
| 3 | N-(Ethoxycarbonylethyl)-3-isothiocyanato-N,N-diethylpropan-1-aminium bromide | 0.00022 | S=C=NCCC[N+](CC(OCC)=O)(CC)CC•[Br-] |
| 4 | N-(Ethoxycarbonylethyl)-2-isothiocyanato-N,N-dimethylethan-1-aminium bromide | 0.00030 | C[N+](CC(OCC)=O)(C)CCN=C=S•[Br-] |
| 5 | N-(Ethoxypropyl-2,3-dione)-2-isothiocyanato-N,N-dimethylethan-1-aminium bromide | 0.00551 | C[N+](CC(C(OCC)=O)=O)(C)CCN=C=S•[Br-] |
| 6 | N-(Ethoxypropyl-2,3-dione)-3-isothiocyanato-N,N-diethylpropan-1-aminium bromide | 0.00020 | C[N+](CC(C(OCC)=O)=O)(C)CCCN=C=S•[Br-] |
| 7 | N-(2-Bromoethyl)-3-isothiocyanato-N,N-diethylpropan-1-aminium triflate | 0.00017 | S=C=NCCC[N+](CCBr)(CC)CC•O=S(C(F)(F)F)([O-])=O |
| 8 | N-Cyanomethyl-2-isothiocyanato-N,N-diethylethan-1-aminium bromide | 0.00021 | S=C=NCC[N+](C)(CC#N)C•[Br-] |
| 9 | N-Cyanomethyl-3-isothiocyanato-N,N-diethylpropan-1-aminium bromide | 0.00060 | N#CC[N+](CCCN=C=S)(CC)CC•[Br-] |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of inhibiting the conversion of choline or carnitine to trimethylamine (TMA) by a bacterium comprising: contacting the bacterium with a compound as set forth in Formula (I):

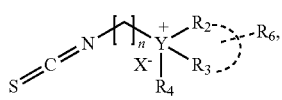

FORMULA (I)

wherein
- $Y^+$ is selected from a quaternary nitrogen; $X^-$ is an anion; n is selected from 1, 2 or 3; $R_2$ and $R_3$ are independently selected from C1-4 alkyl or bound together forming an aliphatic, aromatic or heterocyclic ring system;
- $R_4$ is selected from C1-4 alkyl, alkenyl, alkynyl, alkoxy carbonyl, alkoxy dicarbonyl, acrylic, alkoxy, alkoxy alkyl, aryloxy alkyl, alkyl carboxylate as part of a betaine, inner salt, or Zwitterion form, halo alkyl, hydroxy alkyl, nitrile, or propargyl;
- $R_6$ is selected from C1-4 alkyl, alkoxy, hydroxy, alkoxy alkyl, hydroxy alkyl, or epoxy; and
- including any acceptable salts or solvates thereof.

2. The method of claim 1, wherein the compound is at least one of N-(2-Phenoxyethyl)-2-isothiocyanato-N,N-dimethylethan-1-aminium triflate, N-(2-isothiocyanatoethyl)-N,N-dimethylprop-2-yn-1-aminium bromide, 3-Isothiocyanato-N,N-diethyl-N-methylpropanaminium iodide, and N-(2-isothiocyanatoethyl)-2-(methoxycarbonyl)-N,N-dimethylprop-2-en-1-aminium bromide, or pharmaceutically acceptable salts thereof.

3. The method of claim 1, wherein the compound is at least one of N,N-Diethyl-2-isothiocyanato-N-methylpropanaminium iodide, N-(2-Bromoethyl)-3-isothiocyanato-N,N-diethylpropan-1-aminium triflate, N-(Ethoxypropyl-2,3-dione)-3-isothiocyanato-N,N-diethylpropan-1-aminium bromide, or pharmaceutically acceptable salts thereof.

4. The method of claim 1 further comprising contacting the bacterium with a second agent that is at least one of Omega 3 oil, salicylic acid, dimethylbutanol, garlic oil, olive oil, krill oil, Co enzyme Q-10, a probiotic, a prebiotic, dietary fiber, *psyllium* husk, bismuth salts, phytosterols, grape seed oil, green tea extract, vitamin D, an antioxidant, turmeric, curcumin, resveratrol, activated charcoal, or copper chlorophyllin.

5. The method of claim 1, wherein conversion of choline or carnitine to trimethylamine (TMA) is inhibited by from about 1% to about 100%.

6. The method of claim 1, wherein conversion of choline or carnitine to trimethylamine (TMA) is inhibited by at least 50%.

7. The method of claim 1, wherein the bacterium is at least one of *Proteus mirabilis, Desulfovibrio alaskensis, Clostridium ljungdahlii, C. scindens, C. aldenense, C. aminobutyricum, Collinsella tanakaei, Anaerococcus vaginalis, Streptococcus dysgalactiae, Desultitobacterium hafniense, Klebsiella variicola, K pneumonia, Proteus penneri, Eggerthella lenta, Edwardsiella tarda, Escherichia coli,* or *E. fergusonii*.

8. A method of inhibiting the conversion of choline to trimethylamine (TMA) by a bacterium comprising: contacting the bacterium with a compound set forth in Formula (II):

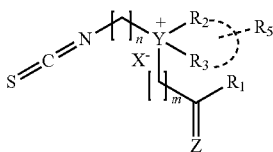

Formula (II)

wherein $R_1$ is H, $C_1$-$C_4$ alkoxy, Br, Cl, F, I, or is selected from

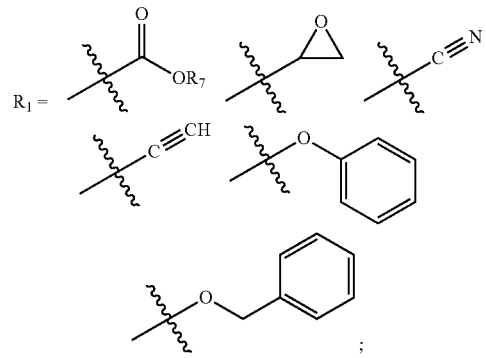

$Y^+$ is selected from a quaternary nitrogen; $X^-$ is an anion; n is selected from 1, 2 or 3; $R_2$ and $R_3$ are independently selected from C1-4 alkyl or bound together forming an aliphatic, aromatic or heterocyclic ring system;
Z is O, $CH_2$, or H, H;
m is 0, 1 or 2;
$R_5$ is hydroxyl, or hydroxyl alkyl; and
$R_7$ is H, or $C_{1-4}$ alkyl; and
including any acceptable salts or solvates thereof.

9. The method of claim 8, wherein the compound is at least one of N-(2-Phenoxyethyl)-2-isothiocyanato-N,N-dimethylethan-1-aminium triflate, N-(2-isothiocyanatoethyl)-N,N-dimethylprop-2-yn-1-aminium bromide, 3-Isothiocyanato-N,N-diethyl-N-methylpropanaminium iodide, and N-(2-isothiocyanatoethyl)-2-(methoxycarbonyl)-N,N-dimethylprop-2-en-1-aminium bromide, or pharmaceutically acceptable salts thereof.

10. The method of claim 8, wherein the compound is at least one of N,N-Diethyl-2-isothiocyanato-N-methylpropanaminium iodide, N-(2-Bromoethyl)-3-isothiocyanato-N,N-diethylpropan-1-aminium triflate, N-(Ethoxypropyl-2,3-dione)-3-isothiocyanato-N,N-diethylpropan-1-aminium bromide, or pharmaceutically acceptable salts thereof.

11. The method of claim 8 further comprising contacting the bacterium with a second agent that is at least one of Omega 3 oil, salicylic acid, dimethylbutanol, garlic oil, olive oil, krill oil, Co enzyme Q-10, a probiotic, a prebiotic, dietary fiber, *psyllium* husk, bismuth salts, phytosterols, grape seed oil, green tea extract, vitamin D, an antioxidant, turmeric, curcumin, resveratrol, activated charcoal, or copper chlorophyllin.

12. The method of claim 8, wherein conversion of choline or carnitine to trimethylamine (TMA) is inhibited by from about 1% to about 100%.

13. The method of claim 8, wherein conversion of choline or carnitine to trimethylamine (TMA) is inhibited by at least 50%.

14. The method of claim 8, wherein the bacterium is at least one of *Proteus mirabilis, Desulfovibrio alaskensis,*

*Clostridium ljungdahlii, C. scindens, C. aldenense, C. aminobutyricum, Collinsella tanakaei, Anaerococcus vaginalis, Streptococcus dysgalactiae, Desultitobacterium hafniense, Klebsiella variicola, K pneumonia, Proteus penneri, Eggerthella lenta, Edwardsiella tarda, Escherichia coli,* or *E. fergusonii.*

15. A compound:

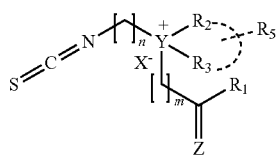

Formula (II)

wherein $R_1$ is, $C_1$-$C_4$ alkoxy, Br, Cl, F, I, or is selected from

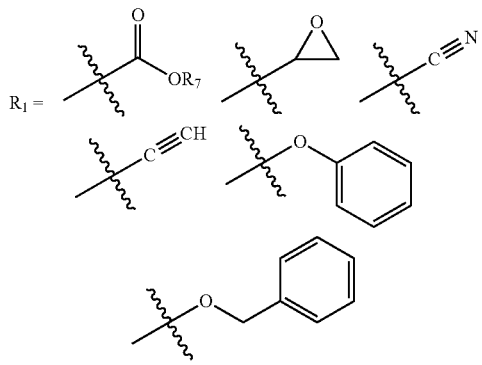

$Y^+$ is selected from a quaternary nitrogen; $X^-$ is an anion; n is selected from 1, 2 or 3; $R_2$ and $R_3$ are independently selected from C1-4 alkyl or bound together forming an aliphatic, aromatic or heterocyclic ring system;
Z is O, $CH_2$, or H, H;
m is 0, 1 or 2;
$R_5$ is hydroxyl, or hydroxyl alkyl; and
$R_7$ is H, or $C_{1-4}$ alkyl and
including any acceptable salts or solvates thereof.

16. The compound of claim 15, wherein the compound is at least one compound selected from N-(Ethoxycarbonylethyl)-3-isothiocyanato-N,N-diethylpropan-1-aminium bromide; N-(Ethoxycarbonylethyl)-2-isothiocyanato-N,N-dimethylethan-1-aminium bromide; N-(Ethoxypropyl-2,3-dione)-2-isothiocyanato-N,N-dimethylethan-1-aminium bromide; N-(Ethoxypropyl-2,3-dione)-3-isothiocyanato-N,N-diethylpropan-1-aminium bromide; N-(2-Bromoethyl)-3-isothiocyanato-N,N-diethylpropan-1-aminium triflate; N-Cyanomethyl-2-isothiocyanato-N,N-diethylethan-1-aminium bromide; N-Cyanomethyl-3-isothiocyanato-N,N-diethylpropan-1-aminium bromide, N-(2-Phenoxyeth y)-3-isothiocyanato-N,N-diethylpropan-1-aminium triflate; N-(2-Benzyloxyethyl)-2-isothiocyanato-N,N-dimethylethan-1-aminium triflate; N-(2-Benzyloxyethyl)-3-isothiocyanato-N,N-diethylpropan-1-aminium triflate; N-(2-Phenoxyethyl)-2-isothiocyanato-N,N-dimethylethan-1-aminium triflate; N-(2-Bromoethyl)-2-isothiocyanato-N,N-dimethylethan-1-aminium triflate; N-(Oxiranylmethyl)-2-isothiocyanato-N,N-dimethylethan-1-aminium triflate; N-(Oxiranylmethyl)-3-isothiocyanato-N,N-diethylpropan-1-aminium triflate; N-(2-Methoxyethyl)-2-isothiocyanato-N,N-dimethylethan-1-aminium triflate; N-(2-Methoxyethyl)-3-isothiocyanato-N,N-diethylpropan-1-aminium triflate; N-(2-Ethoxyethyl)-2-isothiocyanato-N,N-dimethylethan-1-aminium triflate; N-(2-Ethoxyethyl)-3-isothiocyanato-N,N-diethylpropan-1-aminium triflate; N-(3-Methoxypropyl)-2-isothiocyanato-N,N-dimethylethan-1-aminium triflate; N-(3-Methoxyethyl)-3-isothiocyanato-N,N-diethylpropan-1-aminium triflate; N-(2-Chloroethyl)-2-isothiocyanato-N,N-dimethylethan-1-aminium triflate; N-(3-Chloropropyl)-2-isothiocyanato-N,N-dimethylethan-1-aminium triflate; N-(2-Chloroethyl)-3-isothiocyanato-N,N-diethylpropan-1-aminium triflate; N-(3-Chloropropyl)-3-isothiocyanato-N,N-diethylpropan-1-aminium triflate; N-(2-Fluorooethyl)-3-isothiocyanato-N,N-diethylpropan-1-aminium triflate; 1-(2-Isothiocyanatoethyl)pyridin-1-ium bromide, 1-(2-Isothiocyanatoethyl)-3-hydroxypyridinium bromide, 1-(2-Isothiocyanatoethyl)-(2-hydroxymethyl)pyridinium triflate; 2-(hydroxymethyl)-1-(3-isothiocyanatopropyl)pyridin-1-ium trifluoromethanesulfonate; 3-hydroxy-1-(3-isothiocyanatopropyl)pyridin-1-ium trifluoromethanesulfonate; 1-(2-hydroxyethyl)-1-(2-isothiocyanatoethyl)piperidin-1-ium trifluoromethanesulfonate; 2-(hydroxymethyl)-1-(2-isothiocyanatoethyl)-1-methylpiperidin-1-ium trifluoromethanesulfonate: 1-(2-hydroxyethyl)-1-(3-isothiocyanatopropyl)piperidin-1-ium trifluoromethanesulfonate; N-(2-hydroxyethyl)-3-isothiocyanato-N,N-dimethylpropan-1-aminium trifluoromethanesulfonate; N-(2-isothiocyanatoethyl)-N,N-dimethylprop-2-yn-1-aminium bromide; N-(2-isothiocyanatoethyl)-2-(methoxycarbonyl)-N,N-dimethylprop-2-en-1-aminium bromide; 4-hydroxy-1-(2-isothiocyanatoethyl)-1-methylpiperidin-1-ium bromide; 4-Methyl-4-(2-isothiocyanatoethyl)morpholinium trifluoromethanesulfonate; 1-Methyl-1-(2-isothiocyanatoethyl)piperidium trifluoromethanesulfonate; 1-(2-Isothiocyanatoethyl)quinuclidinium trifluoromethanesulfonate; 4-Methyl-4-(3-isothiocyanatopropyl)morpholinium trifluoromethanesulfonate; or 1-Methyl-1-(3-isothiocyanatopropyl)piperidinium trifluoromethanesulfonate; 1-(3-Isothiocyanatopropyl)quinuclidinium trifluoromethanesulfonate.

17. A method of preparing a compound as set forth in FORMULA (II) comprising:

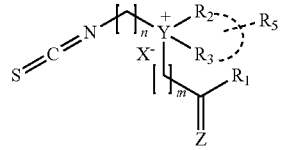

wherein $R_1$ is $C_1$-$C_4$ alkoxy, Br, Cl, F, I, or is selected from

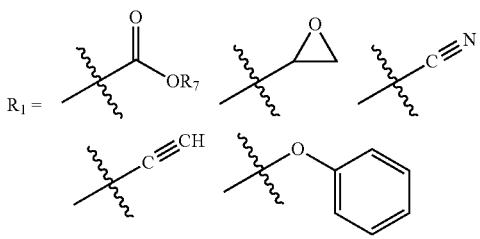

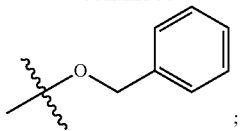

Y⁺ is selected from a quaternary nitrogen; X⁻ is an anion; n is selected from 1, 2 or 3; $R_2$ and $R_3$ are independently selected from C1-4 alkyl or bound together forming an aliphatic, aromatic or heterocyclic ring system;

Z is O, $CH_2$, or H, H;

m is 0, 1 or 2;

$R_5$ is hydroxyl, or hydroxyl alkyl; and $R_7$ is H, or C1-4 alkyl; and including any acceptable salts or solvates thereof; reacting compound A;

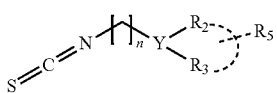

Compound (A)

with a compound of structure B:

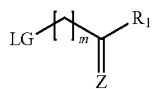

wherein LG is a suitable leaving group known to one skilled in the art.

18. A method of preparing a compound as set forth in FORMULA (II) comprising:

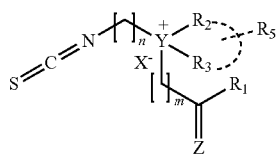

Formula (II)

wherein $R_1$ is H, $C_1$-$C_4$ alkoxy, Br, Cl, F, I, or is selected from

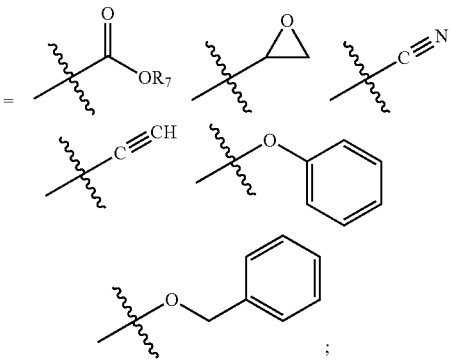

$R_1 =$

Y⁺ is selected from a quaternary nitrogen; X⁻ is an anion; n is selected from 1, 2 or 3; $R_2$ and $R_3$ are independently selected from C1-4 alkyl or bound together forming an aliphatic, aromatic or heterocyclic ring system;

Z is O, $CH_2$, or H, H;

m is 0, 1 or 2;

$R_5$ is hydroxyl, or hydroxyl alkyl; and $R_7$ is H, or C1-4 alkyl; and including any acceptable salts or solvates thereof; reacting compound C:

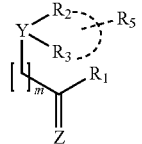

Compound (C)

With a compound of structure D:

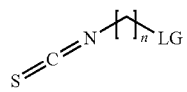

wherein LG is a suitable leaving group known to one skilled in the art.

19. Method of claim 18 wherein the leaving group LG is at least one of chloride, bromide, iodide, triflate, mesylate, or tosylate.

* * * * *

```
                       SEQUENCE LISTING

<160> NUMBER OF SEQ ID NOS: 5

<210> SEQ ID NO 1
<211> LENGTH: 2146
<212> TYPE: DNA
<213> ORGANISM: Escherichia coli

<400> SEQUENCE: 1
atgagcaatc tgagccctga ctttgtacta cccgaaaatt tttgcgctaa cccgcaagag      60
gcgtggacca ttcctgcccg tttttatacc gatcagaacg cgtttgaaca cgaaaaagag     120
aacgtcttcg ccaaaagctg gatttgcgtc gctcacagca gcgaactggc gaatgccaat     180
gattatgtga cgcgtgagat cattggcgaa agcatcgtgc tggtacgcgg tcgtgataag     240 gtttttgcgcg cgttctataa cgtgtgtccg caccgtggtc atcagttgtt gagcggtgaa     300
ggaaaagcaa aaaatgtgat tacctgcccg tatcacgcat gggcattcaa actcgatggc     360
aacctggccc atgcacgtaa ctgcgaaaac gtcgccaatt tcgatagcga caaagcgcaa     420
ctggttccgg tgcgtctgga agaatatgcc ggattcgtct tcatcaacat ggaccccaac     480
gccaccagcg tagaagatca attacccggc ctgggcgcga aagtgctgga agcctgcccg     540
```

```
gaagtccacg atctgaaact ggcggcccgc tttaccaccc gcacgcctgc caactggaag      600
aacattgtcg ataactatct cgagtgctat cactgtggtc cggcgcatcc aggtttctcc      660
gactccgtac aggttgatcg ttactggcac accatgcacg gtaactggac gctgcaatac      720
ggtttcgcca aaccgtccga acagtcgttt aaatttgaag agggtacgga tgcggcattc      780
cacggtttct ggctgtggcc gtgcacgatg ctgaacgtca ccccgatcaa agggatgatg      840
acggtcattt atgaattccc ggtggattct gaaactaccc tgcaaaacta cgatatttac      900
ttcaccaatg aagagttaac cgacgagcaa aaatcgctga ttgagtggta tcgcgatgtg      960
ttccgtccgg aagatttacg tctggttgaa agcgtacaga aagggctgaa atcgcgtggc     1020
tatcgtggtc aggggcgcat catggccgac agtagcggta gtggcatttc cgaacatggt     1080
atcgcccatt tccataatct gctggcgcag gtgtttaagg actaatgaca tcggcggcgg     1140
tattttccgc cgctgggctg attttgatg gagtacagca atgtcagact atcaaatgtt      1200
tgaagtacag gtgagccagg ttgaaccccct taccgaacag gtgaaacgct tcacgctggt     1260
ggcaaccgat ggcaaaccat acctgcgtt taccggagga agtcacgtca ttgtgcagat      1320
gagcgatggt gataaccagt acagcaatgc gtattcacta ctgagttcgc cgcatgacac     1380
ctcttgttat cagattgccg ttcggctgga ggaaaactcg cgcggcggtt cccgcttttt     1440
gcatcagcag gtaaaagtgg gcgatcggtt aacgatttca acgcctaata acctgtttgc     1500
gctaattccc tcagccagaa agcatctgtt tatcgcgggc ggtattggta tcacccctt     1560 cctgtcgcac atggcagagc tgcaacacag cgacgtcgac tggcagctac attactgctc     1620
gcgaaatcca gaaagttgcg catttcgtga tgagctagtc cagcatccgc aggctgagaa     1680
agtccatttg catcattcat caaccggaac acgactggaa ttagcgcgat tattggcgga     1740
tatcgaacct ggcacacacg tttataccctg tggccccgag cgctaattg aagcggtaag    1800 aagtgaagct gcgcgtctgg acatcgccgc cgatacgctg cactttgagc aatttgctat     1860
cgaagacaaa accggcgatg catttaccct ggtgcttgcc cgttccggaa aagagtttgt     1920
ggtgccggaa gagatgacta ttttgcaggt tattgaaaat aataaagccg cgaaagtgga     1980
atgtttatgt cgtgaagggg tatgcggaac ctgcgaaaca gcaatactgg aaggtgaagc     2040
tgaccatcgg gatcaatatt ttagcgatga agagcgtgcc agccagcaaa gtatgttgat     2100
ctgttgttcg cgtgcgaagg gtaaacgcct ggtgttggat ttgtag                    2146
```

<210> SEQ ID NO 2
<211> LENGTH: 374
<212> TYPE: PRT
<213> ORGANISM: Escherichia coli

<400> SEQUENCE: 2

```
Met Ser Asn Leu Ser Pro Asp Phe Val Leu Pro Glu Asn Phe Cys Ala
1               5                   10                  15

Asn Pro Gln Glu Ala Trp Thr Ile Pro Ala Arg Phe Tyr Thr Asp Gln
            20                  25                  30

Asn Ala Phe Glu His Glu Lys Glu Asn Val Phe Ala Lys Ser Trp Ile
        35                  40                  45

Cys Val Ala His Ser Ser Glu Leu Ala Asn Ala Asn Asp Tyr Val Thr
    50                  55                  60

Arg Glu Ile Ile Gly Glu Ser Ile Val Leu Val Arg Gly Arg Asp Lys
65                  70                  75                  80

Val Leu Arg Ala Phe Tyr Asn Val Cys Pro His Arg Gly His Gln Leu
                85                  90                  95
```

```
Leu Ser Gly Glu Gly Lys Ala Lys Asn Val Ile Thr Cys Pro Tyr His
                100                 105                 110

Ala Trp Ala Phe Lys Leu Asp Gly Asn Leu Ala His Ala Arg Asn Cys
            115                 120                 125

Glu Asn Val Ala Asn Phe Asp Ser Asp Lys Ala Gln Leu Val Pro Val
130                 135                 140

Arg Leu Glu Glu Tyr Ala Gly Phe Val Phe Ile Asn Met Asp Pro Asn
145                 150                 155                 160

Ala Thr Ser Val Glu Asp Gln Leu Pro Gly Leu Gly Ala Lys Val Leu
                165                 170                 175

Glu Ala Cys Pro Glu Val His Asp Leu Lys Leu Ala Ala Arg Phe Thr
            180                 185                 190

Thr Arg Thr Pro Ala Asn Trp Lys Asn Ile Val Asp Asn Tyr Leu Glu
        195                 200                 205

Cys Tyr His Cys Gly Pro Ala His Pro Gly Phe Ser Asp Ser Val Gln
    210                 215                 220

Val Asp Arg Tyr Trp His Thr Met His Gly Asn Trp Thr Leu Gln Tyr
225                 230                 235                 240

Gly Phe Ala Lys Pro Ser Glu Gln Ser Phe Lys Phe Glu Glu Gly Thr
                245                 250                 255

Asp Ala Ala Phe His Gly Phe Trp Leu Trp Pro Cys Thr Met Leu Asn
            260                 265                 270

Val Thr Pro Ile Lys Gly Met Met Thr Val Ile Tyr Glu Phe Pro Val
        275                 280                 285

Asp Ser Glu Thr Thr Leu Gln Asn Tyr Asp Ile Tyr Phe Thr Asn Glu
    290                 295                 300

Glu Leu Thr Asp Glu Gln Lys Ser Leu Ile Glu Trp Tyr Arg Asp Val
305                 310                 315                 320

Phe Arg Pro Glu Asp Leu Arg Leu Val Glu Ser Val Gln Lys Gly Leu
                325                 330                 335

Lys Ser Arg Gly Tyr Arg Gly Gln Gly Arg Ile Met Ala Asp Ser Ser
            340                 345                 350

Gly Ser Gly Ile Ser Glu His Gly Ile Ala His Phe His Asn Leu Leu
        355                 360                 365

Ala Gln Val Phe Lys Asp
    370

<210> SEQ ID NO 3
<211> LENGTH: 321
<212> TYPE: PRT
<213> ORGANISM: Escherichia coli

<400> SEQUENCE: 3

Met Ser Asp Tyr Gln Met Phe Glu Val Gln Val Ser Gln Val Glu Pro
1               5                   10                  15

Leu Thr Glu Gln Val Lys Arg Phe Thr Leu Val Ala Thr Asp Gly Lys
                20                  25                  30

Pro Leu Pro Ala Phe Thr Gly Gly Ser His Val Ile Val Gln Met Ser
            35                  40                  45

Asp Gly Asp Asn Gln Tyr Ser Asn Ala Tyr Ser Leu Leu Ser Ser Pro
        50                  55                  60

His Asp Thr Ser Cys Tyr Gln Ile Ala Val Arg Leu Glu Glu Asn Ser
65                  70                  75                  80

Arg Gly Gly Ser Arg Phe Leu His Gln Gln Val Lys Val Gly Asp Arg
```

```
                        85                  90                  95
Leu Thr Ile Ser Thr Pro Asn Asn Leu Phe Ala Leu Ile Pro Ser Ala
            100                 105                 110

Arg Lys His Leu Phe Ile Ala Gly Gly Ile Gly Ile Thr Pro Phe Leu
            115                 120                 125

Ser His Met Ala Glu Leu Gln His Ser Asp Val Asp Trp Gln Leu His
            130                 135                 140

Tyr Cys Ser Arg Asn Pro Glu Ser Cys Ala Phe Arg Asp Glu Leu Val
145                 150                 155                 160

Gln His Pro Gln Ala Glu Lys Val His Leu His Ser Ser Thr Gly
                165                 170                 175

Thr Arg Leu Glu Leu Ala Arg Leu Leu Ala Asp Ile Glu Pro Gly Thr
            180                 185                 190

His Val Tyr Thr Cys Gly Pro Glu Ala Leu Ile Glu Ala Val Arg Ser
            195                 200                 205

Glu Ala Ala Arg Leu Asp Ile Ala Ala Asp Thr Leu His Phe Glu Gln
            210                 215                 220

Phe Ala Ile Glu Asp Lys Thr Gly Asp Ala Phe Thr Leu Val Leu Ala
225                 230                 235                 240

Arg Ser Gly Lys Glu Phe Val Val Pro Glu Glu Met Thr Ile Leu Gln
            245                 250                 255

Val Ile Glu Asn Asn Lys Ala Ala Lys Val Glu Cys Leu Cys Arg Glu
            260                 265                 270

Gly Val Cys Gly Thr Cys Glu Thr Ala Ile Leu Glu Gly Glu Ala Asp
            275                 280                 285

His Arg Asp Gln Tyr Phe Ser Asp Glu Glu Arg Ala Ser Gln Gln Ser
            290                 295                 300

Met Leu Ile Cys Cys Ser Arg Ala Lys Gly Lys Arg Leu Val Leu Asp
305                 310                 315                 320

Leu

<210> SEQ ID NO 4
<211> LENGTH: 33
<212> TYPE: DNA
<213> ORGANISM: Escherichia coli

<400> SEQUENCE: 4
catgccatat gagcaatctg agccctgact ttg                           33

<210> SEQ ID NO 5
<211> LENGTH: 38
<212> TYPE: DNA
<213> ORGANISM: Escherichia coli

<400> SEQUENCE: 5
catactgcag ctacaaatcc aacaccaggc gtttaccc                      38
```